United States Patent [19]
Brown et al.

[11] Patent Number: 5,420,245
[45] Date of Patent: May 30, 1995

[54] TETRAPEPTIDE-BASED INHIBITORS OF FARNESYL TRANSFERASE

[75] Inventors: Michael S. Brown; Joseph L. Goldstein; Yuval Reiss, all of Dallas, Tex.

[73] Assignee: Board of Regents, The University of Texas, Austin, Tex.

[21] Appl. No.: 863,169

[22] Filed: Apr. 3, 1992

Related U.S. Application Data

[60] Division of Ser. No. 822,011, Jan. 16, 1992, abandoned, which is a continuation-in-part of Ser. No. 615,715, Nov. 20, 1990, Pat. No. 5,141,851, which is a continuation-in-part of Ser. No. 510,706, Apr. 18, 1990, abandoned.

[51] Int. Cl.⁶ .................... A61K 37/00; A61K 37/02; C07K 5/00; C07K 7/00
[52] U.S. Cl. ................................ 530/328; 530/329; 530/330
[58] Field of Search ............... 530/328, 329, 330, 350; 514/15, 16, 17, 18

[56] References Cited

U.S. PATENT DOCUMENTS

| | | | |
|---|---|---|---|
| 5,026,554 | 6/1991 | Bartizal et al. | 424/404 |
| 5,043,268 | 8/1991 | Stock | 435/15 |
| 5,055,487 | 10/1991 | Bartizal et al. | 514/452 |
| 5,104,975 | 4/1992 | McCormick et al. | 530/350 |
| 5,141,851 | 8/1992 | Brown et al. | 435/15 |
| 5,185,248 | 2/1993 | Barbacid | 435/15 |
| 5,202,456 | 4/1993 | Rando | 558/438 |
| 5,234,839 | 8/1993 | McCormick et al. | 436/501 |
| 5,238,922 | 8/1993 | Graham et al. | 514/18 |
| 5,245,061 | 9/1993 | Singh | 554/121 |

FOREIGN PATENT DOCUMENTS

| | | |
|---|---|---|
| 0456180 | 11/1991 | European Pat. Off. ........ C12N 9/10 |
| 0461869A2 | 12/1991 | European Pat. Off. . |
| 0520823 | 12/1992 | European Pat. Off. . |
| 0523873 | 1/1993 | European Pat. Off. . |
| 0528486 | 2/1993 | European Pat. Off. . |
| 0535730 | 4/1993 | European Pat. Off. . |
| 0535731 | 4/1993 | European Pat. Off. . |
| 2261373 | 5/1993 | United Kingdom . |
| 2261374 | 5/1993 | United Kingdom . |
| 2261375 | 5/1993 | United Kingdom . |
| WO91/16340 | 10/1991 | WIPO . |

OTHER PUBLICATIONS

Casey et al., *Proc. Natl. Acad. Sci.*, vol. 86, Nov. 1989, pp. 8323–8327.
Lowry et al., *Nature*, vol. 341, 5 Oct., 1989, pp. 384–385.
Clarke *et al.*, *Proc. Natl. Acad. Sci. USA*, 85:4643–4647, 1988.
Hancock *et al.*, *Cell*, 57:1167–77, 1989.

(List continued on next page.)

*Primary Examiner*—Merrell C. Cashion, Jr.
*Assistant Examiner*—A. M. Davenport
*Attorney, Agent, or Firm*—Arnold, White & Durkee

[57] ABSTRACT

Disclosed are methods and compositions for the identification, characterization and inhibition of mammalian farnesyl protein transferases, enzymes involved in the farnesylation of various cellular proteins, including cancer related ras proteins such as $p21^{ras}$. One farnesyl protein transferase which is disclosed herein exhibits a molecular weight of between about 70,000 and about 100,000 upon gel exclusion chromatography. Also disclosed are methods and compositions for the preparation of farnesyl transferase by recombinant means, following the molecular cloning and co-expression of its two subunits, for assay and purification of the enzyme, as well as procedures for using the purified enzyme in screening protocols for the identification of possible anticancer agents which inhibit the enzyme and thereby prevent expression of proteins such as $p21^{ras}$. Also disclosed is a families of compounds which act either as false substrates for the enzyme or as pure inhibitors and can therefore be employed for inhibition of the enzyme. The most potent inhibitors are ones in which phenylalanine occurs at the third position of a tetrapeptide whose amino terminus is cysteine.

10 Claims, 21 Drawing Sheets

OTHER PUBLICATIONS

Schafer et al., *Science*, 245:379-385, 1989.
Bos, *Cancer Research*, 49:4682-4689, 1989.
Goldstein et al., *Nature*, 343:425-430, 1990.
Schaber et al., *Journal of Biol. Chem.*, 265:14701-14704, 1990.
Manne et al., *Proc. Natl Acad. Sci. USA*, 87:7541-7545, 1990.
Reiss et al., *Cell*, 62:81-88, 1990.
Reiss et al., *Proc. Natl. Acad. Sci. USA*, 88:732-736, 1991.
Chen, et al., *Cell*, 66:327-334, 1991.
Goldstein, et al., *J Biol Chem*, 266(24):15575-15578, 1991.
Goodman, et al., *Yeast*, 4:271-281, 1988.
Goodman, et al., *Proc. Natl Acad. Sci.*, 87:9665-9669, 1990.
Schaber, et al., *Chem. Abstr.*, 114:302, Abstract #38170r, 1991.
Kim, et al., *Chem. Abstr.*, 114:373, Abstract #3711r, 1991.
Kohl et al., *J. Biol. Chem.*, 266(28):18884-18888, 1991.
He et al., *PNAS*, 88:11373-11377, 1991.
International Search Report.
Reiss, et al., "Divalent Cation and Prenyl Pyrophosphate Specificities of the Protein Farnesyltransferase from Rat Brain, a Zinc Metalloenzyme," *J. Biol. Chem.*, 267:6403-6408, 1992. Published in USA.
Seabra, et al., "Protein Farnesyltransferase and Geranylgeranyltransferase Share a Common α Subunit," *Cell*, 65:429-434, 1991. Published in USA.
Reiss, et al., "Purification of ras Farnesyl:Protein Transferase," *Methods: A Companion to Methods in Enzymology*, 1(3):241-245, 1990. Published in USA.
Nancy E. Kohl, et al., "Selective Inhibition of *ras*-Dependent Transformation by a Farnesyltransferase Inhibitor", *Science*, 260:1934-1937 (1993).

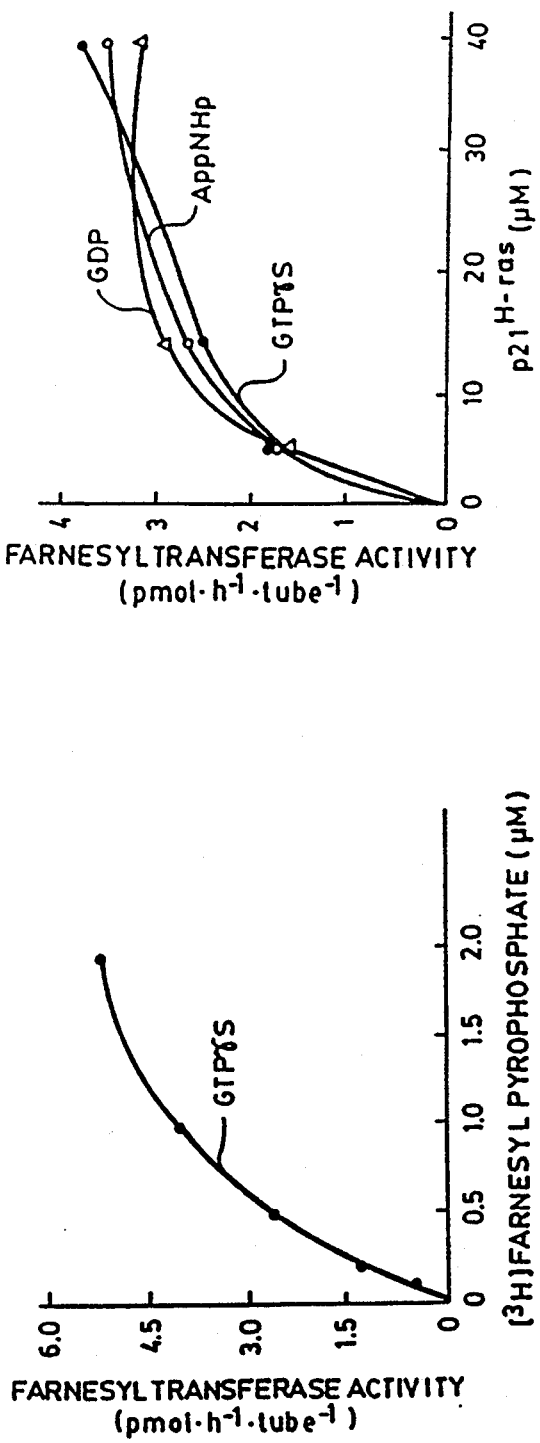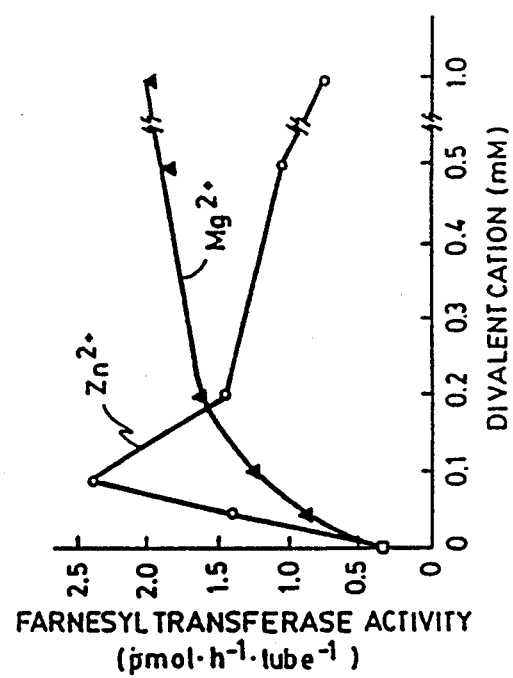

PCR Primer α1 →

GA(T/C) GCI ATI GA(A/G)(T/C)TA AAC GCA GCC AAC TAT ACG GTC TGG CAC TT
Asp Ala Ile Glu Leu Asn Ala Ala Asn Tyr Thr Val Trp His Phe Arg

CAI ACC GT(G/A) AA(G/A)(G/A)(C/T)
← PCR Primer α2

FIG. 16A

| | | |
|---|---|---|
| Rat FT-α | 1 | MAATEGVGESAPGGEPGQPEQPPPPPPPPPAQQPQEEEMAAEAGEAAASP |
| YEAST RAM2 | 1 | M--EEYDYS-DVKPLPIE----TDLQDELCRIMYTEDYKRLMGLARA- |
| | 51 | MDDGFLSLDSPTYVLYRDRAEWADIDPVPQNDGPSPVVQIIYSEKFRDVY |
| | 41 | -LISLNELSP-RAL-QLTAE-IID-V----APAFYTIWNY----R |
| | 101 | DYFRAVLQRDERSERAFKLTRDAIELNAAANYTVWHFRRVLLRSLQKDLQE |
| | 73 | -FNIM-RHMMSE-SEDT-VLYLN-------KELDWL-DEVT |
| | 151 | EMNYIIAIIEEQPKNYQWHHRRVLVEWLKDPS-QELEFIADILNQDAK |
| | 102 | LNN-------PKNYQIWSYRQSLLKLHPSPSFKRELPILKLMIDDDSK |
| | 199 | NYHAWQHRQWVIQEFRLWDNELQYVDQLLKEDVRNNSWNQRHFVISNTT |
| | 143 | NYHVWSYRKWCCLFFSDFQHELAYASDLIETDIYNNSAWTHRMFYWVNAK |
| | 249 | GYSDRAVLEREMQYTLEMIKLVPHNESAWNYLKG-IL-GDR-GLS-RY |
| | 193 | DVISKVELADELQFIMDKIQLVPQNISPWTYLRGFQELFHDRLQWDSKVV |
| | 293 | PNLLNQLLD-L-QPSHSSPYLIAFLVDIYEDMLENQCDNKEDILNKALEL |
| | 243 | DFATTFIGDVLSLPIGSPEDLPEIESSYALEFLAYHWGADPCTRDNAVKA |
| | 341 | CEILAKEKDTIRKEYWRYIGRSLQSKHSRESDIPASV  377 |
| | 293 | YSLLAIKYDPIRKNLWHHKINNLN  316 |

FIG. 17

```
Rat FT-β       1  M--ASSSS------F--TYYCPPSSSPV--WSEPLYSLRPEHARERLQDDSV
Yeast DPR1/RAM1 1 MRQRVGRSLARAKFINTALLGRKRPVMERVVDIAHVDSSKAIQPL-MKEL 41  ETMTSLEQAKVEEKIQEVFSSYKFNHLVPRLVLQREKHFHYL-KRGLRQLIDAYECLDAS
              50  ETDTTEARYKVLQSVLETYDDEK-N-IEP--ALTKEFHKMYLDVAFEISLPPQMTALDAS 100  RPWLCYWILHSLELLDEPIPQIVATDVCQFLEL-CQSPDGG-FGGGPGQYPHLAPITYAAV
             106  QPWMLYWIANSLKVMD-RDWLSDDTKRKTVVKLFTISPSGGPFGGGPGQLSHLASITYAAI 158  NAL-CIIGTEEAYNVINREKLLQYLYSLKQPDGSF-LMHVGGEVDVRSAYCAASVASLIN
             165  NALSLCDNIDGCWDRIDRKGIYQWLISLKFPNGGFKTCLEVGEVDTRGIYCALSIATLLN 216  IIIPDLFEGTAEWIARCQNWEGGIGGVF-GMEAHGGYTFCGLAALVILKKERSLNLKSLL
             225  ILIEELIEGVLNYLKNCQNYEGGFGSCPHVDEAHGGYTFCATASLAILRSMDQINVEKLL 275  QWVTSRQMRFEGGFQGRCNKLVDGCYSFWQAGLLPLLHRALHAQGDPALSMSHMMFHQQA
             285  EWSSARQLQEERGFCGRSNKLVDGCYSFWVGG--SAAILEAFG--YGQCFNKHA 335  LQEYIIMCCQ-CPAGGLLDKPGKSRDFYHTCYCLSGLSIAQHFGSGAMLHDVVMGVPENV
             335  LRDYIIYCCQEKEQPGLRDKPGAHSDFYHTNYCLLGLAVAESSYS-CTPND--SPHN- 394  LQPIHPVYNIGPDK-VIQATTHFL-QKPVPGFEECEDAVISDPATD   437
             389  IKCI-PDRIIGSSKLTDVNPVYGLPIENVRKIIHYFKSNLSSPS--   431
```

FIG. 18

TETRAPEPTIDE-BASED INHIBITORS OF FARNESYL TRANSFERASE

The government may own certain rights in the present invention pursuant to NIH grant number 5-P01-HL20948.

This is a divisional of application Ser. No. 07/822,011 filed Jan. 16, 1992, and now abandoned, which is a continuation in part of PCT application Ser. No. U.S. 91/02650, filed with the US/RO on Apr. 18, 1991, which is a continuation in part of U.S. Ser. No. 615,715, filed Nov. 20, 1990, now U.S. Pat. No. 5,141,851, which is a continuation in part of U.S. Ser. No. 510,706, filed Apr. 18, 1990, now abandoned.

BACKGROUND OF THE INVENTION

1. Field of the Invention

This invention relates to the molecular cloning, purification, characterization and inhibition of farnesyl:-protein transferase, an enzyme involved in expression of the cancer phenotype, for example, in the transfer of farnesyl groups to oncogenic ras proteins. In particular aspects, the invention relates to nucleic acid segments encoding mammalian enzyme subunits which can be used as probes for the selection of related sequences or in the production of the holoenzyme or subunit polypeptides thereof, to the purification of the native or recombinant enzyme, as well as to assay methods for the identification of candidate substances which will inhibit the activity of the enzyme.

2. Description of the Related

In recent years, some progress has been made in the elucidation of cellular events lending to the development or progression of various types of cancers. A great amount of research has centered on identifying genes which are altered or mutated in cancer relative to normal cells. In fact, genetic research has led to the identification of a variety of gene families in which mutations can lead to the development of a wide variety of tumors. The ras gene family is a family of closely related genes that frequently contain mutations involved in many human tumors, including tumors of virtually every tumor group (see, e.g., ref. 1 for a review). In fact, altered ras genes are the most frequently identified oncogenes in human tumors (2).

The ras gene family comprises three genes, H-ras, K-ras and N-ras, which encode similar proteins with molecular weights of about 21,000 (2). These proteins, often termed $p21^{ras}$, comprise a family of GTP-binding and hydrolyzing proteins that regulate cell growth when bound to the inner surface of the plasma membrane (3,4). Overproduction of $P21^{ras}$ proteins or mutations that abolish their GTP-ase activity lead to uncontrolled cell division (5). However, the transforming activity of ras is dependent on the localization of the protein to membranes, a property thought to be conferred by the addition of farnesyl groups (3,6).

A precedent for the covalent isoprenylation of proteins had been established about a decade ago when peptide mating factors secreted by several fungi were shown to contain a farnesyl group attached in thioether linkage to the C-terminal cysteine (7-9). Subsequent studies with the mating a-factor from *Saccharomyces cerevisiae* and farnesylated proteins from animal cells have clarified the mechanism of farnesylation. In each of these proteins the farnesylated cysteine is initially the fourth residue from the C terminus (3, 4, 10). Immediately after translation, in a sequence of events whose order is not yet totally established, a farnesyl group is attached to this cysteine, the protein is cleaved on the C-terminal side of this residue, and the free COOH group of the cysteine is methylated (3, 10, 11, 12). All of these reactions are required for the secretion of active a-factor in Saccharomyces (4).

Most, if not all, of the known $p21^{ras}$ proteins contain the cysteine prerequisite, which is processed by farnesylation, proteolysis and COOH-methylation, just as with the yeast mating factor (3, 4, 10, 11, 12). The farnesylated $p21^{ras}$ binds loosely to the plasma membrane, from which most of it can be released with salt (3). After binding to the membrane, some $P21^{rae}$ proteins are further modified by the addition of palmitate in thioester linkage to cysteines near the farnesylated C-terminal cysteine (3) Palmitylation renders the protein even more hydrophobic and anchors it more tightly to the plasma membrane.

However, although it appears to be clear that farnesylation is a key event in ras-related cancer development, prior to now, the nature of this event has remained obscure. Nothing has been known previously, for example, of the nature of the enzyme or enzymes which may be involved in ras tumorigenesis or required by the tumor cell to achieve farnesylation. If the mechanisms that underlie farnesylation of cancer-related proteins such as $P21^{ras}$ could be elucidated, then procedures and perhaps even pharmacologic agents could be developed in an attempt to control or inhibit expression of the oncogenic phenotype in a wide variety of cancers. It goes without saying that such discoveries would be of pioneering proportions in cancer therapy.

SUMMARY OF THE INVENTION

The present invention addresses one or more shortcomings in the prior art through the identification and characterization of an enzyme, termed farnesyl:protein transferase, involved in the oncogenic process through the transfer of farnesyl groups to various proteins including oncogenic ras proteins. The invention relates particularly to the molecular cloning of mammalian farnesyl:protein transferase subunits, to the purification of the native or recombinant enzyme, to protein and peptide substances that are capable of inhibiting the enzyme, and to assay methods for the identification of further inhibitory compounds.

A certain object of the present invention is therefore to provide ready means for obtaining farnesyl transferase enzymes, by purification of the native enzyme from tissues of choice, or by purification of the recombinant enzyme from host cells that express the constituent subunits, which methods are proposed to be generally applicable to the purification of all such farnesyl protein transferases.

It is an additional object of the invention to provide means for obtaining these enzymes in a relatively purified form, allowing their use in predictive assays for identifying compounds having the ability to reduce the activity of or inhibit the farnesyl transferase activity, particularly in the context of $p21^{ras}$ proteins.

It is a still further object of the invention to identify classes of compounds which demonstrate farnesyl transferase inhibiting activity, along with a potential application of these compounds in the treatment of cancer, particularly ras-related cancers.

Farnesyl:Protein Transferase Characterization

Accordingly, in certain embodiments, the present invention relates to compositions which include a purified farnesyl protein transferase enzyme, characterized as follows:
a) capable of catalyzing the transfer of farnesyl to a protein or peptide having a farnesyl acceptor moiety;
b) capable of binding to an affinity chromatography medium comprised of TKCVIM coupled to a suitable matrix;
c) exhibiting a molecular weight of between about 70,000 and about 100,000 upon gel filtration chromatography; and
d) having a farnesyl transferase activity that is capable of being inhibited by one of the following peptides:
  i) TKCVIM;
  ii) CVIM; or
  iii) KKSKTKCVIM.

As used herein, the phrase "capable of catalyzing the transfer of farnesol to a protein or peptide having a farnesyl acceptor moiety," is intended to refer to the functional attributes of farnesyl transferase enzymes of the present invention, which catalyze the transfer of farnesol, typically in the form of all-trans farnesol, from all-trans farnesyl pyrophosphate to proteins which have a sequence recognized by the enzyme for attachment of the farnesyl moieties. Thus, the term "farnesyl acceptor moiety" is intended to refer to any sequence, typically a short amino acid recognition sequence, which is recognized by the enzyme and to which a farnesyl group will be attached by such an enzyme.

Farnesyl acceptor moieties have been characterized by others in various proteins as a four amino acid sequence found at the carboxy terminus of target proteins. This four amino acid sequence has been characterized as -C-A-A-X, wherein "C" is a cysteine residue, "A" refers to any aliphatic amino acid, and "X" refers to any amino acid. Of course, the term "aliphatic amino acid" is well-known in the art to mean any amino acid having an aliphatic side chain, such as, for example, leucine, isoleucine, alanine, methionine, valine, etc. While the most preferred aliphatic amino acids, for the purposes of the present invention include valine and isoleucine, it is believed that virtually any aliphatic amino acids in the designated position can be recognized within the farnesyl acceptor moiety. In addition, the enzyme has been shown to recognize a peptide containing a hydroxylated amino acid (serine) in place of an aliphatic amino acid (CSIM). Of course, principal examples of proteins or peptides having a farnesyl acceptor moiety, for the purposes of the present invention, will be the p21$^{ras}$ proteins, including p21$^{H-ras}$, P21$^{K-rasA}$, P21$^{K-rasB}$ and p21$^{N-ras}$. Thus, in light of the present disclosure, a wide variety of peptidyl sequences having a farnesyl acceptor moiety will become apparent.

As outlined above, the inventors have discovered that the farnesyl transferase enzyme is capable of binding to an affinity chromatography medium comprised of the peptide TKCVIM, coupled to a suitable matrix. This feature of the farnesyl transferase enzyme was discovered by the present inventors in developing techniques for its isolation. Surprisingly, it has been found that the coupling of a peptide such as one which includes CVIM, as does TKCVIM, to a suitable chromatography matrix allows for the purification of the protein to a significant degree, presumably through interaction and binding of the enzyme to the peptidal sequence. A basis for this interaction could be posited as due to the apparent presence of a farnesyl acceptor moiety within this peptide.

The phrase "capable of binding to an affinity chromatography medium comprised of TKCVIM coupled to a suitable matrix," is intended to refer to the ability of the protein to bind to such a medium under conditions as specified herein below. There will, of course, be conditions, such as when the pH is below 6.0, wherein the farnesyl transferase enzyme will not bind effectively to such a matrix. However, through practice of the techniques disclosed herein, one will be enabled to achieve this important objective.

There are numerous chromatography matrixes which are known in the art that can be applied to the practice of this invention. The inventors prefer to use activated CH-Sepharose 4B, to which peptides such as TKCVIM, or which incorporate the CVIM structure, can be readily attached and washed with little difficulty. However, the present invention is by no means limited to the use of CH-Sepharose 4B, and includes within its intended scope the use of any suitable matrix for performing affinity chromatography known in the art. Examples include solid matrices with covalently bound linkers, and the like, as well as matrices that contain covalently associated avidin, which can be used to bind peptides that contain biotin.

Farnesyl transferase enzymes of the present invention have typically been found to exhibit a molecular weight of between about 70,000 and about 100,000 upon gel filtration chromatography. For comparison purposes, this molecular weight was identified for farnesyl protein transferase through the use of a Superose 12 column, using a column size, sample load and parameters as described herein below.

It is quite possible, depending on the conditions employed, that different chromatographic techniques may demonstrate a farnesyl transferase protein that has an apparent molecular weight somewhat different than that identified using the preferred techniques set forth in the examples. It is intended therefore, that the molecular weight determination and range identified for farnesyl transferase in the examples which follow, are designated only with respect to the precise techniques disclosed herein.

It has been determined that the farnesyl:protein transferase can be characterized as including two subunits, each having a molecular weight of about 45 to 50 kDa, as estimated by SDS polyacrylamide gel electrophoresis (PAGE). These subunits have been designated as $\alpha$ and $\beta$, with the $\alpha$ subunit migrating slightly higher than the $\beta$ subunit, which suggests that the $\alpha$ subunit may be slightly larger. From tryptic peptide sequence analyses and molecular cloning the nature of the $\alpha$ and $\beta$ subunits as distinct proteins, encoded by separate genes, has been confirmed. The peptide sequences obtained from the rat brain subunits are as follows:

TABLE I

Farnesyl:Protein Transferase Peptide Sequences $\alpha$ subunit:

TABLE I-continued
Farnesyl:Protein Transferase Peptide Sequences

1)  \* R A E W A D I D P V P Q N D G P S P V V Q I I Y S K \*
    D                                                   E

2)  D A I E L N A A N Y T V W H F R

3)                            \* \* \*
    H F V I S N T T G Y S D H R R
                          R A V

4)  V L V E W L K

5)  L V P H N E S A W N Y L K

6)                \* \*
    L W D N E L Q Y V D Q L L K

β subunit:

7)  \* A Y C A A S V A S L T N I I T P D L F E G V K E
    S                                           T A

8)  \* L L Q W V T S R G
    S               Q

9)  \* I Q A T T H F L Q K P V P G F E E C E D A V T \* D P
    V                                               S

10) I Q E V F S S Y K

11) F E G G F Q G R

12) F N H L V P P R
              P

The sequences shown in Table I were obtained from HPLC-purified tryptic peptides isolated from the α- or β-subunit of purified rat farnesyltransferase (50). Each peptide represents a pure species from a single HPLC peak. Asterisks denote ambiguous residues. The amino acid sequences of all 6 peptides of each subunit were found in the respective cDNA clone except for the differences indicated below the peptide sequence.

The inventors have found that the holoenzyme forms a stable complex with all-trans [$^3$H]farnesyl pyrophosphate (FPP) that can be isolated by gel electrophoresis. The [$^3$H]FFP is not covalently bound to the enzyme, and is released unaltered when the enzyme is denatured. When incubated with an acceptor such as p21$^{H\text{-}ras}$, the complex transfers [$^3$H]farnesyl from the bound [$^3$H]FFP to the ras protein. Furthermore, crosslinking studies have shown that p21$^{H\text{-}ras}$ binds to the β subunit, raising the possiblity that the [3H]FFP binds to the α subunit. If this is the case, it would invoke a reaction mechanism in which the α subunit act as a prenyl pyrophosphate carrier that delivers FPP to p21$^{H\text{-}ras}$, which is bound to the β subunit. Interestingly, the inventors have recently discovered that the e subunit is shared with another prenyltransferase, geranylgeranyltransferase, that attaches 20-carbon geranylgeranyl to Ras-related proteins.

An additional property discovered for farnesyl transferase enzymes is that they can be inhibited by peptides or proteins, particularly short peptides, which include certain structural features, related in some degree to the farnesyl acceptor moiety discussed above. As used herein, the word "inhibited" refers to any degree of inhibition and is not limited for these purposes to only total inhibition. Thus, any degree of partial inhibition or relative reduction in farnesyl transferase activity is intended to be included within the scope of the term "inhibited." Inhibition in this context includes the phenomenon by which a chemical constitutes an alternate substrate for the enzyme, and is therefore farnesylated in preference to the ras protein, as well as inhibition where the compound does not act as an alternate substrate for the enzyme.

Preparation of Farnesyl:Protein Transferase

The present invention is also concerned with techniques for the identification and isolation of farnesyl transferase enzymes, and particularly mammalian farnesyl transferases. Techniques are herein disclosed for the isolation of farnesyl transferase which are believed to be applicable to the purification of the native protein, or alternatively, to the purification of the recombinant enzyme following the molecular cloning and co-expression of the constituent subunits.

An important feature of the purification scheme disclosed herein involves the use of short peptide sequences which the inventors have discovered will bind the enzyme, allowing their attachment to chromatography matrices, such matrices may, in turn, be used in connection with affinity chromatography to purify the enzyme to a relative degree. Thus, in certain embodiments, the present invention is concerned with a method of preparing a farnesyl transferase enzyme which includes the steps of:

(a) preparing a cellular extract which includes the enzyme;

(b) subjecting the extract to affinity chromatography on an affinity chromatography medium to bind the enzyme thereto, the medium comprised of a farnesyl transferase binding peptide coupled to a suitable matrix;

(c) washing the medium to remove impurities; and (d) eluting the enzyme from the washed medium.

Thus, the first step of the purification protocol involves simply preparing a cellular extract which includes the enzyme. The inventors have discovered that the enzyme is soluble in buffers such as low-salt buffers, and it is proposed that virtually any buffer of this type can be employed for initial extraction of the protein from the tissue of choice or from recombinant cells in which the constituent subunits of the enzyme are expressed. The inventors prefer a 50 mM Tris-chloride, pH 7.5, buffer which includes a divalent chelator (e.g., 1 mM EDTA, 1 mM EGTA), as well as protease inhibitors such as phenylmethylsulphonyl fluoride (PMSF) and/or leupeptin. Of course, those of skill in the art will recognize that a variety of other types of buffers may be employed as extractants where desired, so long as the enzyme is extractable in such a buffer and its subsequent activity is not adversely affected to a significant degree.

In embodiments concerning the purification of the native enzyme, the choice of tissue from which one will seek to obtain the farnesyl transferase enzyme is not believed to be of crucial importance. In fact, it is believed that farnesyl transferases are components of virtually all living cells. Therefore, the tissue of choice will typically be that which is most readily available to the practitioner. In that farnesyl transferase action appears to proceed similarly in most systems studied, including, cultured hamster cells, rat brain, and even yeast, it is believed that this enzyme will exhibit similar qualities, regardless of its source of isolation.

In preferred embodiments, the inventors have isolated the native enzyme from rat brains in that this source is readily available. However, numerous other sources are contemplated to be directly applicable for isolation of the native enzyme, especially mammalian tissues such as liver, and human placenta, and also reticulocytes, or even yeast. Those of skill in the art, in light of the present disclosure, should appreciate that the techniques disclosed herein will be generally applicable to all such farnesyl transferases.

It will also be appreciated that the enzyme may be purified from recombinant cells prepared in accordance with the present invention. The techniques disclosed for the isolation of native farnesyl transferase area believed to be equally applicable to the purification of the protein from recombinant host cells, whether bacterial or eukaryotic, in which DNA segments encoding the selected constituent subunit has been expressed or co-expressed.

After the cell extract is prepared the enzyme is preferably subjected to two partial purification steps prior to affinity chromatography. These steps comprise preliminary treatment with 30% saturated ammonium sulfate which removes certain contaminants by precipitation. This is followed by treatment with 50% saturated ammonium sulfate, which precipitates the farnesyl transferase. The pelleted enzyme is then dissolved in a suitable buffer, such as 20 mM Tris-chloride (pH 7.5) containing 1 mM DTT and 20 $\mu$M $ZnCl_2$, dialyzed against the same buffer, and then subjected to further purification steps.

In preferred embodiments, the dialyzed solution containing the enzyme is applied to a column containing an ion exchange resin such as Mono Q. After washing of the column to remove contaminants, the enzyme is eluted with a gradient of 0.25–1.0M NaCl in the same buffer. The enzyme activity in each fraction is assayed as described below, and the fractions containing active enzyme are pooled and applied to the affinity column described below.

It is, of course, recognized that the preliminary purification steps described above are preferred laboratory procedures that might readily be replaced with other procedures of equivalent effect such as ion exchange chromatography on other resins or gel filtration chromatography. Indeed, it is possible that these steps could even be omitted and the crude cell extract might be carried directly to affinity chromatography.

After the preliminary purification steps, the extract may be subjected to affinity chromatography on an affinity chromatography medium which includes a farnesyl transferase binding peptide coupled to a suitable matrix. Typically, preferred farnesyl transferase binding peptides will comprise a peptide of at least 4 amino acids in length and will include a carboxy terminal sequence of -C-A-A-X, wherein:

C=cysteine;
A=an aliphatic or hydroxy amino acid; and
X=any amino acid.

Preferred binding peptides of the present invention which fall within the above general formula include structures such as -C-V-I-M, -C-S-I-M and -C-A-I-M, all of which structures are found to naturally occur in proteins which are believed to be acted upon by farnesyl protein transferases in nature. Particularly preferred are relatively short peptides, such as on the order of about 4 to about 10 amino acids in length which incorporate one of the foregoing binding sequences. Of particular preference is the peptide T-K-C-V-I-M, which has been effectively employed by the inventors in the isolation of farnesyl protein transferase.

The next step in the overall general purification scheme involves simply washing the medium to remove impurities. That is, after subjecting the extract to affinity chromatography on the affinity matrix, one will desire to wash the matrix in a manner that will remove the impurities while leaving the farnesyl transferase enzyme relatively intact on the medium. A variety of techniques are known in the art for washing matrices such as the one employed herein, and all such washing techniques are intended to be included within the .scope of this invention. Of course, for washing purposes, one will not desire to employ buffers that will release or otherwise alter or denature the enzyme. Thus, one will typically want to employ buffers which contain non-denaturing detergents such as octylglucoside buffers, but will want to avoid buffers containing, e.g., chaotropic reagents which serve to denature proteins, as well as buffers of low pH (e.g., less than 7), or of high ionic strength (e.g., greater than 1.0M), as these buffers tend to elute the bound enzyme from the affinity matrix.

After the matrix-bound enzyme has been sufficiently washed, for example in a medium-ionic strength buffer at essentially neutral pH, the specifically bound material can be eluted from the column by using a similar buffer but of reduced pH (for example, a pH of between about 4 and 5.5). At this pH, the enzyme will typically be found to elute from the preferred affinity matrices disclosed in more detail hereinbelow.

While it is believed that advantages in accordance with the invention can be realized simply through affinity chromatography techniques, additional benefits will be achieved through the application of additional purification techniques, such as gel filtration techniques. For example, the inventors have discovered that Sephacryl S-200 high resolution gel columns can be employed with significant benefit in terms of protein purification. However, the present disclosure is by no means limited to the use of Sephacryl S-200, and it is believed that virtually any type of gel filtration arrangement can be employed with some degree of benefit. For example, one may wish to use techniques such as gel filtration, employing media such as Superose, Agarose, or even Sephadex.

Through the application of various of the foregoing approaches, the inventors have successfully achieved farnesyl transferase enzyme compositions of relatively high specific activity, measured in terms of ability to transfer farnesol from all-trans farnesyl pyrophosphate. For the purposes of the present invention, one unit of activity is defined as the amount of enzyme that transfers 1 pmol of farnesol from all-trans farnesyl pyrophosphate (FPP) into acid-precipitable $p21^{H\text{-}ras}$ per hour under the conditions set forth in the Examples. Thus, in preferred embodiments the present invention is concerned with compositions of farnesyl transferase which include a specific activity of between about 5 and about 10 units/mg of protein. In more preferred embodiments, the present invention is concerned with compositions which exhibit a farnesyl transferase specific activity of between about 500 and about 600,000 units/mg of protein. Thus, in terms of the unit definition set forth above, the inventors have been able to achieve compositions having a specific activity of up to about 600,000 units/mg using techniques disclosed herein.

Cloning of Farnesyl:Protein Transferase Subunits

Important aspects of the present invention concern isolated DNA segments and recombinant vectors encoding the $\alpha$ and $\beta$ subunits of mammalian farnesyl:-protein transferase, and the creation of recombinant host cells through the application of DNA technology, which express one, or preferably both, of these polypeptides.

As used herein, the term "DNA segment" in intended to refer to a DNA molecule which has been isolated free of total genomic DNA of a particular species. Therefore, a DNA segment encoding a subunit of farnesyl:protein transferase is intended to refer to a DNA segment which contains such coding sequences yet is isolated away from total genomic DNA of the species from which the DNA is obtained. Included within the term "DNA segment", are DNA segments which may be employed in the preparation of vectors, as well as the vectors themselves, including, for example, plasmids, cosmids, phage, viruses, and the like.

In particular embodiments, the invention concerns isolated DNA segments and recombinant vectors incorporating DNA sequences which encode a farnesyl:-protein transferase subunit that includes within its amino acid sequence the amino acid sequence of seq id no:1 or seq id no:3, corresponding to rat brain farnesyl transferase subunits $\alpha$ and $\beta$, respectively. Moreover, in other particular embodiments, the invention concerns isolated DNA segments and recombinant vectors incorporating DNA sequences which encode a farnesyl:-protein transferase subunit that includes within its amino acid sequence the amino acid sequence of seq id no:5 or seq id no:7, corresponding to human farnesyl transferase subunits $\alpha$ and $\beta$, respectively. Recombinant vectors and isolated segments may therefore variously include the $\alpha$ or $\beta$ subunit coding regions themselves, coding regions bearing selected alterations or modifications in the basic coding region or may encode larger polypeptides which nevertheless include sequences which will confer farnesyl transferase activity when said polypeptide is combined with the alternate subunit.

However, it will be understood that this aspect of the invention is not limited to the particular nucleic acid and amino acid sequences of seq id no:1 and no:2 and seq id no:5 and no:6 ($\alpha$ subnit) or seq id no:3 and no:4 and seq id no:7 and 8 ($\beta$ subunit). Accordingly, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

The recombinant cloning of cDNAs encoding the farnesyl transferase $\alpha$ and $\beta$ subunits was achieved through the use of the peptide sequence information set forth above which was used in the preparation of subunit-specific oligonucleotides. Such oligonucleotides could be employed in the direct hybridization screening of a clone bank. However, the inventors preferred to use the peptide sequences in the preparation of primers for use in PCR amplification and partial sequencing of the selected subunit gene to confirm the underlying DNA sequence, and to prepare longer and more specific probes for use in clone bank screening.

In screening for the farnesyl transferase subunit-specific sequences, the inventors chose to use a cDNA clone bank prepared from poly A+ RNA. However, it is believed that the type of clone bank used is not crucial and that, if desired, one could employ a genomic clone bank. Similarly, in that the farnesyl transferase enzyme appears to be fairly ubiquitous in nature, it is believed that virtually any eukaryotic cell source may be employed for the preparation of RNA from which the clone bank is to be generated. One may mention by way of example, yeast, mammalian, plant, eukaryotic parasites and even viral-infected types of cells as the source of starting poly A+ RNA.

As the protein was initially purified from a mammalian source (rat), it is Contemplated that particular advantages may be found in the use of mammalian cells, such as rat or human cell lines, as an RNA source. One may, of course, wish to first test such a cell line to ensure that relatively high levels of the farnesyl transferase enzyme are being produced by the selected cells. Rat brain, PC12 (a rat adrenal tumor cell line) and KNRK (a newborn rat kindney cell line) were preferred by the present inventors as they exhibited high levels of endogenous farnesyl:protein transferase activity.

The type of cDNA clone bank used in the screening procedure is not believed to be particularly critical. However, one will likely find particular benefit through the preparation and use of a phage-based bank, such as λgt10 or λgt11, preferably using a particle packaging system. Phage-based cDNA banks are preferred because of the large numbers of recombinants that may be prepared and screened will relative ease. The manner in which the cDNA itself is prepared is again not believed to be particularly crucial. However, the inventors successfully employed both oligo dT and randomly primed cDNA, from a consideration of the difficulties which may arise in the reverse transcription of a large mRNA molecule.

Once a clone bank has been prepared, it may be screened in a number of fashions. For example, as mentioned above, one could employ the subunit peptide sequences set forth above for the preparation of nucleotide probes with which to directly screen the clone bank. A more preferrable approach was found to be to use such sequences in the preparation of primers which may were used in PCR-based reactions to amplify and then sequence portions of the selected subunit gene, to thereby confirm the actual underlying DNA sequence, and to prepare longer and more specific probes for further screening. These primers may also be employed for the preparation of cDNA clone banks which are enriched for 3' and/or 5' sequences. This may be important, e.g., where less than a full length clone is obtained through the initially prepared bank.

If a less than full length clone was obtained on initial screening, the entire sequence could be subsequently obtained through the application of 5' and/or 3' extension technology, as required. The techniques for obtaining an extended farnesyl transferase subunit clone will be known to those of skill in the art in light of the present disclosure. The procedures used are those described in Frohman et al. (34), involving a combination of reverse transcription, tailing with terminal deoxytransferase and, finally, PCR.

It is proposed that the DNA segments of the present invention may be employed for a variety of applications. For example, a particularly useful application concerns the recombinant production of the individual subunits or proteins or peptides whose structure is derived from that of the subunits, or in the recombinant production of the holoenzyme following co-expression of the two subunits. Additionally, the farnesyl transferase-encoding DNA segments of the present invention can also be used in the preparation of nucleic acid probes or primers, which can, for example, be used in the identification and cloning of farnesyl transferase genes or related genomic sequences, or in the study of subunit(s) expression, and the like.

Expression of Farnesyl:Protein Transferase Subunits

Turning firstly to the expression of the cloned subunits. Once a suitable (full length if desired) clone or clones have been obtained, whether they be cDNA based or genomic, one may proceed to prepare an expression system for the recombinant preparation of one, or preferably both, of the subunits. The engineering of DNA segment(s) for expression in a prokaryotic or eukaryotic system may be performed by techniques generally known to those of skill in recombinant expression. It is believed that virtually any expression system may be employed in the expression of either or both subunits. Both subunits of the enzyme have been successfully co-expressed in eukaryotic expression systems with the production of active enzyme, but it is envisioned that bacterial expression systems may ultimately be preferred for the preparation of farnesyl transferase for all purposes. The cDNAs for both subunits have been separately expressed in bacterial systems, with the encoded proteins being expressed as fusions with *Schistosoma japonicum* glutathione S-transferase. It is believed that bacterial expression will ultimately have numerous advantages over eukaryotic expression in terms of ease of use and quantity of materials obtained thereby. Furthermore, it is proposed that co-transformation of host cells with DNA segments encoding both the α and β subunits will provide a convenient means for obtaining active enzyme. However, separate expression followed by reconstitution is also certainly within the scope of the invention. Both cDNA and genomic sequences are suitable for eukaryotic expression, as the host cell will, of course, process the genomic transcripts to yield functional mRNA for translation into protein.

It is similarly believed that almost any eukaryotic expression system may be utilized for the expression of either, or preferably, both of the farnesyl transferase subunits, e.g., baculovirus-based, glutamine synthase-based or dihydrofolate reductase-based systems could be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use. For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the enzyme, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

As noted above, it is proposed that in embodiments concerning the production of farnesyl transferase enzyme, the α and β subunits may be co-expressed in the same cell. This may be achieved by co-transfecting the cell with two distinct recombinant vectors, each bearing a copy of either the α or β-encoding DNA. Alternatively, a single recombinant vector may be constructed to include the coding regions for both of the subunits, which could then be expressed in cells transfected with the single vector. In either event, the term "co-expression" herein refers to the expression of both the α and β subunits of farnesyl transferase in the same recombinant cell.

It is contemplated that virtually any of the commonly employed host cells can be used in connection with the expression of one, or preferably both, of the farnesyl transferase subunits in accordance herewith. Examples include cell lines typically employed for eukaryotic expression such as 239, AtT-20, HepG2, VERO, HeLa, CHO, WI 38, BHK, COS-7, RIN and MDCK cell lines. A preferred line for use in eukaryotic expression embodiments of the present invention has been found to be the human embryonic kidney cell line, 293.

In accordance with the general guidelines described above, a preferred method for expressing farnesyl transferase DNA has been found to be the transfection of human embryonic kidney 293 cells with expression vectors termed pFT-α or pFT-β. The pFT expression vectors are constructed from pCMV5, a plasmid that contains the promoter-enhancer region of the major immediate early gene of human cytomegalovirus (38).

Nucleic Acid Hybridization

The DNA sequences disclosed herein will also find utility as probes or primers in nucleic acid hybridization embodiments. As such, it is contemplated that oligonucleotide fragments corresponding to the sequences of seq id no:2, seq id no:4, seq id no:6 and seq id no:8 for stretches of between about 10 nucleotides to about 30 nucleotides will find particular utility, with even longer sequences, e.g., 40, 50, 60, even up to full length, being even more particularly preferred. The ability of such nucleic acid probes to specifically hybridize to farnesyl transferase subunit-encoding sequences will enable them to be of use in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of farnesyl transferase genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M-0.15M NaCl at temperatures of 50° C. to 70° C. Such selective conditions tolerate little, if any, mismatch between the probe and the template or target strand, and would be particularly suitable for isolating farnesyl transferase genes.

Of course, for some applications, for example, where one desires to prepare mutants employing a mutant primer strand hybridized to an underlying template or where one seeks to isolate farnesyl transferase-encoding sequences for related species, functional equivalents, or the like, less stringent hybridization conditions will typically be needed in order to allow formation of the heteroduplex. In these circumstances, one may desire to employ conditions such as 0.15M-0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one will likely desire to employ an enzyme tag such a urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Biological Functional Equivalent Amino Acids

As mentioned above, modification and changes may be made in the structure of the farnesyl transferase subunits and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even counterveiling properties (e.g., antagonistic v. agonistic). It is thus contemplated by the inventors that various changes may be made in the sequence of the peptides (or underlying DNA) without appreciable loss of their biological utility or activity.

In making such changes, the hydropathic index of amino acids may be considered. The importance of the hydropathic amino acid index, i.e. hydrophobicity and charge characteristics, in conferring interactive biologic function on a protein is generally understood in the art (43). For example, it is known that certain amino acids may be substituted for other amino acids having a similar hydropathic index or score and still retain a similar biological activity. It is believed that the relative hydropathic character of the amino acid determines the secondary structure of the resultant protein, which in turn defines the interaction of the protein with substrate molecules. Thus, for example, it is proposed the isoleucine, which has a hydrophatic index of +4.5, can be substituted for valine (+4.2) or leucine (+3.8), and still obtain a protein having similar biologic activity. Alternatively, at the other end of the scale, it is proposed that lysine (−3.9) can be substituted for arginine (−4.5), and so on.

Amino acid substitutions are generally therefore based on the relative similarity of the side-chain substituents, for example, size, electrophilic character, charge, and the like. Exemplary substitutions which take various of the foregoing characteristics into consideration are well known to those of skill in the art and include: alanine, glycine and serine; arginine-and lysine; glutamate and aspartate; serine and threonine; and valine, leucine and isoleucine.

Inhibitors of Farnesyl:Protein Transferase

Of principal importance to the present invention is the discovery that proteins or peptides which incorporate a farnesyl acceptor sequence, such as one of the farnesyl acceptor sequences discussed above, function as inhibitors of farnesyl:protein transferase, and therefore may serve as a basis for anticancer therapy. In particular, it has been found that farnesyl acceptor peptides can successfully function both as false substrates that serve to inhibit the farnesylation of natural substrates such as $p21^{ras}$, and as direct inhibitors which are not themselves farnesylated. Compounds falling into the latter category are particularly important in that these compounds are "pure" inhibitors that are not consumed by the inhibition reaction and can continue to function as inhibitors. Both types of compounds constitute an extremely important aspect of the invention in that they provide a means for blocking farnesylation of $p21^{ras}$ proteins, for example, in an affected cell system.

The farnesyl transferase inhibitor embodiments of the present invention concern in a broad sense a peptide or protein other than $p21^{ras}$ proteins, lamina or lamin b, or yeast mating factor a, which peptide or protein includes a farnesyl acceptor sequence within its structure and is further capable of inhibiting the farnesylation of $p21^{ras}$ by farnesyl transferase.

In preferred embodiments, the farnesyl transferase inhibitor of the present invention will include a farnesyl acceptor or inhibitory amino acid sequence having the amino acids -C-A-A-X, wherein:

C=cysteine;
A=any aliphatic, aromatic or hydroxy amino acid; and
X=any amino acid.

Typically, the farnesyl acceptor or inhibitory amino acid sequence will be positioned at the carboxy terminus of the protein or peptide such that the cysteine residue is in the fourth position from the carboxy terminus.

In preferred embodiments, the inhibitor will be a relatively short peptide such as a peptide from about 4 to about 10 amino acids in length. To date, the most preferred inhibitor tested is a tetrapeptide which incorporates the above-mentioned C-A-A-X recognition structure. It is possible that even shorter peptides will ultimately be preferred for practice of the invention in that the shorter the peptide, the greater the uptake by such peptide by biological systems, and the reduced likelihood that such a peptide will be destroyed or otherwise rendered biologically ineffective prior to effecting inhibition. However, numerous suitable inhibitory peptides have been prepared and tested by the present inventors, and shown to inhibit enzymatic activities virtually completely, at reasonable concentrations, e.g., between about 1 and 3 $\mu$M (with 50% inhibitions on the order of 0.1 to 0.5 $\mu$M).

While, broadly speaking, it is believed that compounds exhibiting an $IC_{50}$ of between about 0.01 $\mu$M and 10 $\mu$M will have some utility as farnesyl transferase inhibitors, the more preferred compounds will exhibit an $IC_{50}$ of between 0.01 $\mu$M and 1 $\mu$M. The most preferred compounds will generally have an $IC_{50}$ of between about 0.01 $\mu$M and 0.3 $\mu$M.

Exemplary peptides which have been prepared, tested and shown to inhibit farnesyl transferase at an $IC_{50}$ of between 0.01 and 10 $\mu$M include CVIM; KKSKTKCVIM; TKCVIM; RASNRSCAIM; TQSPQNCSIM; CIIM; CVVM; CVLS; CVLM; CAIM; CSIM; CCVQ; CIIC; CIIS; CVIS; CVLS; CVIA; CVIL; CLIL; CLLL; CTVA; CVAM; CKIM; CLIM; CVLM; CFIM; CVFM; CVIF; CEIM; CGIM; CPIM; CVYM; CVTM; CVPM; CVSM; CVIF; CVIV; CVIP; CVII.

A variety of peptides have been synthesized and tested such that now the inventors can point out peptide sequences having particularly high inhibitory activity, i.e., wherein relatively lower concentrations of the peptides will exhibit an equivalent inhibitory activity ($IC_{50}$). Interestingly, it has been found that slight changes in the sequence of the acceptor site can result in loss of inhibitory activity. Thus, when TKCVIM is changed to TKVCIM, the inhibitory activity of the peptide is reversed. Similarly, when a glycine is substituted for one of the aliphatic amino acids in CAAX, a decrease in inhibitory activity is observed. However, it is proposed that as long as the general formula as discussed above is observed, one will achieve a structure that is inhibitory to farnesyl transferase.

A particularly important discovery is the finding that the incorporation of an aromatic residue such as phenylalanine, tyrosine or tryptophan into the third position of the CAAX sequence will result in a "pure" inhibitor. As used herein, a "pure" farnesyl:protein transferase inhibitor is intended to refer to one which does not in itself act as a substrate for farnesylation by the enzyme. This is particularly important in that the inhibitor is not consumed by the inhibition process, leaving the inhibitor to continue its inhibitory function unabated. Exemplary compounds which have been tested and found to act as pure inhibitors include CVFM, CVWM, CVYM, CIFM, CV(pCl-F)M, L-penicillamine-VFM, and L-penicillamine-VIM. Pure inhibitors will therefore incorporate an inhibitory amino acid sequence rather than an acceptor sequence, with the inhibitory sequence characterized generally as having an aromatic moiety associated with the penultimate carboxy terminal amino acid, whether it be an aromatic amino acid or another amino acid which has been modified to incorporate an aromatic structure. (see Goldstein et al., ref. 53)

Importantly, the pure inhibitor CVFM is the best inhibitor identified to date by the inventors. It should be noted that the related peptide, CFIM is not a "pure" inhibitor; its inhibitory activity is due to its action as a substrate for farnesylation.

The potency of CVFM peptides as inhibitors of the enzyme may be enhanced by attaching substituents such as fluoro, chloro or nitro derivatives to the phenyl ring. An example is parachlorophenylalanine, which has been tested and found to have "pure" inhibitory activity. It may also be possible to substitute more complex hydrophobic substances for the phenyl group of phenylalanine. These would include naphthyl ring systems.

The present inventors propose that additional improvements can be made in pharmaceutical embodiments of the inhibitor by including within their structure moieties which will improve their hydrophobicity, which it is proposed will improve the uptake of peptidyl structures by cells. Thus, in certain embodiments, it is proposed to add fatty acid or polyisoprenoid side chains to the inhibitor which, it is believed, will improve their lipophilic nature and enhance their cellular uptake.

Other possible structural modifications include the addition of benzyl, phenyl or acyl groups to the amino acid structures, preferably at a position sufficiently removed from the farnesyl acceptor site, such as at the amino terminus of the peptides. It is proposed that such structures will serve to improve lypophilicity. In this regard, the inventors have found that N-acetylated and N-octylated peptides such as modified CVIM retain much of their inhibitory activity, whereas S-acetoamidated CVIM appears to lose much of its inhibitory activity.

The invention also contemplates that modifications can be made in the structure of inhibitory proteins or peptides to increase their stability within the body, such as modifications that will reduce or eliminate their susceptibility to degradation, e.g., by proteases. For example, the inventors contemplate that useful structural modifications will include the use of amino acids which are less likely to be recognized and cleaved by proteases, such as the incorporation of D-amino acids, or amino acids not normally found in proteins such as ornithine or taurine. Other possible modifications include the cyclization of the peptide, derivatization of the NH groups of the peptide bonds with acyl groups, etc.

Assays For Farnesyl:Protein Transferase

In still further embodiments, the invention concerns a method for assaying farnesyl transferase activity in a composition. This is an important aspect of the invention in that such an assay system provides one with not only the ability to follow the isolation and purification of native or recombinant farnesyl transferase enzymes, but it also forms the basis for developing a screening assay for candidate inhibitors of the enzyme, discussed in more detail below. The assay method generally includes determining the ability of a composition suspected of having farnesyl transferase activity to catalyze the transfer of farnesol to an acceptor protein or peptide. As noted above, a farnesyl acceptor protein or peptide is generally defined as a protein or peptide which will act as a substrate for farnesyl transferase and which includes a recognition site such as -C-A-A-X, as defined above.

Typically, the assay protocol is carried out using all-trans farnesyl pyrophosphate as the farnesol donor in the reaction. Thus, one will find particular benefit in constructing an assay wherein a label is present on the farnesyl moiety of all-trans farnesyl pyrophosphate, in that one can measure the appearance of such a label, for example, a radioactive label, in the farnesyl acceptor protein or peptide.

As with the characterization of the enzyme discussed above, the farnesyl acceptor sequence which are employed in connection with the assay can be generally defined by -C-A-A-X, with preferred embodiments including sequences such as -C-V-I-M, -C-S-I-M, -C-A-I-M, etc., all of which have been found to serve as useful enzyme substrates. It is believed that most proteins or peptides that include a carboxy terminal sequence of -C-A-A-X can be successfully employed in farnesyl protein transferase assays. For use in the assay a preferred farnesyl acceptor protein or peptide will be a $p21^{ras}$ protein. This is particularly true where one seeks to identify inhibitor substances, as discussed in more detail below, which function either as "false acceptors" in that they divert farnesylation away from natural substrates by acting as substrates in and or themselves, or as "pure" inhibitors which are not in themselves farnesylated. The advantage of employing a natural substrate such as $p21^{ras}$ is several fold, but includes the ability to separate the natural substrate from the false substrate to analyze the relative degrees of farnesylation.

However, for the purposes of simply assaying enzyme specific activity, e.g., assays which do not necessarily involve differential labeling or inhibition studies, one can readily employ short peptides as a farnesyl acceptor in such protocols, such as peptides from about 4 to about 10 amino acids in length which incorporate the recognition signal at their carboxy terminus. Exemplary farnesyl acceptor protein or peptides include but are not limited to CVIM; KKSKTKCVIM; TKCVIM; RASNRSCAIM; TQSPQNCSIM; CIIM; CVVM; and CVLS.

Assays for Candidate Substances

In still further embodiments, the present invention concerns a method for identifying new farnesyl transferase inhibitory compounds, which may be termed as "candidate substances." It is contemplated that this screening technique will prove useful in the general identification of any compound that will serve the purpose of inhibiting farnesyl transferase. It is further contemplated that useful compounds in this regard will in no way be limited to proteinaceous or peptidyl compounds. In fact, it may prove to be the case that the most useful pharmacologic compounds for identification through application of the screening assay will be non-peptidyl in nature and, e.g., which will be recognized and bound by the enzyme, and serve to inactivate the enzyme through a tight binding or other chemical interaction.

Thus, in these embodiments, the present invention is directed to a method for determining the ability of a candidate substance to inhibit a farnesyl transferase enzyme, the method including generally the steps of:

(a) obtaining an enzyme composition comprising a farnesyl transferase enzyme that is capable of transferring a farnesyl moiety to a farnesyl acceptor substance;

(b) admixing a candidate substance with the enzyme composition; and (c) determining the ability of the farnesyl transferase enzyme to transfer a farnesyl moiety to a farnesyl acceptor substrate in the presence of the candidate substance.

An important aspect of the candidate substance screening assay hereof is the ability to prepare a native or recombinant farnesyl transferase enzyme composition in a relative purified form, for example, in a manner as discussed above. This is an important aspect of the candidate substance screening assay in that without at least a relatively purified preparation, one will not be able to assay specifically for enzyme inhibition, as opposed to the effects of the inhibition upon other substances in the extract which then might affect the enzyme. In any event, the successful isolation of the farnesyl transferase enzyme now allows for the first time the ability to identify new compounds which can be used for inhibiting this cancer-related enzyme.

The candidate screening assay is quite simple to set up and perform, and is related in many ways to the assay discussed above for determining enzyme activity. Thus, after obtaining a relatively purified preparation of the enzyme, either from native or recombinant sources, one will desire to simply admix a candidate substance with the enzyme preparation, preferably under conditions which would allow the enzyme to perform its farnesyl transferase function but for inclusion of a inhibitory substance. Thus, for example, one will typically desire to include within the admixture an amount of a known farnesyl acceptor substrate such as a $p21^{ras}$ protein. In this fashion, one can measure the ability of the candidate substance to reduce farnesylation of the farnesyl acceptor substrate relatively in the presence of the candidate substance.

Accordingly, one will desire to measure or otherwise determine the activity of the relatively purified enzyme in the absence of the added candidate substance relative to the activity in the presence of the candidate substance in order to assess the relative inhibitory capability of the candidate substance.

Methods of Inhibiting Farnesyl:protein Transferase

In still further embodiments, the present invention is concerned with a method of inhibiting a farnesyl transferase enzyme which includes subjecting the enzyme to an effective concentration of a farnesyl transferase inhibitor such as one of the family of peptidyl compounds discussed above, or with a candidate substance identified in accordance with the candidate screening assay embodiments. This is, of course, an important aspect of the invention in that it is believed that by inhibiting the farnesyl transferase enzyme, one will be enabled to treat various aspects of cancers, such as ras-related cancers. It is believed that the use of such inhibitors to block the attachment of farnesyl groups to ras proteins in malignant cells of patients suffering with cancer or pre-cancerous states will serve to treat or palliate the cancer, and may be useful by themselves or in conjunction with other cancer therapies, including chemotherapy, resection, radiation therapy, and the like.

BRIEF DESCRIPTION OF THE DRAWINGS

FIG. 1 A,B. Transfer of Farnesol from [$^3$H]FPP to $p21^{H\text{-}ras}$ by Partially Purified Rat Brain Farnesyl:Protein Transferase.

FIG. 2A,B. Substrate Saturation Curves for Farnesyl:Protein Transferase. FIG. 2A: each standard reaction mixture contained 1.8 µg of partially purified farnesyl transferase, 40 µg $p21^{H\text{-}ras}$, [$^3$H]FPP (250,000 dpm); and varying amounts of unlabeled FPP to give the indicated final concentration of [$^3$H]FPP. FIG. 2B: each standard reaction mixture contained 3.2 µg partially purified farnesyl transferase, 10 pmol [$^3$H]FPP, and the indicated concentration of $p21^{H\text{-}ras}$ that had been incubated with 50 µM of the indicated nucleotide for 45 min at 30° C. and then passed through a G-50 Sephadex gel filtration column at room temperature in buffer containing 10 mM Tris-chloride (pH 7.7), 1 mM EDTA, 1 mM DTT, and 3 mMMgCl$_2$. For both panels, assays were carried out in duplicate for 1 hour at 37° C., and TCA-precipitable radioactivity was measured as described in the Example.

FIG. 3. Divalent Cation Requirement for Farnesyl:Protein Transferase. Each standard reaction mixture contained 10 pmol [$^3$H]FPP, 2.5 µg of partially purified farnesyl transferase, 40 µM $p21^{H\text{-}ras}$, 0.15 mM EDTA, and the indicated concentrations of either ZnCl$_2$ ● or MgCl$_2$ ▲. Incubations were carried out in duplicate for 1 hour at 37° C., and TCA-precipitable radioactivity was measured as described in the Examples.

FIG. 4A: an aliquot from a standard reaction mixture was subjected to cleavage with methyl iodide as described in the Examples.

FIG. 7A, a 6-μl aliquot of each fraction was assayed for farnesyl:protein transferase activity by the standard method except that each reaction mixture contained 0.2% octyl-β-D-glucopyranoside. The column was calibrated with thyroglobulin (670 kDa), γ-globulin (158 kDa), ovalbumin (44 kDa), myoglobin (17 kDa), and vitamin B12 (1.35 kDa). Arrows indicate the elution position of the 158-kDa and 44-kDa markers.

FIG. 12A: Each reaction mixture contained 15 pmol [$^3$H]FPP, 4.5 or 6 ng of purified farnesyl:protein transferase, 40 μM p21$^{H\text{-}ras}$, and the indicated concentration of competitor tetrapeptide. After incubation for 30 min at 37° C., the amount of [$^3$H]farnesyl transferred to p21$^{H\text{-}ras}$ was measured by the standard filter assay. Values shown are the average of two experiments. The "100% of control" values were 16 and 19 nmol min$^{-1}$ mg protein$^{-1}$.

FIG. 16A, B. cDNA Probes Generated from a Knowledge of the Amino Acid Sequences of Peptides Derived from Rat Farnesyl Transferase α and β Subunits. FIG 16A: Primer α1 and Primer α2 were used in PCR with rat genomic DNA to obtain the the nucletide sequence encoding the amino acid sequence of the peptide shown, as described in Example III. The nucleotide sequence 5'-ATIGAGTTAAACGCAGCCAAC-TATACGGTCTGGCACTT-3' was used as a probe to screen a rat brain cDNA library. FIG. 16B (lower): Nucleotide sequence encoding the peptide as derived from the above PCR. Primer β3 and primer β4 were synthesized and used as the primers for 3-end amplification of the cDNA, as described in Example III.

FIG. 17. Comparison of the Amino Acid Sequences of Rat Farnesyl Transferase e-Subunit (FT-α) and Yeast RAM2. Amino acid residues are numbered on the left. Identical amino acids are boxed. The sequence of yeast RAM2 was reported by He et al. (51).

FIG. 18. Comparison of the Amino Acid Sequences of Rat Farnesyl Transferase β-Subunit (FT-β) and Yeast DPR1/RAM1. Amino acid residues are numbered on the left. Identical amino acids are boxed. The sequence of yeast DPR1/RAM1 was reported by Goodman et al. (42).

FIGS 19A & 19C: Total RNA was isolated from the indicated rat tissues, and an aliquot (30 μg) was subjected to electrophoresis on a 1.5% agarose gel and blotted onto a nylon membrane for blot analysis. Hybridization was carried out at 42° C. for 20 hours with a mixture of two single-stranded uniformly 32P-labeled cDNA probes, specific for either the α subunit (A) or β subunit (B) of rat farnesyl transferase. Each probe was ~500 nucleotides in length and was used at $2 \times 10^6$ cpm/ml. The filters were washed in $0.2 \times SSC$ containing 0.2% (w/v) SDS at 68° C. for 1 hour, then exposed to Kodak XAR-5 film for 2-4 days at -70° C. The positions of RNA standards run in adjacent lanes are indicated on the left. As a loading control, the same filter was reprobed initially with a 32P-labeled 49-mer oligonucleotide corresponding to rat cyclophilin cDNA ($2 \times 10^6$ cpm/ml) and subsequently with a uniformly 32p-labeled cDNA (~1.2 kb) for rat glyceraldehyde-3-phosphate dehydrogenase (GAPDH) ($4 \times 10^6$ cpm/ml). After each washing, the reprobed filter was exposed for 12 hours at -70° C.

DETAILED DESCRIPTION OF THE PREFERRED EMBODIMENTS

Figure 1A:
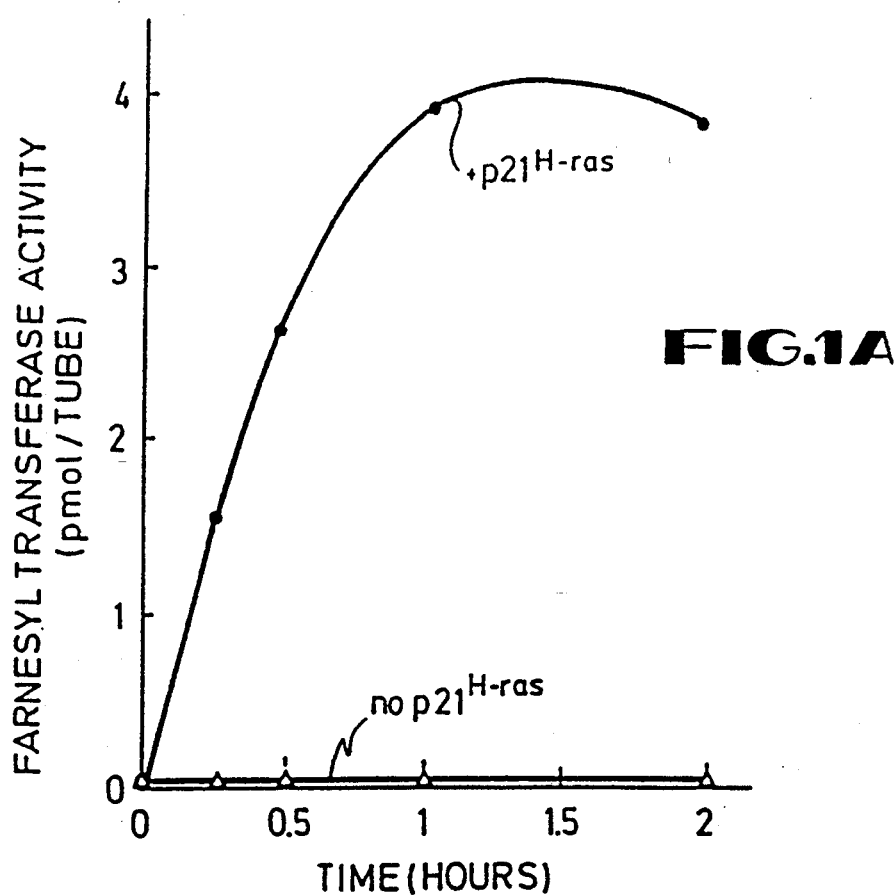
FIG. 1A Each standard assay mixture contained 10 pmoles of [$^3$H]FPP and 3.5 µg of partially purified farnesyl transferase in the absence ▲ or presence ● of 40 µM $p21^{H\text{-}ras}$. Duplicate samples were incubated for the indicated time at 37° C., and TCA-precipitable radioactivity was measured as described in the Examples.

The following examples illustrate techniques discovered by the inventors for the identification and purification of mammalian farnesyl protein transferase enzymes, as well as techniques for their assay and for the screening of new compounds which may be employed to inhibit such enzymes. These studies also demonstrate a variety of peptidyl compounds which themselves can be employed to inhibit these enzymes. It should be appreciated by those of skill in the art that the techniques disclosed in the examples which follow represent laboratory techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

PREPARATION AND CHARACTERIZATION OF FARNESYL: PROTEIN TRANSFERASE

1. Materials

Peptides were obtained from Peninsula Laboratories or otherwise synthesized by standard techniques. All peptides were purified on HPLC, and their identity was confirmed by amino acid analysis. Just prior to use, each peptide was dissolved at a concentration of 0.8 SmM in 10 mM dithiothreitol (DTT), and all dilutions were made in 10 mM DTT. Unlabeled all-trans farnesyl pyrophosphate (FPP) was synthesized by the method of Davisson, et al. (13). [1-$^3H$]Farnesyl pyrophosphate (20 Ci/mmol) was custom synthesized by New England Nuclear. Geraniol and farnesol (both all-trans) were obtained from Aldrich Chemical. All-trans geranylgeraniol was a gift of R. Coates (University of Illinois).

Recombinant wild type human p21$^{H\text{-}ras}$ protein was produced in a bacterial expression system with pATrasH (provided by Channing J. Der, La Jolla Cancer Research Foundation, La Jolla, Calif.), an expression vector based on pXVR (14). The plasmid was transformed into *E. coli* JM105, and the recombinant p21$^{H\text{-}ras}$ protein was purified at 4° C. from a high speed supernatant of the bacterial extracts by sequential chromatography on DEAE-Sephacel and Sephadex G-75. Purity was ~90% as judged by Coomassie blue staining of SDS gels. Purified p21$^{H\text{-}ras}$ was concentrated to 15 mg/ml in 10 mM Tris-chloride (pH 7.5) containing 1 mM DTT, 1 mM EDTA, 3 mM MgCl$_2$, and 30 μM GDP and stored in multiple aliquots at −70° C.

2. Assay for Farnesyl:Protein Transferase Activity

Farnesyl:protein transferase activity was determined by measuring the amount of 3H-farnesol transferred from all-trans $^3$H]farnesyl pyrophosphate ([$^3$H]FPP) to p21$^{H\text{-}ras}$ protein. The standard reaction mixture contained the following concentrations of components in a final volume of 25 μl: 50 mM Tris-chloride (pH 7.5) 50 μM ZnCl$_2$, 20 mM KCl, 1 mM DTT, and 40 μM p21$^{H\text{-}ras}$. The mixture also contained 10 pmoles of [$^3$H]FPP (~30,000 dpm/pmol) and 1.8–3.5 μg of partially purified farnesyl:protein transferase (see below). After incubation for 1 hour at 37° C. in 12×75-mm borosilicate tubes, the reaction was stopped by addition of 0.5 ml of 4% SDS and then 0.5 ml of 30% trichloroacetic acid (TCA).

The tubes were vortexed and left on ice for 45–60 min, after which 2 ml of a 6% TCA/2% SDS solution were added. The mixture was filtered on a 2.5-cm glass fiber filter with a Hoefer filtration unit (FH 225). The tubes were rinsed twice with 2 ml of the same solution, and each filter was washed five times with 2 ml of 6% TCA, dried, and counted in a scintillation counter. One unit of activity is defined as the amount of enzyme that transfers 1pmol of [$^3$H]farnesol from [$^3$H]FPP into acid-precipitable p21$^{H\text{-}ras}$ per hour under the standard conditions.

3. Purification of [Farnesyl:Protein Transferase

All steps were carried out at 4° C. except where indicated:

Step 1—Ammonium Sulfate Fractionation:

Brains from 50 male Sprague-Dawley rats (100–150 g) were homogenized in 100 ml of ice-cold buffer containing 50 mM Tris-chloride (pH 7.5), 1 mM EDTA, 1 mM EGTA, 0.2 mM phenylmethylsulfonyl fluoride (PMSF), and 0.1 mM leupeptin, and the extract was spun at 60,000×g for 70 min. The supernatant was brought to 30% saturation with solid ammonium sulfate, stirred for 30 min on ice, and centrifuged at 12,000×g for 10 min to remove precipitated proteins. The resulting supernatant was adjusted to 50% saturation with ammonium sulfate, and the resulting pellet was dissolved in ~20 ml of 20 mM Tris-chloride (pH 7.5) containing 1 mM DTT and 20 μM ZnCl$_2$ and dialyzed for 4 hours against 4 liters of the same buffer and then 4 liters of fresh buffer of the same composition for 12 hours. The dialyzed material was divided into multiple aliquots and stored at −70° C.

Step 2—Ion-exchange Chromatography:

A portion of the 30–50% ammonium sulfate fraction (200mg protein) was chromatographed on a Mono Q 10/10 column using an FPLC system (Pharmacia LKB Biotechnology). The column was run as described in the legend to FIG. 5. Fractions eluting between 0.3 and 0.4M NaCl contained the majority of the transferase activity. These fractions were pooled, divided into multiple aliquots, and stored at −70° C.

Step 3—Affinity Chromatography: An affinity column containing a peptide corresponding to the COOH-terminal six amino acids of p21$^{K\text{-}ras\text{-}B}$ protein was prepared as follows. Fifteen mg of the peptide TKCVIM were coupled to 1 g of activated CH-Sepharose 4B (Pharmacia LKB Biotechnology) according to the manufacturer's instructions. The resulting 2.5-ml slurry was poured into a column, and excess uncoupled peptide was removed by 10 cycles of alternating washes, each consisting of 40 column volumes of 0.1M sodium acetate (pH 4.0) and then 0.1M Tris-chloride (pH 8.0). Both buffers contained 1M NaCl and 10 mM DTT. The column was stored at 4° C. in 20 mM Tris-chloride (pH 7.2) and 0.02% sodium azide. Fifteen mg of Mono Q-purified material in 10 ml were applied to a 1-ml peptide column equilibrated in 50 mM Tris-chloride (pH 7.5) containing 0.1M NaCl and 1 mM DTT (Buffer A). The enzyme-containing solution was cycled through the column three times at room temperature. The column was washed with 20 ml of Buffer A containing 0.2% (w/v) octyl-β-D-glucopyranoside (Buffer B). The enzyme was eluted with 20 ml of 50 mM Tris-succinate (pH 5.0) containing 1 mM DTT, 0.1M NaCl, and 0.2% octyl-β-D-glucopyranoside. The pH 5 eluate was concentrated and washed twice with a 10-fold excess of Buffer B in a CF25 Centriflo ultrafiltration cone (Amicon) and brought to 1ml (10-fold concentration relative to the starting material).

Figure 7A:
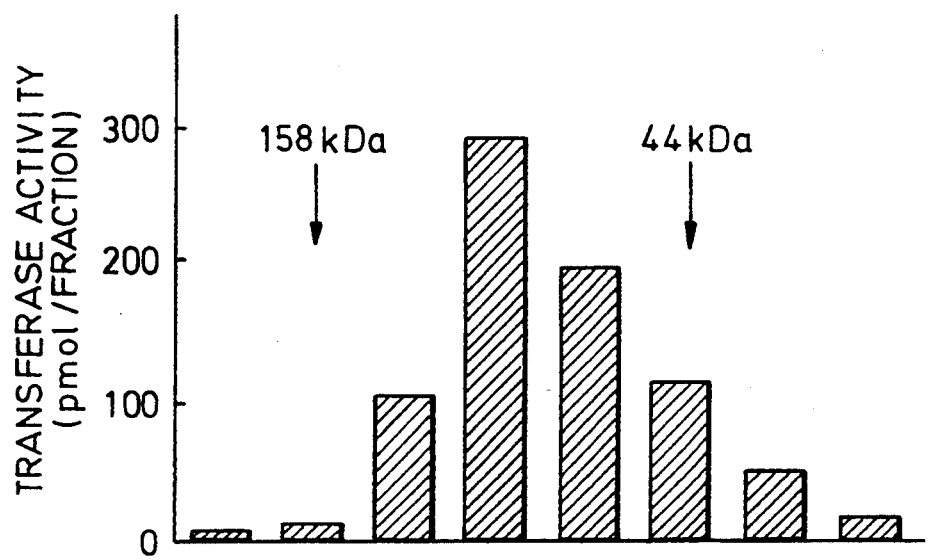
FIG. 7A,B. Gel Filtration of Farnesyl:Protein Transferase. Affinity-purified farnesyl transferase (−1 μg protein) was subjected to gel filtration on a Superose-12 column (25×0.5-cm) in 50 mM Tris-chloride (pH 7.5) containing 0.2 M NaCl, 1 mM DTT, and 0.2% octyl-β-D-glucopyranoside at a flow rate of 0.2 ml/min. Fractions of 0.5 ml were collected.
Figure 7B:
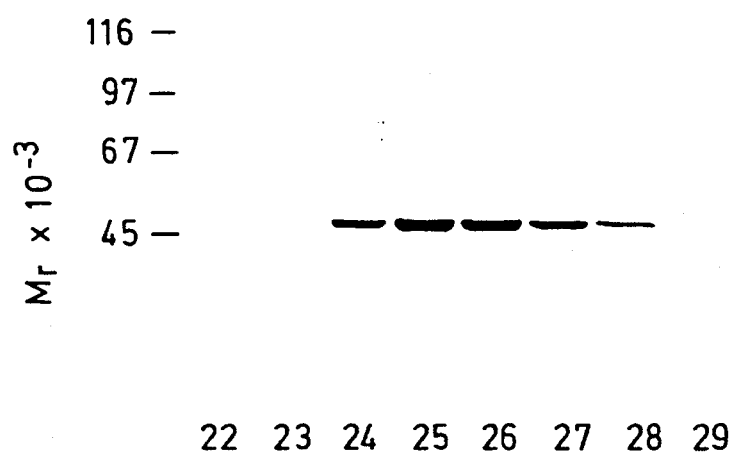
FIG. 7B, a 0.42-ml aliquot of each fraction was concentrated to 40 μl with a Centricon 30 Concentrator (Amicon), and 25 μl of this material was then subjected to electrophoresis on an 10% SDS polyacrylamide gel. The gel was stained with silver nitrate and calibrated with marker proteins (far-right lane).
Figure 8:
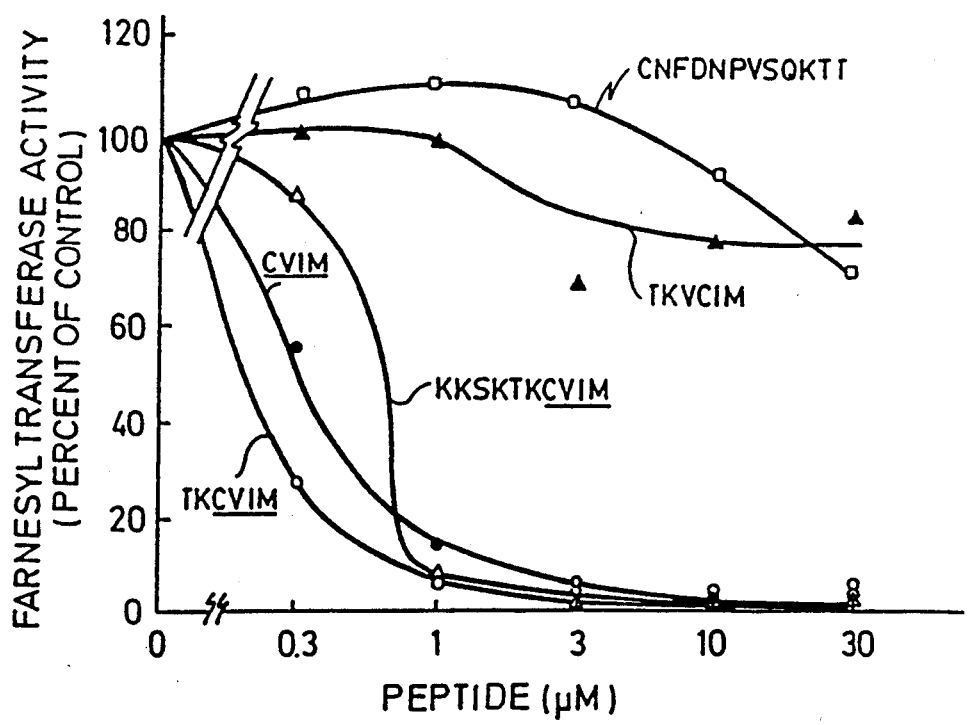
FIG. 8. Inhibition of Farnesyl:Protein Transferase Activity by Peptides. Each standard reaction mixture contained 10 pmol [$^3$H]FPP, 1.8 μg of partially purified farnesyl:protein transferase, 40 μM p21$^{H\text{-}ras}$, and the indicated concentration of competitor peptide added in 3 μl of 10 mM DTT. After incubation for 1 h at 37° C., TCA-precipitable radioactivity was measured as described in Experimental Procedures. Each value is the mean of triplicate incubations (no peptide) or a single incubation (+peptide). A blank value of 0.11 pmol/h was determined in a parallel incubation containing 20 mM EDTA. This blank was subtracted from each value before calculating "% of control" values. The "100% of control" value after subtraction of the blank was 3.78 pmol of [$^3$H]FPP p21$^{H\text{-}ras}$ formed per h. Peptides Δ, o and o correspond to the COOH-terminal 10, 6, and 4 amino acids of wild-type human p21$^{H\text{-}ras}$ protein, respectively. Peptides □ and ▲ are control peptides.

Step 4—Gel Filtration:

Affinity-purified farnesyl transferase (~1 μg) was chromatographed on a Superose 12 column as described in the legend to FIG. 7.

In the enzyme characterization experiments of FIGS. 1–4, 8, and 9, a partially purified fraction of farnesyl:protein transferase was used. This enzyme was prepared by Steps 1 and 2 as described above, after which 6 mg of the Mono Q-purified material was concentrated to 2 ml and then loaded onto a 1.6×50-cm Sephacryl S-200 high resolution gel filtration column (Pharmacia LKB Biotechnology). The column was equilibrated with 50 mM Tris-chloride (pH 7.5) containing 1 mM DTT, 0.2M NaCl, 20 μM ZnCl$_2$, and 0.2% octyl-β-glucopyranoside and eluted with the same buffer at a flow rate of 15 ml/hour. Only the peak fraction, containing 1mg protein and 40% of initial activity, was used for studies.

4. Identification of $^3$H-Isoprenoid Transferred from [$^3$H]FPP

A modification of the procedure described by Casey et al. (6) was employed as follows: Briefly, two standard transferase reactions of 25 μl each were conducted for 1 hour at 37° C. The mixtures were then pooled, and a 25-μl aliquot from the 50-μl pooled sample was diluted to 250 μl with 2% (w/v) SDS. This mixture was precipitated with an equal volume of 30% TCA, filtered through nitrocellulose, (7 mm disc), washed twice with 250 μl 6% TCA/2% SDS followed by five washes with 5% TCA, digested with 8 μg trypsin, and subjected to cleavage with methyl iodide. The released $^3$H-isoprenoids were extracted into chloroform/methanol and chromatographed on a reverse-phase HPLC system as described in the legend to FIG. 4.

5. Other Methods

SDS polyacrylamide gel electrophoresis was carried out as described by Laemmli (16). Gels were calibrated with high range SDS-PAGE standards (Bio-Rad). Protein content of extracts was measured by the method of Lowry, et al. (17) except for that of the affinity-purified material, which was estimated by comparison to the bovine serum albumin marker ($M_r$ 66,000) following SDS gel electrophoresis and Coomassie staining.

6. Results and Discussion

Figure 1B:
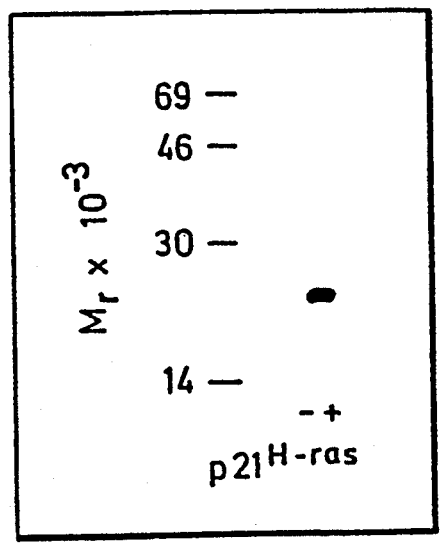
FIG. 1B The inset shows the migration on a 12% SDS polyacrylamide gel of an aliquot from a reaction carried out for 1 h in the absence or presence of $p21^{H\text{-}ras}$. The gel was treated with Entensify solution (DuPont), dried, and exposed to XAR film for 2 days at $-70°$ C.

As an initial attempt to identify a farnesyl protein transferase enzyme, rat brain cytosol was fractionated with ammonium sulfate and the active fraction subjected to ion exchange chromatography on a Mono Q column followed by gel filtration on Sephacryl S-200. FIG. 1 shows that the active fraction from this column incorporated radioactivity from [$^3$H]farnesol into trichloroacetic acid precipitable p21$^{H\text{-}ras}$ in a time-dependent fashion at 37° C. The incorporated radioactivity could be visualized as a band of the expected molecular weight of ~21 kDa on SDS polyacrylamide gels (inset). The concentration of [$^3$H]farnesyl pyrophosphate that gave half-maximal reaction velocity was approximately 0.5 μM (FIG. 2A). The half-maximal concentration for p21$^{Hras}$ was approximately 5 μM, and there was no difference when the p21$^{H\text{-}ras}$ was equilibrated with a nonhydrolyzable GTP or ATP analogue or with GDP (FIG. 2B).

With p21$^{H\text{-}ras}$ as a substrate, the transferase reaction was inhibited by 0.15 mM EDTA, and this inhibition was reversed by 0.1 to 1.0 mM concentrations of zinc or magnesium chloride (FIG. 3). At higher concentrations of zinc chloride, inhibition was observed.

Figure 4A:
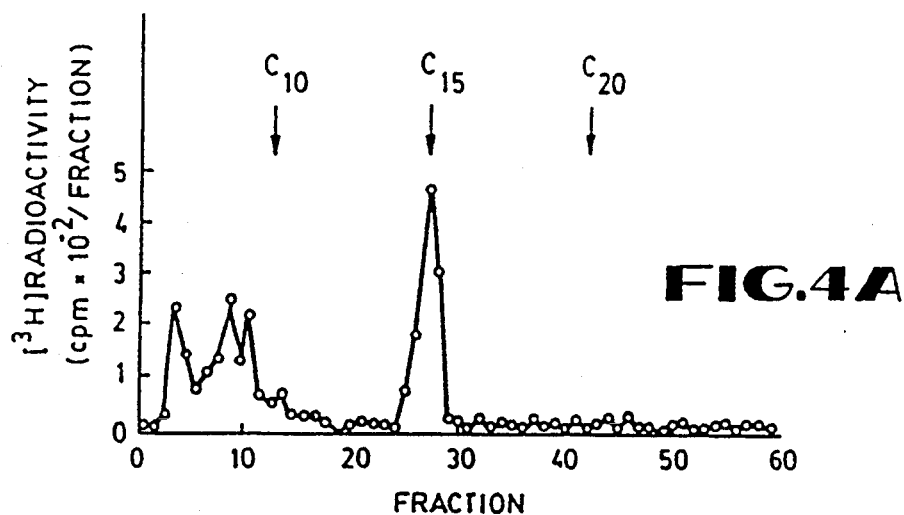
FIG. 4A,B. Identification of [$^3$H]FPP-derived Radioactive Material Transferred to $p21^{H\text{-}ras}$.
Figure 4B:
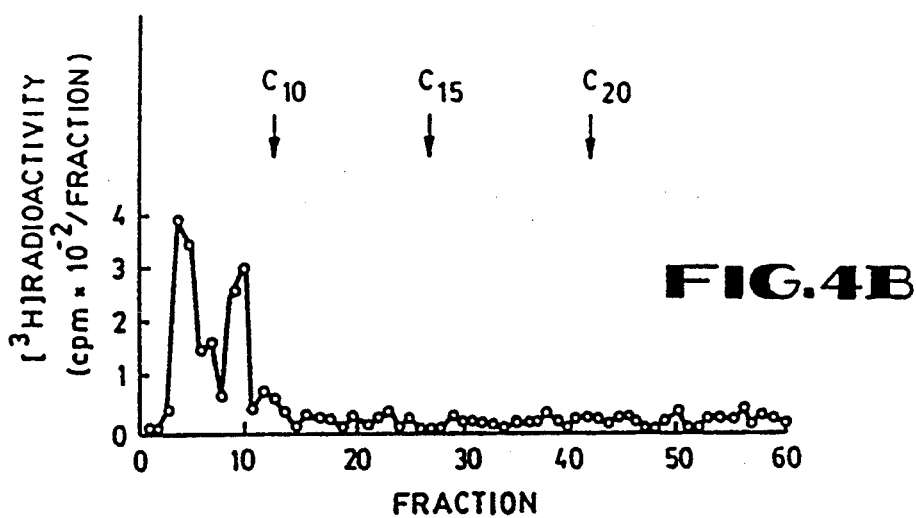
FIG. 4B: another aliquot was treated identically except methyl iodide was omitted. After cleavage, the extracted material was dried under nitrogen, resuspended in 0.4 ml of 50% (v/v) acetonitrile containing 25 mM phosphoric acid and 6 nmoles of each isoprenoid standard as indicated. The mixture was subjected to reverse phase HPLC (C18, Phenomex) as described by Casey, et al. (6) except that an additional 10-min wash with 100% acetonitrile/phosphoric acid was used. The isoprenoid standards were identified by absorbance at 205 nm: $C_{10}$, all-trans geraniol; $C_{15}$, all-trans farnesol; $C_{20}$, all-trans geranylgeraniol.

To confirm that the transferred material was [$^3$H]farnesol, the washed trichloracetic acid-precipitated material was digested with trypsin, the radioactivity released with methyl iodide, and the products subjected to reverse-phase HPLC. The methyl iodide-released material co-migrated with an authentic standard of all-trans farnesol ($c_{15}$) (FIG. 4A). Some radioactivity emerged from the column prior to the geranol standard ($C_{10}$), but this was the same in the presence and absence of methyl iodide treatment. This early-eluting material was believed to represent some tryptic peptides whose radioactivity was not released by methyl iodide.

Figure 5:
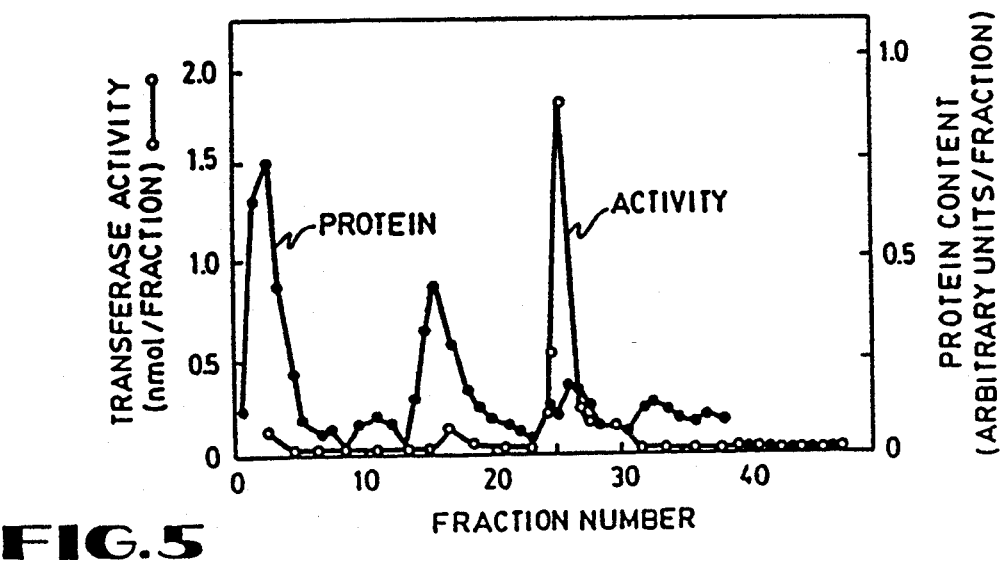
FIG. 5. Chromatography of Farnesyl:Protein Transferase on a Mono Q column. The 30–50% ammonium sulfate fraction from rat brain (200mg) was applied to a Mono Q column (10×1-cm) equilibrated in 50 mM Tris-chloride (pH 7.5) containing 1 mM DTT, 20 µM ZnCl$_2$, and 0.05 M NaCl. The column was washed with 24 ml of the same buffer containing 0.05 M NaCl, followed by a 24-ml linear gradient from 0.05 to 0.25 M NaCl, followed by a second wash with 24 ml of the same buffer containing 0.25 M NaCl. The enzyme was then eluted with a 112-ml linear gradient of the same buffer containing 0.25–1.0M NaCl at a flow rate of 1 ml/min. Fractions of 4 ml were collected. An aliquot of each fraction (2µl) was assayed for farnesyl:protein transferase activity by the standard method (o). The protein content of each fraction (●) was estimated from the absorbance at 280 mM.

FIG. 5 shows the elution profile of farnesyl transferase activity from a Mono Q column. The activity appeared as a single sharp peak that eluted at approximately 0.35M sodium chloride.

The peak fractions from the Mono Q column were pooled and subjected to affinity chromatography on a column that contained a covalently-bound peptide corresponding to the carboxyl-terminal 6-amino acids of p21$^{K\text{-}rasB}$. All of the farnesyl transferase activity was adsorbed to the column, and about 50% of the applied activity was recovered when the column was eluted with a Tris-succinate buffer at pH 5.0.

Table II summarizes the results of a typical purification procedure that started with 50 rat brains. After ammonium sulfate precipitation, mono Q chromatography, and affinity chromatography, the farnesyl transferase was purified approximately 61,000-fold with a yield of 52%. The final specific activity was about 600,000 units/mg.

Figure 6A:
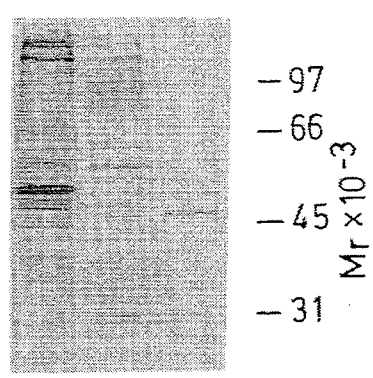
FIG. 6A. SDS Polyacrylamide Gel Electrophoresis of Farnesyl:Protein Transferase at Various Stages of Purification. 10 µg of the 30–50% ammonium sulfate fraction (lane 1), 3 µg of the Mono Q fraction (lane 2), and approximately 90 ng of the peptide affinity-column fraction (lane 3) were subjected to SDS-10% polyacrylamide gel electrophoresis, and the protein bands were detected with a silver stain. The farnesyl:protein transferase activity in each sample loaded onto the gel was approximately 0.1, 0.8, and 54 units/lane for lanes 1, 2, and 3, respectively. The molecular weights for marker protein standards are indicated. Conditions of electrophoresis: 10% mini gel run at 30 mA for 1 hour.
Figure 6B:
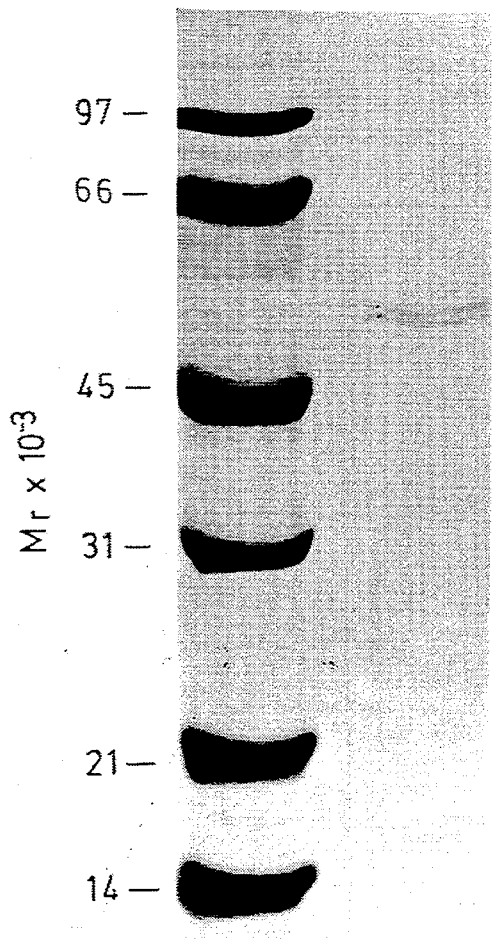
FIG. 6B. SDS Polyacrylamide Gel Electrophoresis of Purified Farnesyl: Protein Transferase. 0.7 μg of the peptide affinity-purified-column fraction (right lane) was subjected to SDS-10% polyacrylamide gel electrophoresis, and the protein bands were detected with a Coomassie Blue Stain. The molecular weights for marker protein standards (left lane) are indicated. Conditilank was 3.78 pmol of [$^3$H]FPP p21$^{H\text{-}ras}$ formed per hour. Peptides a, o and o correspond to the COOH-terminal 10, 6, and 4 amino acids of wild-type human p21$^{H\text{-}ras}$ protein, respectively. Peptides □ and ▲ are control peptides.

FIG. 6A shows the SDS gel electrophoretic profile of the proteins at each stage of this purification as visualized by silver staining. The peptide affinity column yielded a single protein band with an apparent subunit molecular weight of 50,000. When the purified enzyme was subjected to SDS gel electrophoresis under more sensitive conditions, the 50-kDa protein could be resolved into two closely spaced bands that were visualized in approximately equimolar amounts (FIG. 6B).

To confirm that the 50-kDa band was the farnesyl transferase enzyme, the affinity column purified material was subjected to gel filtration. FIG. 7 shows that the farnesyl transferase activity and the 50-kDa band co-eluted from this column at a position corresponding to an apparent molecular weight of 70–100 kDa as determined from the behavior of markers of known molecular weight.

TABLE II

PURIFICATION OF FARNESYL:PROTEIN TRANSFERASE FROM RAT BRAIN

| Fraction | Protein mg | Specific Activity units/mg | Total Activity units | Purification −fold | Recovery % |
|---|---|---|---|---|---|
| 30–50% Ammonium Sulfate | 712 | 9.7$^a$ | 6906 | 1 | 100 |
| Mono Q | 30 | 275 | 8250 | 28 | 119 |
| Affinity Column | ~0.006$^b$ | 600,000 | 3600 | 61,855 | 52 |

The purification procedure was started with 50 rat brains.
$^a$One unit of enzyme activity is the amount of enzyme that transfers 1 pmol of [$^3$H]farnesol from [$^3$H]FPP into acid-precipitable p21$^{H\text{-}ras}$ per h under the standard conditions.
$^b$Protein concentration was estimated by coomassie blue staining of a SDS polyacrylamide gel using various amounts (0.5 to 2 μg) of bovine serum albumin as a reference standard.

The adherence of the farnesyl transferase to the peptide affinity column suggested that the enzyme was capable of recognizing short peptide sequences. To test for the specificity of this peptide recognition, the ability of various peptides to compete with p21$^{H\text{-}ras}$ for the farnesyl transferase activity was measured. The peptide that was used for affinity chromatography corresponded to the carboxyl terminal six amino acids of P21$^{K\text{-}rasB}$ (TKCVIM). As expected, this peptide competitively inhibited farnesylation of P21$^{H\text{-}ras}$ (open circles in FIG. 8). The terminal 4-amino acids in this sequence (CVIM) (closed circles) were sufficient for competition. These two short peptides were no less effective than a peptide that contained the final 10-amino acids of the sequence (KKSKTKCVIM) (open triangles). The simple transposition of the cysteine from the fourth to the third position from the COOH-terminus of the hexapeptide (TKVCIM) (closed triangles) severely reduced inhibitory activity. An irrelevant peptide (closed squares) also did not inhibit.

Figure 9:
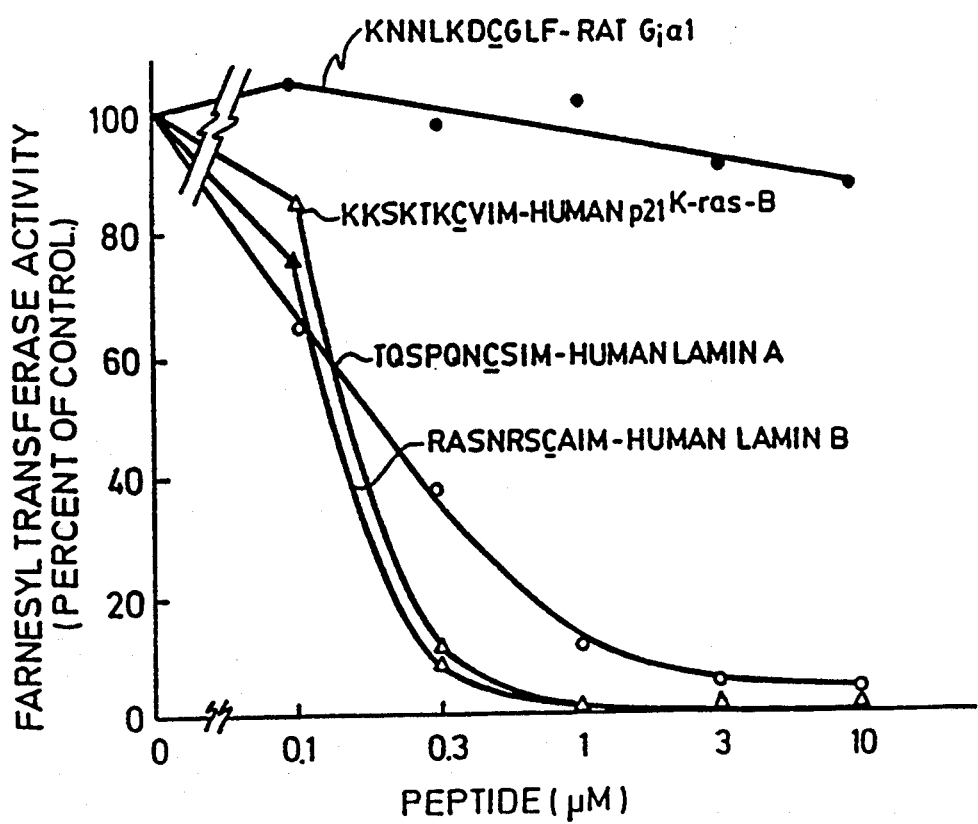
FIG. 9. Inhibition of Farnesyl:Protein Transferase Activity by Peptides. Incubations were carried out exactly as described in the legend to FIG. 8. The "100% of control value" was 2.92 pmol of [$^3$H]farnesyl p21$^{H\text{-}ras}$ formed per hour. The blank value was 0.20 pmol/h. Each peptide consisted of the COOH-terminal 10 residues of the indicated protein.

FIG. 9 compares the inhibitory activities of four peptides of 10-amino acids each, all of which contain a cysteine at the fourth position from the COOH-terminus. The peptides corresponding to the COOH-terminus of human p21$^{K\text{-}rasB}$ and human lamin A and lamin B all inhibited farnesylation. All of these peptides are known to be prenylated in vivo (6, 15). On the other hand, the peptide corresponding to the sequence of rat Giα1, a 40kDa G protein that does not appear to be farnesylated in vivo (Casey, P., unpublished observations), did not compete for the farnesyl transferase reaction.

In data not shown it was found that the 10-amino acid peptide corresponding to the COOH-terminus of p21$^{H\text{-}ras}$ (CVLS), p21$^{N\text{-}ras}$ (CVVM), and p21$^{H\text{-}rasA}$ (CIIM) all competed for the farnesylation reaction.

EXAMPLE II

FURTHER CHARACTERIZATION OF FARNESYL: PROTEIN TRANSFERASE

In the present Example, a series of tetrapeptides were tested for their ability to bind to the rat brain p21$^{H\text{-}ras}$ farnesyl:protein transferase as estimated by their ability to compete with p21$^{H\text{-}ras}$ in a farnesyl transfer assay. Peptides with the highest affinity had the structure Cys-A1-A2-X, where A1 and A2 are aliphatic amino acids and X is a C-terminal methionine, serine, or phenylalanine. Charged residues reduced affinity slightly at the A1 position and much more drastically at the A2 and X positions. Effective inhibitors included tetrapeptides corresponding to the COOH—termini of all animal cell proteins known to be farnesylated. In contrast, the tetrapeptide CAIL, which corresponds to the COOH-terminus of the only known examples of geranylgeranylated proteins (neural G protein γ subunits) did not compete in the farnesyl transfer assay, suggesting that the two isoprenes are transferred by different enzymes. A biotinylated hexapeptide corresponding to the COOH—terminus of p21$^{K\text{-}rasB}$ was farnesylated, suggesting that at least some of the peptides serve as substrates for the transferase. The data are consistent with a model in which a hydrophobic pocket in the farnesyl:protein transferase recognizes tetrapeptides through interactions with the cysteine and the last two amino acids.

1. Materials and Methods a. Peptides

Peptides were prepared by established procedures of solid-phase synthesis (18) Tetrapeptides were synthesized on the Milligen 9050 Synthesizer using Fmoc chemistry. After deprotection of the last residue, a portion of the resin was used to make the N-acetyl-modified version of CVIM. This was done off-line in a solution of acetic anhydride and dimethylformamide at pH 8 (adjusted with diisopropylethylamine). The acetylated and unacetylated peptides were cleaved with 50 ml of trifluoroacetic acid:phenol (95:5) plus approximately 1 ml of ethanedithiol added as a scavenger. The N-octyl-modified version of CVIM was synthesized on an Applied Biosystems Model 430 Synthesizer using tBoc chemistry. The octyl group was added in an amino acid cycle using octanoic acid. The peptide was cleaved from the resin at 0° C. with a 10:1:1 ratio of HF (mls):resin (g):anisole (ml). The peptides were purified by high pressure liquid chromatography (HPLC) on a Beckman C18 reverse phase column (21.1 cm×15 cm), eluted with a water-acetonitrile gradient containing 0.1% (v/v) trifluouroacetic acid. Identity was confirmed for all peptides by fast atom bombardment (FAB) mass spectrometry. Just prior to use, each peptide was dissolved at a concentration of 0.8 mM in 10 mM dithiothreitol (DTT), and all dilutions were made in 10 mM DTT.

Biotinylated KTSCVIM was synthesized on an Applied Biosystems 430A Synthesizer. The biotin group was added after removal of the N-terminal protecting group before cleavage of the peptide from the resin. Specifically, a 4-fold molar excess of biotin 4-nitrophenyl ester was added to the 0.5 g resin in 75 ml dimethylformamide at pH 8 and reacted for 5 hours at room temperature. Cleavage, identification, and purification were carried out as described above.

To synthesize S-acetoamido CVIM, purified CVIM was dissolved at a final concentration of 1 mM in 0.1 ml of 0.5M Tris-chloride (pH 8.0) containing 15 mM DTT. The tube was flushed with nitrogen for 2 min, sealed, and incubated for 2.5 hours at 37° C. to reduce the cysteine residue, after which iodoacetamide was added to achieve a final concentration of 35 mM. After incubation for 15min at 37° C., the reaction was stopped by addition of 10 mMDTT. Complete alkylation of CVIM was confirmed by FAB spectrometry and HPLC. The molecular weight of the product corresponded to the expected molecular mass of S-acetoamido CVIM.

b. Assay for Farnesyl:Protein Transferase

The standard assay involved measuring the amount of [$^3$H]farnesyl transferred from all-trans [$^3$H]FPP to recombinant human p21$^{H\text{-}ras}$ as described in Example I. Each reaction mixture contained the following concentrations of components in a final volume of 25 μl: 50 mM Tris-chloride (pH 7.5), 50 μM ZnCl$_2$, 30 mM KCl, 1 mM DTT, 30 or 40 μM p21$^{H\text{-}ras}$, 15 pmol [$^3$H]FPP (12–23,000 dpm/pmol), 4 to 7.5 μg of partially purified farnesyl:protein transferase (Mono Q fraction, see Example I), and the indicated concentration of competitor peptide added in 3 μl of 10 mM DTT. After incubation for 30–60 min at 37° C., the amount of [$^3$H]farnesyl present in trichloroacetic acid-precipitable p21$^{H\text{-}ras}$ was measured by a filter assay as described in Example I. A blank value (<0.6% of input [$^3$H]FPP) was determined in parallel incubations containing no enzyme. This blank value was subtracted before calculating "% of control" values.

c. Transfer of [$^3$H]Farnesyl from [$^3$H]FPP to Biotinylated KTSCVIM Peptide

This assay takes advantage of the fact that peptides containing the Cys-AAX motif of ras proteins can serve as substrates for prenylation by farnesyl transferase. A heptapeptide containing the terminal four amino acids of p21$^{K\text{-}rasB}$ was chosen as a model substrate since it has a 20 to 40-fold higher affinity for the enzyme than does the COOH-terminal peptide corresponding to p21$^{H\text{-}ras}$. A biotinylated peptide is used as substrate so that the reaction product, [$^3$H]farnesylated peptide, can be trapped on a solid support such as streptavidinagarose. The bound [$^3$H]farnesylated peptide can then be washed, separated from unincorporated [$^3$H]FPP, and subjected to scintillation counting.

The biotin-modified KTSCVIM is synthesized on an Applied Biosystems 430A Synthesizer using established procedures of solid phase peptide synthesis. The biotin group is added after deprotection of lysine and before cleavage of the peptide from the resin. The identity and purity of the biotinylated peptide is confirmed by quantitative amino acid analysis and fast atom bombardment (FAB) mass spectrometry.

An aliquot of biotinylated KTSCVIM (0.4mg) is dissolved in 0.6 ml of 10 mM sodium acetate (pH 3) buffer containing 1 mM DTT and 50% ethanol to give a final concentration of 0.67mg/ml or 601 μM. This solution can be stored at 4° C. for at least 1 month. Immediately prior to use, the peptide solution is diluted with 1 mM DTT to achieve a peptide concentration of 18 μM. The standard reaction mixture contains the following components in a final volume of 25 μl: 50 mM Tris-chloride (pH 7.5), 50 μM ZnCl$_2$, 20 mM KCl, 1 mM DTT, 0.2% (v/v) octyl-β-glucopryranoside, 10–15 pmol of [$^3$H]FPP (15–50,000 dpm/pmol), 3.6 μM biotinylated KTSCVIM, and 2–4 units of enzyme. After incubation at 37° C. for 30–60 min in 0.5-ml siliconized microfuge tubes, the reaction is stopped by addition of 200 μl of 20 mM Tris-chloride (pH 7.5) buffer containing 2 mg/ml bovine serum albumin, 2% SDS, and 150 mM NaCl. A 25-μl aliquot of well mixed streptavidin-agarose (Bethesda Research Laboratories, Cat. No. 5942SA) is then added, and the mixture is gently shaken for 30 min at room temperature to allow maximal binding of the [$^3$H]farnesylated peptide to the beads.

The beads are then collected by spinning the mixture for 1 min in a microfuge (12,500 rpm). The supernatant is removed, and the beads are washed three times with 0.5 ml of 20 mM Tris-chloride (pH 7.5) buffer containing 2 mg/ml bovine serum albumin, 4% SDS, and 150 mM NaCl. The pellet is resuspended in 50 μl of the same buffer and transferred to a scintillation vial using a 200-μl pipettor in which the tip end has been cut off at an angle. The beads remaining in the tube are collected by rinsing the tube with 25 μl of the above buffer and adding it plus the pipettor to the vial. A blank value, which consists of the radioactivity adhering to the beads in parallel incubations containing no enzyme, should be less than 0.5% of the input [$^3$H]FPP.

2. Results

Figure 10A:
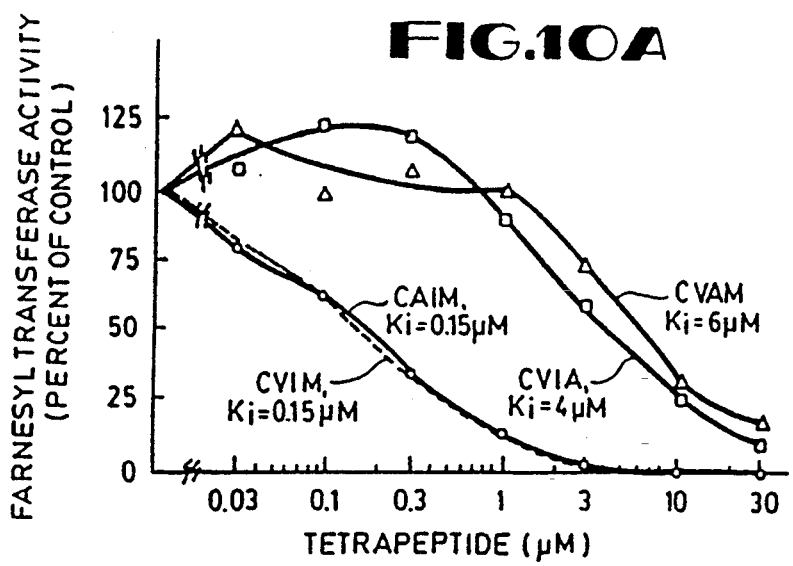
FIG. 10. Inhibition of Farnesyl:Protein Transferase By Tetrapeptide Analogues of CVIM. The standard assay mixture contained 15 pmol [$^3$H]FPP, 4 to 7.5 μg partially purified farnesyl transferase, 30 or 40 μM p21$^{H\text{-}ras}$, and the indicated concentration of competitor tetrapeptide. After 30 or 60 min, the amount of [$^3$H]farnesyl attached to p21$^{H\text{-}ras}$ was measured by trichloracetic acid precipitation as described in the methods section of Example II. Each value is the average of duplicate or triplicate incubations (no peptide) or a single incubation (+peptide). Each tetrapeptide was tested in a separate experiment together with equivalent concentrations of CVIM. The values for inhibition by CVIM ( . . . ) represent mean values from 21 experiments in which the mean "100% of control" value was 13 pmol min$^{-1}$ mg protein$^{-1}$. K$_i$, concentration of tetrapeptide giving 50% inhibition.
Figure 10B:
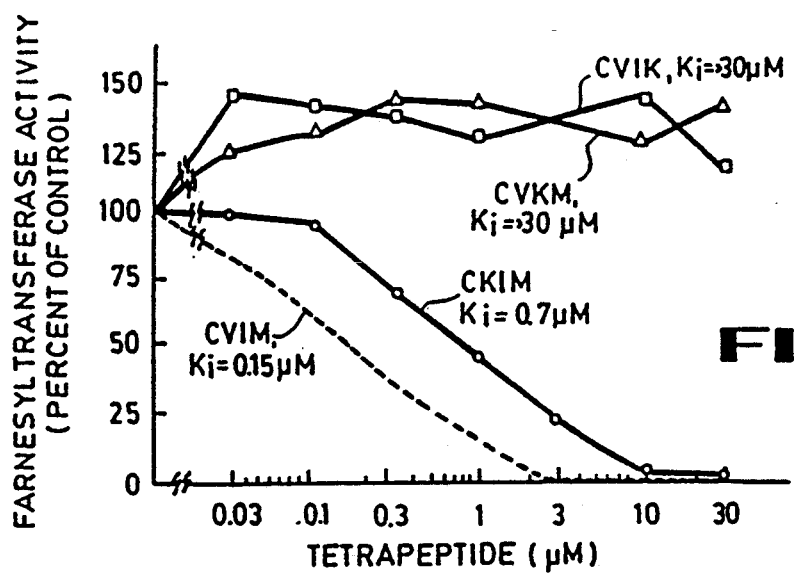
Figure 10C:
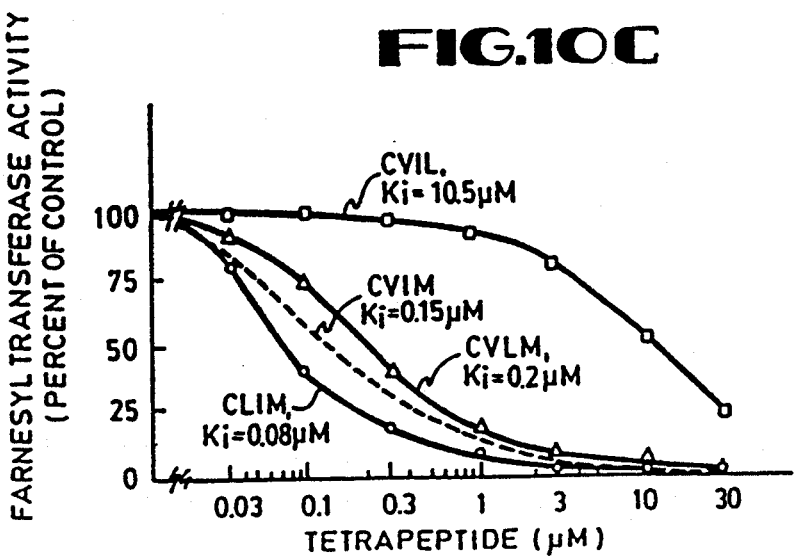

To screen peptides for their affinity for the farnesyl:protein transferase, studies were conducted wherein the ability of the peptides to compete with p21$^{H\text{-}ras}$ for acceptance of [$^3$H]farnesyl from [$^3$H]FPP as catalyzed by a partially purified rat brain farnesyl:protein transferase was tested. As a reference point for the peptides, the tetrapeptide CVIM corresponding to the COOH-terminal sequence of p21$^{K\text{-}rasB}$ was employed. FIG. 10 shows a series of typical experiments in which alanine (Panel A), lysine (Panel B), or leucine (Panel C) was systematically substituted at each of the three positions following cysteine in CVIM. In each experiment the results were compared with those obtained with CVIM. Alanine and lysine were tolerated only at the A1 position. Insertion of these amino acids at the A2 or X positions decreased the affinity for the enzyme by more than 30-fold as estimated by the concentration required for 50% inhibition. Leucine was tolerated at the A2 position, but it decreased the affinity when inserted at the X position.

Figure 11:
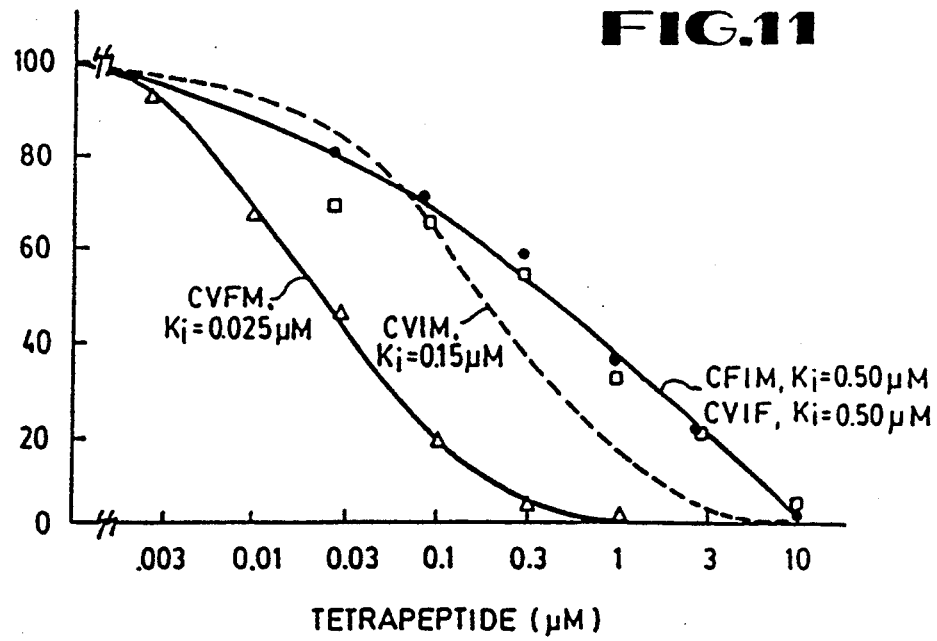
FIG. 11. Inhibition of Farnesyl:Protein Transferase Activity By Phenylalanine-Containing Analogues of CVIM. Enzyme activity was measured in the presence of the indicated concentration of competitor tetrapeptide as described in the legend to FIG. 10.

The substitution of phenylalanine for isoleucine at the A2 position increased the affinity for the enzyme by 6-fold, with half-maximal inhibition occurring at 25 nM (FIG. 11). No such effect was observed when phenylalanine was inserted at either of the other two positions.

In addition to performing assays with p21$^{H\text{-}ras}$ as a substrate, assays were also performed in which the substrate was a biotinylated heptapeptide, KTSCVIM, which contains the COOH-terminal four amino acids of p21$^{H\text{-}rasB}$ (2). The biotin was attached to the NH2-terminus by coupling to the resin-attached peptide. The [$^3$H]farnesylated product was isolated by allowing it to bind to beads coated with streptavidin as described in section c. above.

Figure 12A:
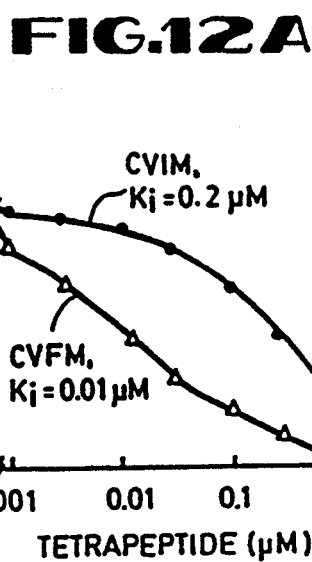
FIG. 12A,B. Inhibition of Farnesylation of p21$^{H\text{-}ras}$ (A) and Biotinylated KTSCVIM (B) By CVFM.
Figure 12B:
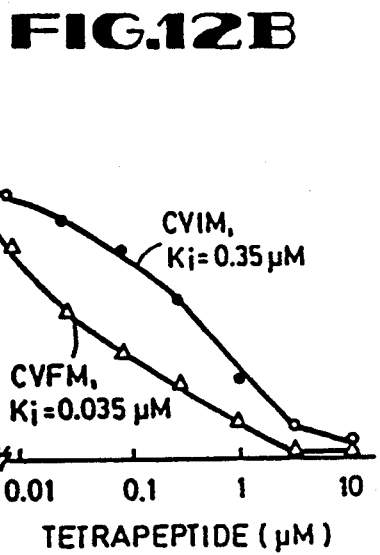
FIG. 12B: Each reaction contained 15 pmol [$^3$H]FPP, 4.5 or 6 ng of purified farnesyl:protein transferase, 3.4 μM biotinylated KTSCVIM, and the indicated concentration of competitor tetrapeptide. After incubation for 30 min at 37° C., the [$^3$H]farnesyl-labeled peptide was trapped on streptavidin-agarose, washed, separated from the unincorporated [$^3$H]FPP, and subjected to scintillation counting. Values shown are the mean of 3 experiments. The "100% of control" values were 10, 17, and 21 nmol min$^{-1}$ mg protein$^{-1}$.

FIG. 12 shows that the peptide CVFM was more potent than CVIM when either p21$^{H\text{-}ras}$ or the biotinylated heptapeptide was used as acceptor (Panels A and B, respectively). In contrast to the other studies, which were conducted with a partially purified enzyme, the studies of FIG. 12 were carried out with a homogeneous preparation of affinity-purified farnesyl:protein transferase.

Figure 13A:
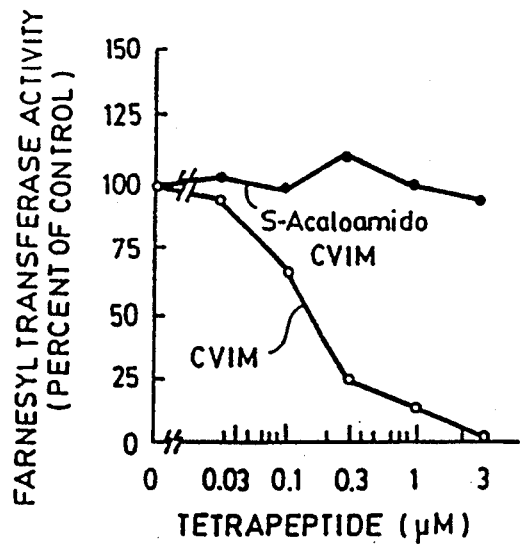
FIG. 13A,B. Inhibition of Farnesyl:Protein Transferase By Modified Tetrapeptides. Enzyme activity was measured in the presence of varying concentrations of the indicated tetrapeptide as described in the legend to FIG. 10. The "100% of control" values were 9.3 and 9.2 pmol min$^{-1}$ mg protein$^{-1}$ in FIGS. 13A and 13B, respectively.
Figure 13B:
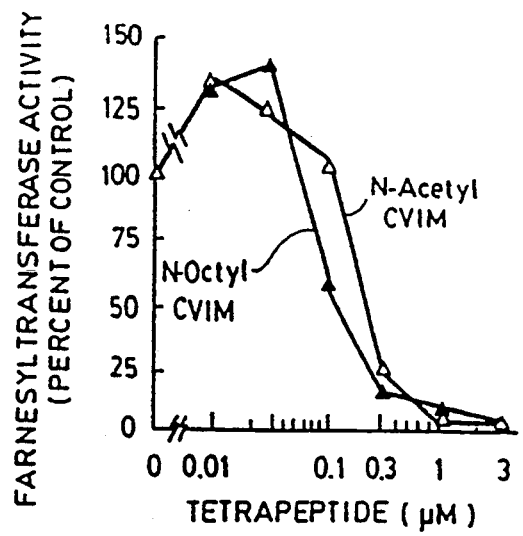

The free sulfhydryl group for the cysteine is likely required for tetrapeptide inhibition, as indicted by the finding that derivitization with iodoacetamide abolished inhibitory activity (FIG. 13A). A blocked NH2-terminus is not required, as indicated by similar inhibitory activity of N-acetyl CVIM and N-octyl CVIM (FIG. 13B) as compared to that of CVIM (FIG. 13A).

Figure 14:
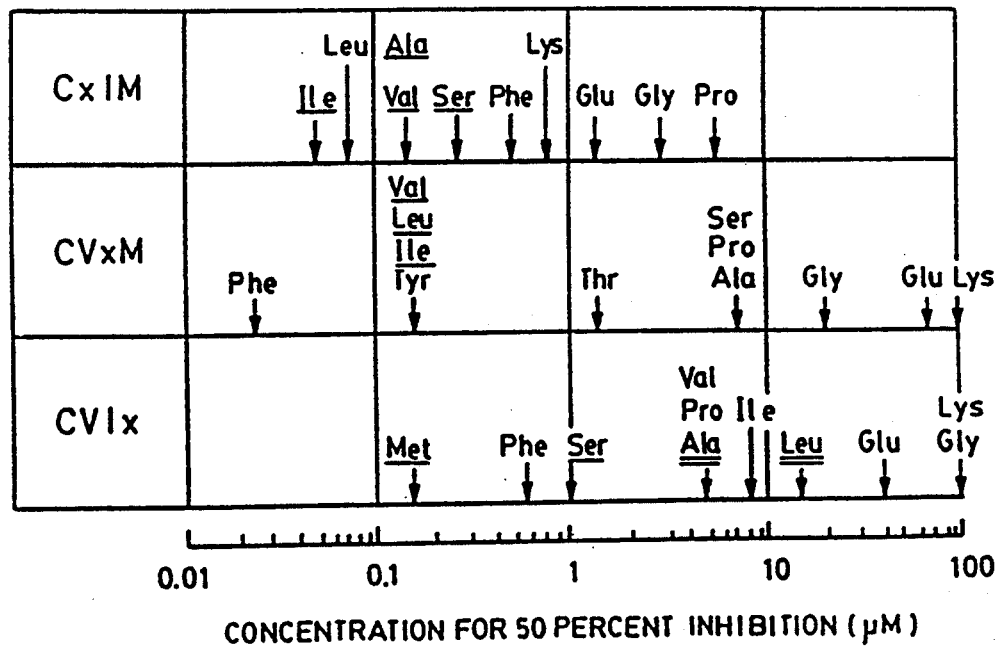
FIG. 14. Inhibition of Farnesyl:Protein Transferase By Tetrapeptides With Single Amino Acid Substitutions in CVIM. Enzyme activity was measured in the presence of the indicated competitor tetrapeptide as described in the legend to FIGS. 10 and 11. Each tetrapeptide was tested at seven different concentrations ranging from 0.01 to 100 μM. The concentration of tetrapeptide giving 50% inhibition was calculated from the inhibition curve. The single-and double underlines denote tetrapeptides corresponding to the COOH—terminal sequence of mammalian and fungal proteins, respectively, that are candidates for farnesylation (see Table III).
Figure 15:
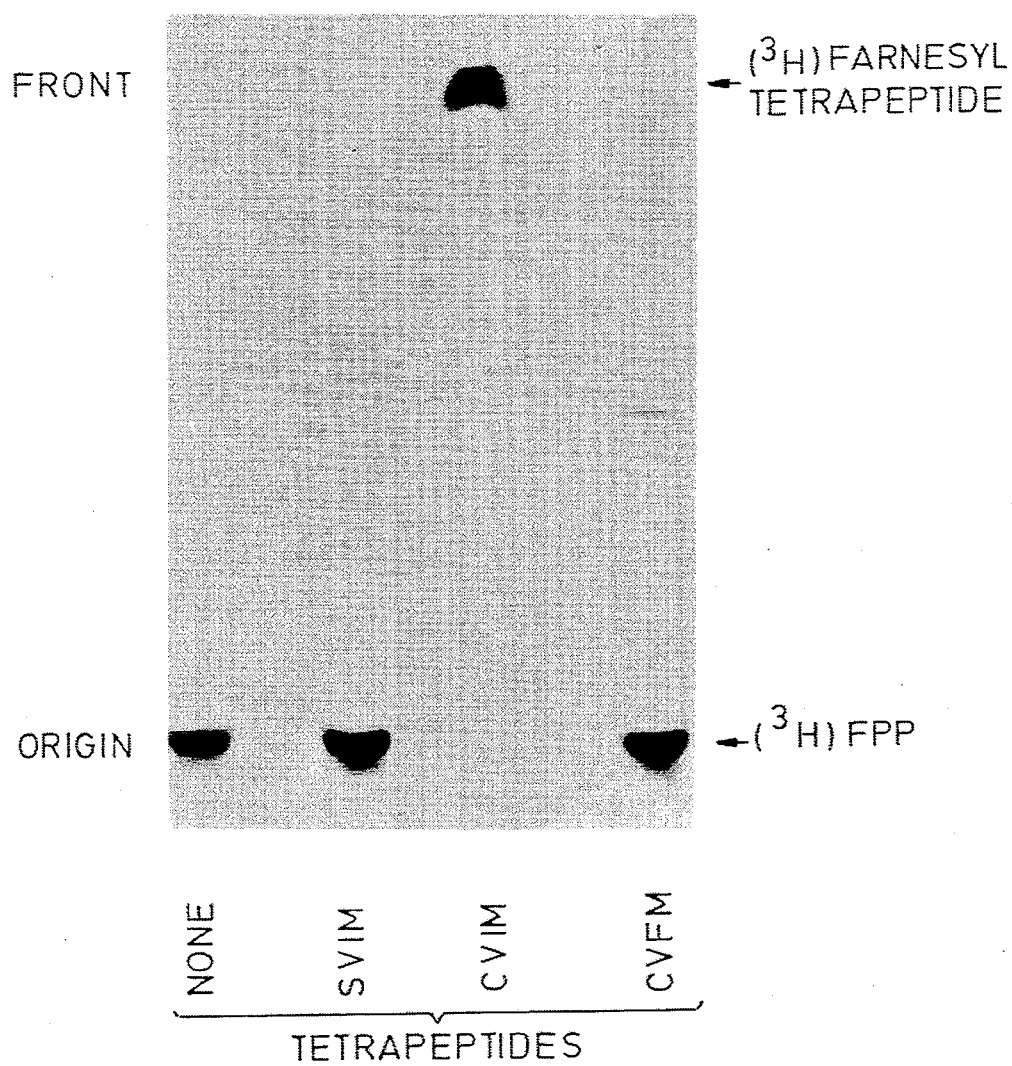
FIG. 15. Farnesylation of CVIM but not CVFM by Purified Farnesyl:protein Transferase. The standard assay mixture (25 μl) contained 17 pmol [$^3$H]FPP (44,000 dpm/pmol), 5 ng of purified farnesyl:protein transferase, 0.2% (w/v) octyl-β-D-glucoside, and 3.6 μM of the indicated tetrapeptide. After incubation for 15 min at 37° C, the entire reaction mixture was subjected to thin layer chromatography for 4 hours on Polygram SIL G sheet (Brinkmann Instruments) in a solvent system containing N-propanol/concentrated NH4OH/water (6:3:1). The TLC sheet was then dried, sprayed with ENHANCE Spray (Dupont-New England Nuclear) and exposed to Kodak X-OMAT AR Film XAR-5 for 25 hours at −70° C.

FIG. 14 summarizes the results of all competition assays in which substitutions in the CVIM sequence were made. The results are presented in terms of the peptide concentration required for 50% inhibition. Table III summarizes the results of other experiments in which tetrapeptides corresponding to the COOH-termini of 19 proteins were studied, many of which are known to be farnesylated. The implications of these studies are discussed below in Section 3.

TABLE III

Inhibition of Rat Farnesyl:Protein Transferase by COOH-Terminal Tetrapeptides Corresponding to Known Proteins

| Protein | Species | COOH-Terminal Tetrapeptide | Concentration for 50% Inhibition μM |
|---|---|---|---|
| *p21$^{K\text{-}rasB}$ | Human, mouse | CVIM | 0.15 |
| *p21$^{K\text{-}rasA}$ | Human | CIIM | 0.15 |
| p21$^{N\text{-}ras}$ | Human | CVVM | 0.15 |
| p21$^{N\text{-}ras}$ | Mouse | CVLM | 0.15 |
| *Lamin B | Human, Xenopus laevis | CAIM | 0.15 |
| Lamin A | Human, Xenopus laevis | CSIM | 0.20 |
| Retinal cGMP phosphodiesterase, α subunit | Bovine | CCVQ | 0.35 |
| *ras1 | S. cerevisciae | CIIC | 0.35 |
| *ras2 | S. cerevisciae | CIIS | 0.35 |
| *γ-Subunit of transducin | Bovine | CVIS | 1.0 |
| p21$^{H\text{-}ras}$ | Chicken | CVIS | 1.0 |
| p21$^{H\text{-}ras}$ | Human, rat | CVLS | 3.0 |
| *a-Mating factor | S. cerevisciae | CVIA | 5.0 |
| rap2b | Human | CVIL | 11 |
| Dras | Dictostelium | CLIL | 17 |
| rap1a/krev1 | Human | CLLL | 22 |
| *Mating factor | R. Toruloides | CTVA | 30 |
| γ-Subunit of G protein | Bovine | CAIL | 100 |
| HMG CoA reductase-1 | S. cerevisciae | CIKS | >100 |

Enzyme activity was measured in the presence of the indicated tetrapeptide as described in the legend to FIG. 10. Each tetrapeptide was tested at seven different concentrations ranging from 0.03 to 100 μM. The concentration giving 50% inhibition was calculated from the inhibition curve.
*Shown to be farnesylated in vivo.

3. Discussion

The current data extend the observations on the p21$^{ras}$ farnesyl:protein transferase set forth in Example I, and further indicate that the recognition site for this enzyme is restricted to four amino acids of the Cys-A1-A2-X type. As a reference sequence for these studies, the peptide CVIM was used. This peptide inhibited the farnesyl:protein transferase by 50% at a concentration of 0.15 μM. Substitution of various amino acids into this framework yielded peptides that gave 50% inhibitions at a spectrum of concentrations ranging from 0.025 μM (CVFM) to greater than 50 μM (FIG.14).

In general, the highest inhibitory activities were achieved when the A1 and A2 positions were occupied with nonpolar aliphatic or aromatic amino acids. This stringency was more severe at the A2 than at the A1 position. Thus, peptides containing lysine or glutamic acid at the A1 position gave 50% inhibition at 0.7 and 1.5 μM, respectively. When these two residues were inserted at the A2 position, the affinity for the enzyme declined by more than 50-fold. Glycine and proline lowered inhibitory activity moderately at the A1 position (50% inhibition at 4 and 8 μM) and somewhat more severely at the A2 position (8 and 20 μM).

The X position showed the highest stringency. In the context of CVIx, methionine was the preferred residue but phenylalanine and serine were tolerated with only modest losses in activity (0.5 and 1 μM, respectively). Aliphatic resides and proline were disruptive at this position, with 50% inhibitions in the range of 5-11 μM. Glutamic acid, lysine, and glycine were not tolerated at all; 50% inhibition required concentrations above 40 μM.

A study of tetrapeptides corresponding to the COOH—termini of known proteins (Table III) gave results that were generally in keeping with those obtained with the substituted CVIM peptides. They provided the additional information that glutamine and cysteine are well tolerated at the X position (CCVQ and CIIC). All of the proteins that are known to be farnesylated in intact cells (indicated by the asterisks in Table III) followed the rules outlined above, and all inhibited farnesylation at relatively low concentrations (5 μM or below) with the exception of the CTVA sequence, R. toruloides (19). This peptide inhibited the rat brain farnesyl:protein transferase by 50% only at the high concentrations of 30 μM. It is likely that the farnesyl:protein transferase in this fungal species has a different specificity than that of the rat brain.

The peptide CAIL, which corresponds to the COOH—terminus of the γ-subunit of bovine brain G proteins (20,21), did not compete efficiently with $p21^{H-ras}$ for farnesylation (Table III). A 50% inhibition at the highest concentration tested (100 μM) was observed. The inhibitory activity was lower than that of CVIL (12 μM) or CAIM (0.15 μM). Thus, the combination of alanine at the A1 position and leucine at the X position is more detrimental than either single substitution. This finding is particularly relevant since the gamma subunit of G proteins from human brain (22) and rat PC12 cells (23) have been shown to contain a geranylgeranyl rather than a farnesyl. These findings suggest the existence of a separate geranylgeranyl transferase that favors CAIL and perhaps other related sequences.

The studies with the biotinyated heptapeptide (FIG. 12B) confirm that at least some of the short peptides act as substrates for the enzyme. The saturation curves relating reaction velocity to the concentration of either $p21^{H-ras}$ or the biotinylated heptapeptide are complex and sigmoidal. The inhibition curves with the various peptides differ from classic competitive inhibition curves. Finally, as mentioned in Example I, the maximal velocity of the purified enzyme is relatively low. These findings suggest that the binding of the peptides to the enzyme is not a simple equilibrium reaction. Rather, there may be a slow binding that requires conformational change.

The observation that the A1 position shows a relaxed amino acid specificity suggests that the residue at this position may not contact the, farnesyl transferase directly. Rather, the contacts may involve only the cysteine and the residues at the A2 and X positions. A working model for the active site of the farnesyl:protein transferase places the peptide substrate in an extended conformation with a largely hydrophobic pocket of the enzyme interacting with the X group of the CAAX-containing substrate.

EXAMPLE III

RECOMBINANT CLONING OF THE FARNESYL: PROTEIN TRANSFER α AND β SUBUNIT cDNAs

This example demonstrates the recombinant cloning of cDNAs corresponding to both the α and β subunit of rat farnesyl:protein transferase. The method employed by the inventors involved the application of the peptide sequence information, as detailed above, to prepare specific primers for PCR-based sequencing, which sequences were then used for the construction of probes with which to screen cDNA libraries. The cloning of each of these cDNAs by the inventors' laboratory has recently been reported (36, 36a).

1. Methods
a. General Methods

General molecular biological techniques were employed in connection with the cloning reactions described below, as set forth in Sambrook et al., (ref 24). cDNA clones were subcloned into bacteriophage M13 or plasmid pUC vectors and sequenced by the dideoxy chain termination method (25) using the M13 universal sequencing primer or gene specific internal primers. Sequencing reactions are preferably performed using a modified bacteriophage T7 DNA polymerase (26) with $^{35}$S-labeled nucleotides, or Taq polymerase with fluorescently labeled nucleotides on an Applied Biosystems Model 370A DNA Sequencer.

For the isolation of total cellular RNA from rat tissues, the inventors preferred to employ the guanidinium thiocyanate/CsCl centrifugation procedure (27). Whereas for the isolation of RNA from cell lines, the quanidinium HCl method was found to be preferrable (28). The isolation of poly A+ RNA by oligo(dT)-cellulose chromatography was achieved by the methods described in Refs. 24 and 29. Northern blot hybridization using single-stranded $^{32}$P-labeled probes was carried out as described by Lehrman et al. (30). A cDNA probe for rat glyceraldehyde-3-phosphate dehydrogenase was kindly provided by Karl Normington, (University of Texas Southwestern Medical Center at Dallas).

Polyclonal antisera, specific for either the α or β subunit of farnesyl transferase, were prepared by immunising rabbits with synthetic peptides derived from each specific subunit. Antibody Y533 was raised against a synthetic peptide with the sequence LQSKHSRES-DIPASV, derived from the predicted amino acid sequence of a cDNA clone of the e subunit. Antibody X287 was raised using the synthetic peptide IQATTHFLQKPVPGFEE, derived from a tryptic digest of the B subunit. Each peptide was coupled to Keyhole Limpet hemocyanin using maleimidobenzoic acid N-hydrosuccinimide ester (Signa Chemical Co.) (40). For each antibody, three New Zealand White rabbits were immunised with 600 μg of coupled peptide in Freund's complete adjuvant. Immunoblot analysis was performed as described in (35, 36).

Rat PC12 pheochromocytoma cells, rat KNRK cells (CRL 1569), and human embryonic kidney 293 cells were obtained, respectively, from Thomas Südhof (University of Texas Southwestern Medical Center at Dallas), the American Type Culture Collection, and Arnold J. Berk (University of California, Los Angeles).
b. PCR and Probe synthesis To derive a sequence for constructing an appropriate probe, rat genomic DNA may be used as a template for PCR as described by Saiki et al. (31) and Lee et al. (32). The approach used by the inventors was to sequence a portion of the α or β subunit genes through the use of appropriate PCR primers, based on a consideration of the peptide sequences (shown in Table I). Thus, PCR was used to obtain the rat genomic DNA sequences that encoded tryptic peptides derived from either the purified α or β subunits of rat farnesyl transferase (FIG. 16). For the both the α and β sequences, the PCR primers were synthesized based on the $NH_2$- and COOH—terminal sequences of the peptides shown in FIG. 16, and included the degenerate inosine codons indicated (FIG. 16). PCR primers were end-labeled with [γ-$^{32}$P]ATP. Each of the amplified DNA fragments were eluted from 12% acrylamide gels and sequenced by the method of Maxam and Gilbert (33). Translation of the nucleotide sequences between the two primers yielded peptides with amino acid sequences identical to those of the peptides shown (FIG. 16).

Using the DNA sequences of the PCR products, the inventors then synthesized an oligonucleotide probe that would hybridize with the region corresponding to the peptide, for use in the direct screening of the library. For the α subunit, a 38-mer probe with the nucleotide sequence: 5'-ATIGAGTTAAACGCAGCCAAC-TATACGGTCTGGCACTT-3', was synthesised. Whereas for the β subunit, two primers, designated primer β3 and primer β4 were synthesied with the respective nucleotide sequences: 5'-GCGTACTGTGCGGCCTC-3' and 5'-GGCCTCAGTAGCCTCTCTCACCAAC-3'.

The primers for the β subunit were used for 3'-end amplification of cDNA as described by Frohman et al. (34). Poly(A)+ RNA from rat KNRK cells was reverse transcribed using a (dT) $_{17}$-adaptor, 5'-GACTCGAGT-CGACATCGA(T) $_{17}$-3'. The 50 μl reaction mixture, containing 4 μg poly(A)+ RNA, 2.5 μg (dT) $_{17}$-adaptor, and 100 units of Moloney murine leukemia virus reverse transcriptase (Bethesda Research Laboratories), was incubated at 37° C. for 1 hour. Reverse transcribed cDNA was diluted 50-fold with 10mM Tris-HCl at pH 8.0, 1 mM EDTA, and subjected to specific PCR amplification as follows. 10 μl of diluted cDNA, 25 pmol of adaptor primer (5'-GACTCGAGTCGACATCG-3'), and 25 pmol of primer 3 were boiled, after which PCR was carried out for 40 cycles (95° C., 40 sec; 58° C., 1 min; 72° C., 3 min) with TaqI polymerase. Amplified PCR products were subjected to electrophoresis on an agarose gel, transferred to a nylon membrane, and probed with $^{32}$P-labeled primer 4. The hybridizing DNA fragment was eluted, extracted with phenol/chloroform, and used as a template for a second PCR reaction. The reaction using 25 pmol each of adaptor primer and primer 4 was carried out with the same amplification protocol as described above. The reamplified DNA fragment was gel-purified, cleaved with RsaI or TaqI, and subcloned into an M13 vector for DNA sequencing and for subsequent generation of the single-stranded M13 probe that is referred to as Probe B. The DNA sequence of the PCR-derived clone was also used to generate a 50-mer oligonucleotide probe that is designated Probe A. Probes A and B were then used to screen cDNA libraries in order to obtain a full-length β subunit cDNA (see β subunit cloning section, below).

c. cDNA Libraries and Cloning

Rat PC12 cell poly(A+) RNA and oligo (dT)-primed KNRK cell double-stranded cDNA libraries were constructed in bacteriophage λgt10, using a cDNA synthesis kit from Invitrogen. These cells were preferred because the inventors believed them to be rich in farnesyl:-protein transferase mRNA. Although numerous convenient methods are known for the construction of cDNA libraries, the inventors utilised the above kit from Invitrogen as they thought it to be a particularly convenient method. The cDNA itself was prepared using both oligo(dT)- and random hexamer-primed cDNA, then ligated to a suitable linker, with the EcoR1/Not1 linker being preferred in this case. cDNAs larger than 1 kb were isolated by size fractionation using a 1% agarose gel and ligated into EcoR1-cleaved λgt10 DNA (Stratagene), in order to complete the construction of the cDNA-containing vectors for library preparation. After in vitro packaging of the recombinant lambda phage with a DNA packaging extract (Stratagene), phage were plated out on host strain E. coli C600 hfl−cells.

α subunit cloning.

Approximately 1×10$^6$ plaques of the rat brain library were screened. Duplicate filters were hybridized in 6×SSC (1×SSC=150 mM NaCl/15 mM Na citrate, at pH 7.0) with 1×10$^6$ cpm/ml of $^{32}$P-labeled probe (see above). One positive clone, λRB-17, with an insert of 1.4 kb was identified and plaque purified. Phage DNA from a plate lysate was subcloned into bacteriophage M13 and pBluescript vectors for DNA restriction mapping and sequencing (37).

As the clone first obtained was not a full-length clone, 5'-end amplification was employed to produce the complete sequence, as described in Ref 34. Firstly, an M13 probe corresponding to the 5' end of λRB-17 was used to screen the KNRK cell library. Replicate filters were hybridized in 50% (v/v) formamide containing 1×10$^6$ cpm/ml of the probe. Positive clones were analyzed by PCR, and the clone with the longest insert (λKNRK-3) was purified and subcloned for analysis. A 5' Rapid Amplification of cDNA End procedure (5' RACE) (34) was used to extend the 5' end of λKNRK-3. An M13 probe derived from the amplification product (RACE-5') was then used to screen a rat testis library (purchased from Clontech), yielding λRTH, which extended to nucleotide position 53.

To obtain the extreme 5λend of the cDNA, a primer-extension λgt10 library was constructed from rat testis poly(A)+RNA. First stand synthesis was primed with an oligonucleotide corresponding to a sequence near the 5'-end of RACE-5' using Maloney murine leukemia virus reverse transcriptase. After incubation at 37° C. for 1 h, the reaction was heated at 70° C. for 5 min. Five units of Thermostable rTth Transcriptase (Perkin-Elmer) was then added, and the reaction continued at 70° C. for 30 min. After second strand synthesis, the cDNAs were ligated to an EcoRI/NotI linker. Excess linkers were removed by Centricon 100 Microconcentrator (Amicon). Approximately 5×10$^5$ plaques were screened with a $^{32}$P-labeled probe corresponding to nucleotides 54–104, which was obtained from the sequence of λRTH. Twenty-five positive clones were identified. Phage DNA was prepared from plate lysates, and the insert from one of the longest clones, λPE-7, was subcloned for sequencing (37).

β subunit cloning.

Approximately 5×10$^5$ plaques were transferred to replicate filters. One filter was hybridized in 10% (v/v) formamide with 1×10$^6$ cpm/ml of a $^{32}$P-labeled 50-mer oligonucleotide probe (Probe A; described above). The other filter was hybridized in 50% formamide with 1 × 10⁶ cpm/ml of a single-stranded M13 probe (Probe B; described above). One positive clone (λdT-7) with an insert of ~2.3 kb was identified with both probes and plaque purified. Phage DNA isolated from the plate lysate of λdT-7 was subcloned into M13 and pUC vectors for sequencing and restriction mapping.

To obtain the extreme 5' end of the cDNA, an M13 probe corresponding to the 5' end of λdT-7 was used to screen a rat brain "5'-stretch" cDNA library (purchased from Clontech). Replicate filters were hybridized in 50% formamide containing 1×10⁶ cpm/ml of the probe. Of the 5×10⁵ plaques screened, six positive clones were plaque purified and eluted in 0.2 ml buffer containing 100 mM NaCl, 8 mM MgSO₄, 50 mM Tris-HCl at pH 7.5, and 0.01% (w/v) gelatin. A primer corresponding to the right arm or left arm of λgt10 sequences flanking the unique EcoR1 cloning site was used in combination with a primer derived from the 5' end of the rat protein farnesyl transferase cDNA (λdT-7) for a PCR reaction. PCR products were analyzed on an agarose gel, and the clone containing the longest extension, λRB-23, was subcloned for further analysis.

d. Expression vectors

Expression vectors for the α subunit of rat farnesyl transferase were constructed in pCMV5, a plasmid that contains the promoter-enhancer region of the major immediate early gene of human cytomegalovirus (38). A PvuII fragment containing 20 base pairs of the 5' untranslated region and the entire coding region was excised from clone λRTH-B and ligated into SmaI-digested pCMV5 in both orientations. Plasmid λRTH-B is identical to λRTH except for the presence of an intron in the 5'-untranslated region at nucleotide position 39, upstream of the PvuII site at position 37-42. The resulting plasmids designated pFT-α (correct orientation) and pFT-αrev (reverse orientation), were characterized by restriction mapping.

Expression vectors for the β-subunit of rat farnesyl transferase were also constructed in pCMV5 (38). An EcoR1 fragment containing the entire 5' untranslated region and the coding region of farnesyl transferase β subunit cDNA was excised from clone λRB-23 and ligated into EcoR1-digested pCMV5 in both orientations. The resulting plasmids, designated pFT-β1 (correct orientation) and pFT-β1rev (reverse orientation), were characterized by restriction mapping.

e. DNA Transfection

Human embryonic kidney 293 cells were grown in monolayer at 37° C. in medium A (Dulbecco's modified Eagle medium supplemented with 10% (v/v) fetal calf serum, 100 units/ml of penicillin, and 100 μg/ml streptomycin). On day 0, 6×10⁵ cells/100-mm dish were seeded in medium A. On day 1, each dish of cells was transfected with 3 μg of the indicated plasmid plus 1 μg of pVA (a plasmid encoding adenovirus VA RNA_I) (39) by the calcium phosphate method (24). On day 2, the cells received fresh medium A. On day 4, the cells from two dishes were harvested, pooled, and disrupted by repeated aspiration at 4° C. through a 25-gauge needle in 0.4 ml buffer containing 50 mM Tris-HCl at pH 7.5, 50 μM ZnCl₂, 3 mM MgCl₂, 20 mM KCl, 1 mM dithiothreitol, and 0.4% (w/v) octyl-β-glucopyranoside. A cytosolic extract was obtained by centrifugation at 100,000×g for 1 h at 4° C., after which 0.16 to 5.4 μg of the supernatant fraction were assayed for farnesyl transferase activity by measuring the amount of [³H]farnesyl transferred from [³H]farnesyl pyrophosphate to p21$^{H-ras}$ protein as described above.

2. Results a. α Subunit Cloning and Sequence Analysis

Degenerate oligonucleotide probes encoding the 5' and 3' ends of a tryptic peptide derived from the farnesyl transferase β subunit were used as primers in a PCR employing rat genomic DNA (FIG. 16A). The sequence of the amplified product was used as a probe to screen a random hexanucleotide-primed rat brain cDNA library cloned in λgt10. This procedure yielded λRB-17, which extended from a poly A tract up to nucleotide position 345 (this position refers to the final sequence of the mRNA, as in seq id no:2).

The 5'-end of the mRNA encoding the α subunit was found to contain a sequence extremely rich in GC basepairs (76% GC from nucleotides 71 to 205 and 90% GC from nucleotides 116 to 145). Multiple attempts to traverse this region by primer extension using reverse transcriptase gave products that terminated prematurely, or that encoded unspliced introns. Therefore, other strategies were employed in order to obtain the 5'-end of the mRNA (see above methods section for detailed protocols). A composite of the cDNA sequences thus obtained was used to generate the overall sequence of the mRNA (seq id no:2).

The mRNA was found to encode a protein of 377 amino acids (seq id no:1) with a calculated molecular weight of 44053. Although the cDNA sequence did not contain a terminator codon upstream of the first methionine codon, it is believed that this methionine represented the true initiator codon. This is supported by transfection studies, in which the recombinant protein produced was observed to have a molecular weight that was indistinguishable on immunoblots from that of the purified rat brain α subunit (see below and FIG. 20). If the cDNA were incomplete, the initiator methionine must be upstream of the 5' end of the sequence obtained, and therefore the protein produced by the cDNA should be at least 2 kDa smaller than the authentic protein. Such a difference should have been detected in gel electrophoresis experiments.

The most remarkable feature of the α subunit cDNA was determined to be a string of 9 consecutive proline residues near the NH₂-terminus (underlined in seq id no:2), whose codons accounted for much of the extreme GC-richness of this region. The mRNA contained sequences corresponding to sequences of the peptides obtained following tryptic digestion of the purified α subunit. Discrepancies only occured at positions that were assigned tentatively in sequencing trace amounts of protein (see Table I). Some slight homology has been noted between the rat α-subunit amino acid sequence and yeast RAM2, the sequence of which is reported in He et al., reference 51 (see FIG. 17).

Recently, Kohl et al. have reported the cloning of a partial cDNA clone corresponding to the bovine α-subunit of farnesyl transferase (52). The 329 amino acids encoded by this partial clone are 95% identical to the corresponding region in the α-subunit of the rat farnesyl transferase. Comparison of the complete amino acid sequence of rat farnesyl transferase α-subunit (377 amino acids) with that of the yeast RAM2 gene product (316 amino acids) disclosed by He et al. reveals that the two proteins are 39% identical in the COOH-terminal 211 residues, suggesting that RAM2 is the yeast counterpart of the α-subunit of mammalian farnesyl transferase.

b. β subunit Cloning and Analysis

Figure 16B:
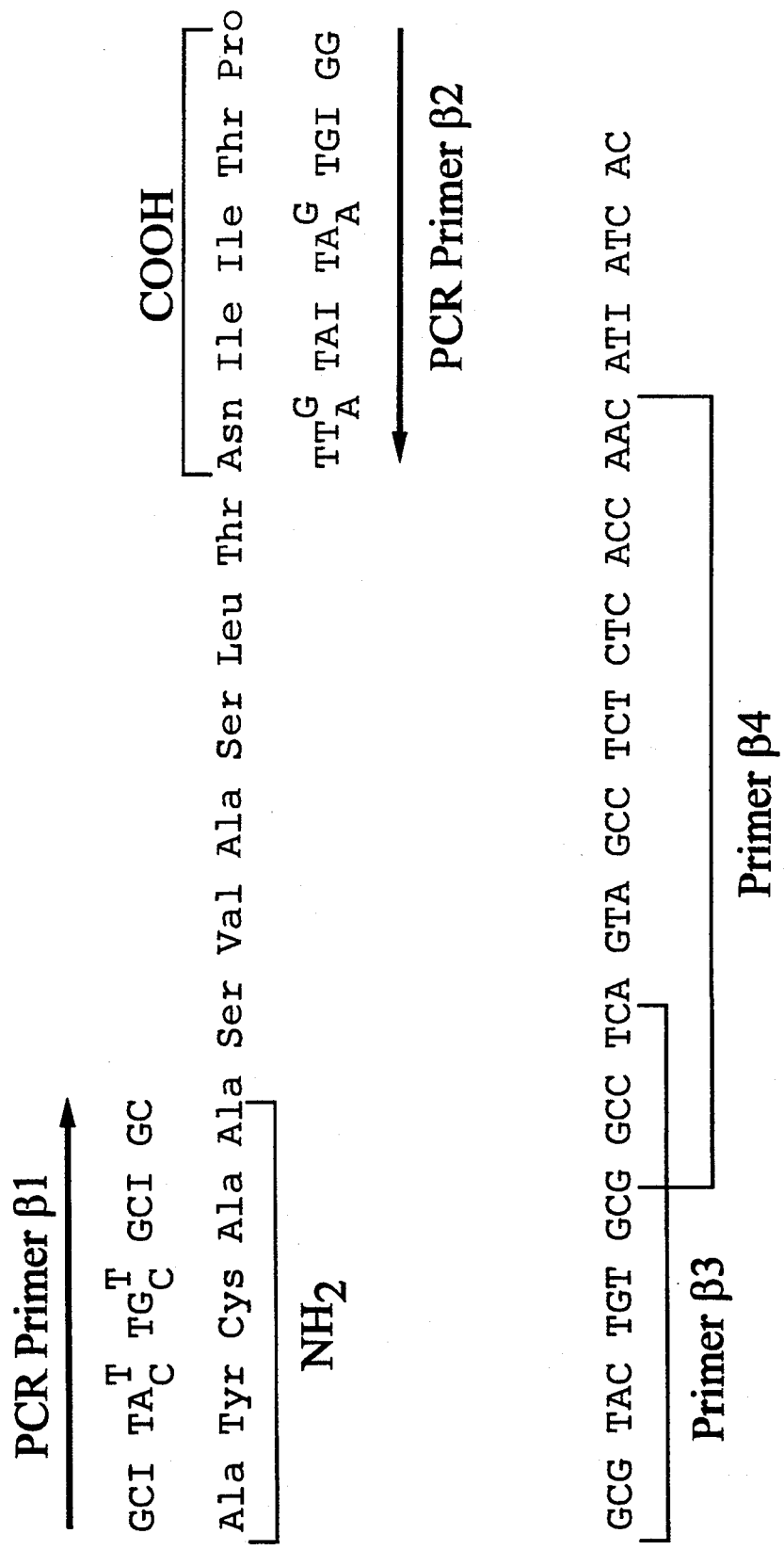
FIG. 16B (upper): Primer β1 and primer β2 were used in PCR with rat genomic DNA to generate the nucleotide sequence encoding the amino acid sequence of the peptide shown, as described in Example III.

A unique DNA sequence encoding a portion of the β subunit of the rat farnesyl transferase was obtained by the polymerase chain reaction (PCR) with rat genomic DNA and degenerate oligonucleotide primers (primers β1 and β2) corresponding to potential sequences encoding a tryptic peptide obtained from the purified rat brain enzyme (FIG. 16B). Two unique oligonucleotides (primers β3 and β4) were synthesized based on the sequence of the amplified product (FIG. 16B). These primers were then used in a 3'-end amplification strategy (34) to obtain an amplified fragment from cDNA prepared from mRNA isolated from cultured rat kidney cells (KNRK cells). This fragment was used to generate probes that identified a bacteriophage containing a near full-length cDNA (λdT-7) from a cDNA library prepared from rat pheochromocytoma PC12 cells. Finally, a fragment from the 5'-end of λdT-7 was used to identify a clone containing a full-length farnesyl transferase β subunit cDNA (kRB-23) from a rat brain cDNA library (seq id no:4).

The cDNA for the rat brain farnesyl transferase β subunit contains 59 base pairs of 5' untranslated region followed by protein-coding region of 1314 base pairs and a 3' untranslated region of 1091 base pairs (seq id no:4). The cDNA encoded a protein of 437 amino acids and contained sequences corresponding to sequences of the peptides obtained following tryptic digestion of the purified rat brain farnesyl transferase β subunit. Although certain minor discrepancies in sequence between the protein and the cDNA were apparent, these occurred near the COOH—termini of the peptides and were attributed to ambiguities in sequencing the trace amounts of peptide that were available (see Table I).

The cDNA clones did not contain an inframe terminator codon upstream of the first methionine (amino acid residue 1 in seq id no:3). This is believed to be the initiator methionine as it lies in a good context for initiation according to Kozak's rules (41) and because the cDNA encodes a protein of the same size as the β-subunit when transfected into animal cells (see below). Although λdT-7 was obtained from an oligo-dT primed cDNA library, the clone did not contain a poly A tract, nor did it contain a consensus polyadenylation sequence. However, RNA blot hybridization experiments and expression studies (see below) suggested that the clone is essentially full-length.

The molecular weight of the β subunit of the rat brain farnesyl transferase was calculated to be 48,679. The amino acid composition did not show any particularly remarkable features and the calculated isoelectric point was 5.99. An analysis of the hydrophobicity plots did not reveal any extensive hydrophobic sequences.

A search of the GenBank and EMBL data banks revealed significant resemblance to two proteins, the DPR1-RAM1 protein of yeast Saccharomyces cerevisiae and a yeast open reading frame of unidentified function (ORF2). Extensive stretches of identity were evident between the β subunit protein sequence and the yeast DPR1-RAM1 gene product (FIG. 18). Sequence conservation was observed throughout the two proteins (overall identity: 37%), but was found to lessen at both ends, and the yeast protein was shorter by six amino acids.

In a recent article by Kohl et al. (52), in a note added in proof, it is indicated that the β-subunit of bovine farnesyl transferase has been cloned and that it shares 96% homology to the rat β-subunit. However, no actual sequences corresponding to the β-subunit are disclosed by Kohl et al.

c. Northern Blotting Analysis

Figure 19A:
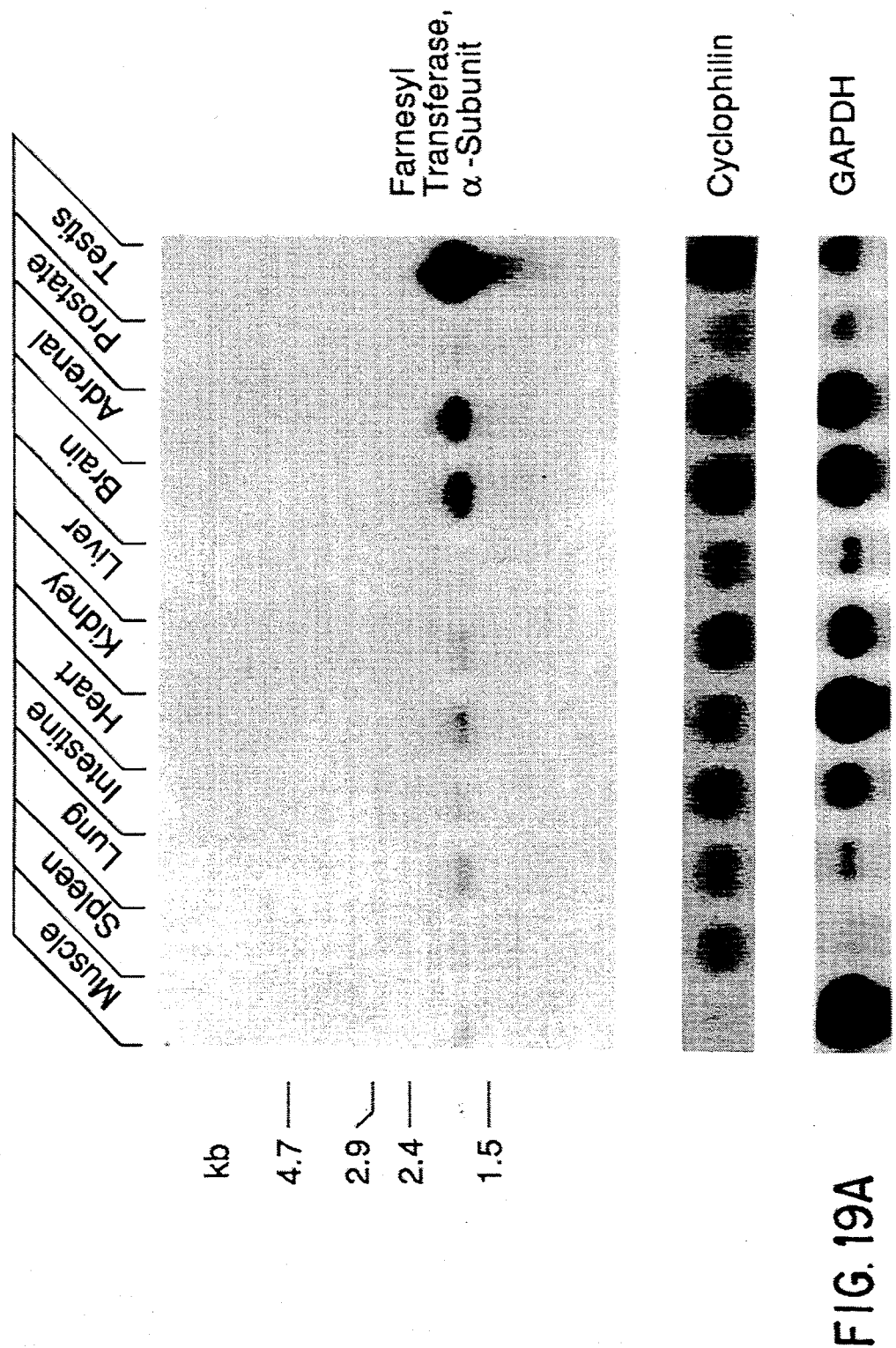
FIGS. 19A, B, C, D. Distribution of Rat Farnesyl Transferase α and β subunit mRNA in Tissues (A & C) and Cultured Cells (B & D).
Figure 19B:
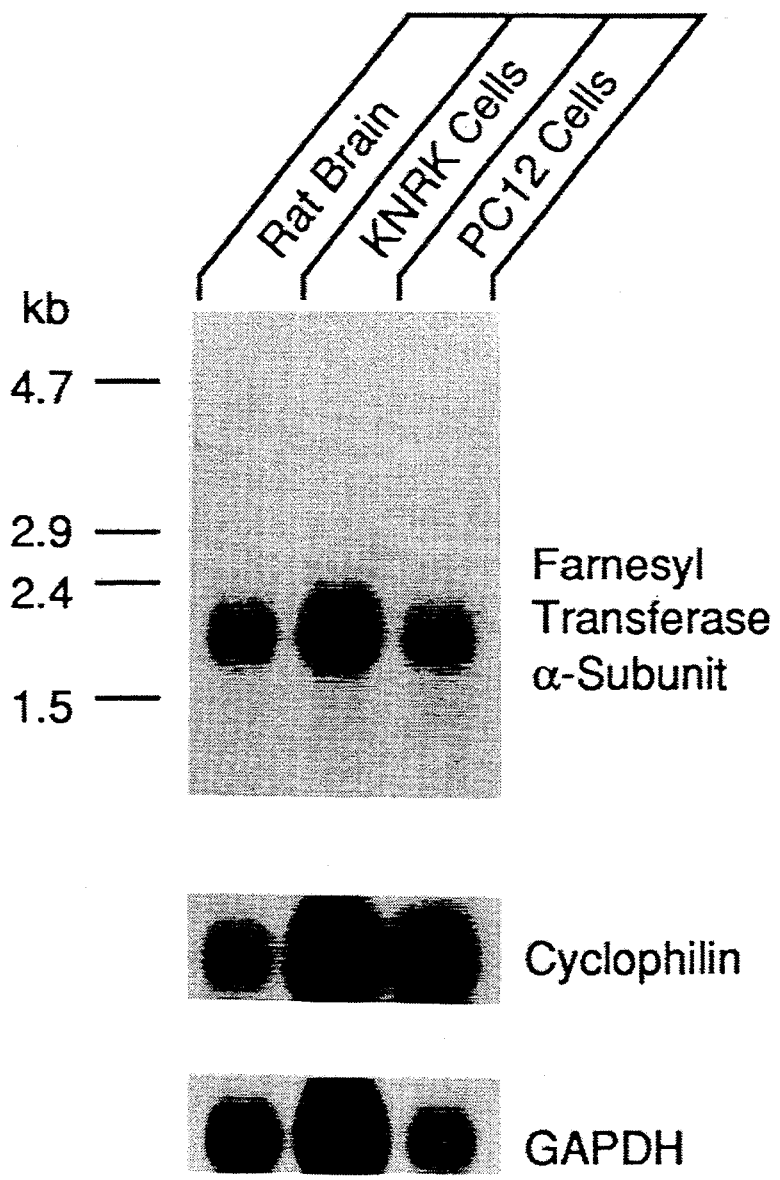
FIGS. 19B & 19D: Expression of the α (C) and β (D) farnesyl transferase subunit mRNA in rat brain, KNRK cells, and PC12 pheochromocytoma cells. An aliquot of poly(A)+ RNA from each sample (10 μg) was subjected to blot analysis as described in A & B, and exposed for 12 h at -70° C. The same filter was subsequently reprobed with a 32P-oligonucleotide derived from the rat cyclophilin cDNA sequence as described in A & B, and the filter was exposed to XAR-5 film for 12 h at -70° C.

Northern RNA blot analysis with $^{32}$P-labelled probes derived from the α subunit cDNA revealed a single mRNA of ~1.75 kb in multiple rat tissues, including lung, heart, kidney, brain, adrenal, and testis (FIG. 19A). The amount of mRNA in testis was several-fold higher than in any other tissue, an observation that was repeated on several occasions. An mRNA of the same size was also observed in two lines of cultured rat cells derived from kidney (KNRK cells) and adrenal medulla (PC12 cells) (FIG. 19B).

Figure 19C:
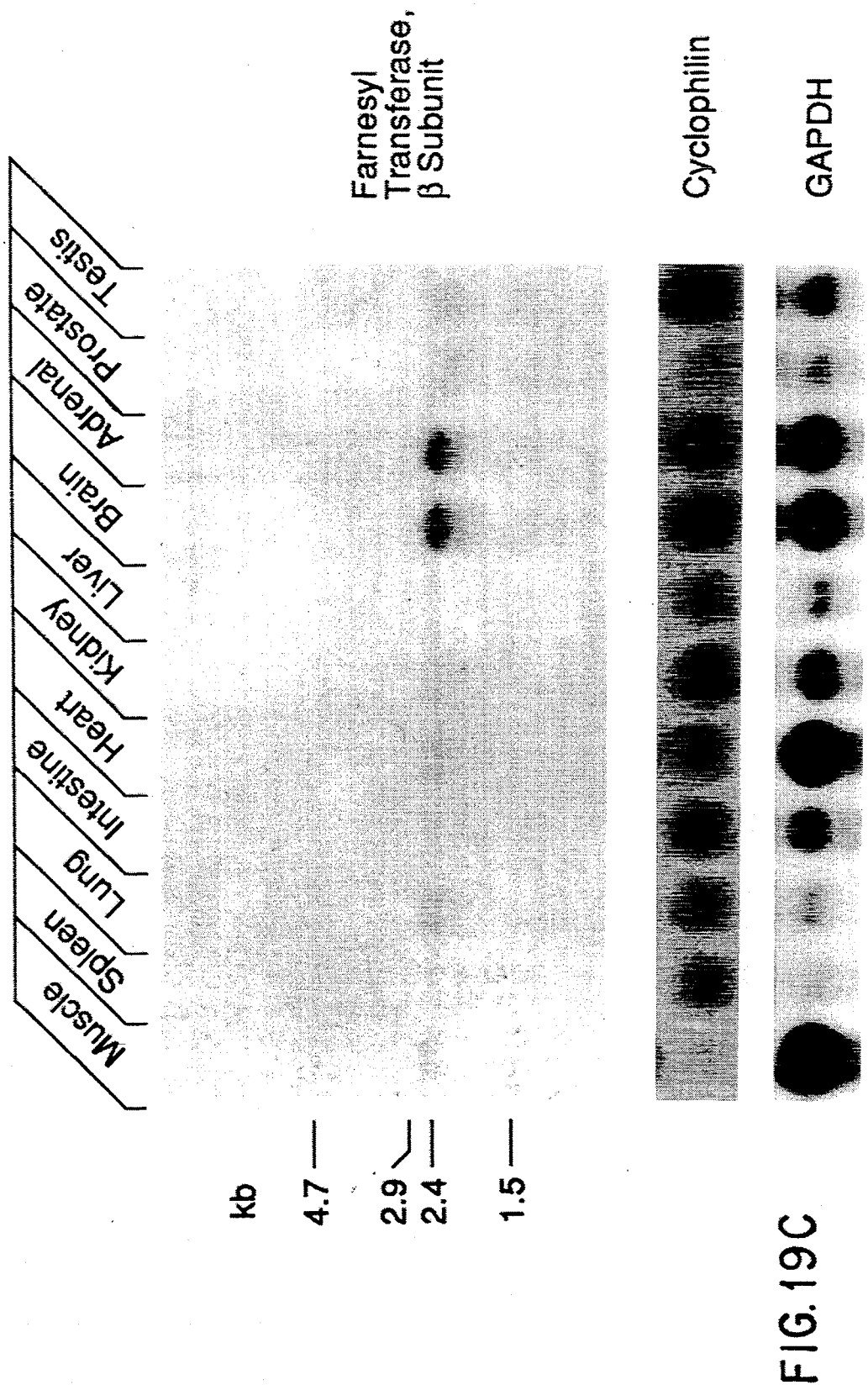

Northern RNA blot analysis with $^{32}$P-labelled probes derived from the β subunit cDNA revealed a hybridising mRNA of ~2.5 kb in all rat tissues examined except liver and spleen (FIG. 19C). Adequate amounts of mRNA from these tissues were applied to the filter as confirmed by hybridization with control probes for cyclophilin and glyceraldehyde-3-phosphate dehydrogenase. The brain and adrenal gland appeared to have somewhat more mRNA for farnesyl transferase β-subunit than did the other tissues. More quantitative studies will be required to determine whether the variations shown in FIG. 18C are significant.

Figure 19D:
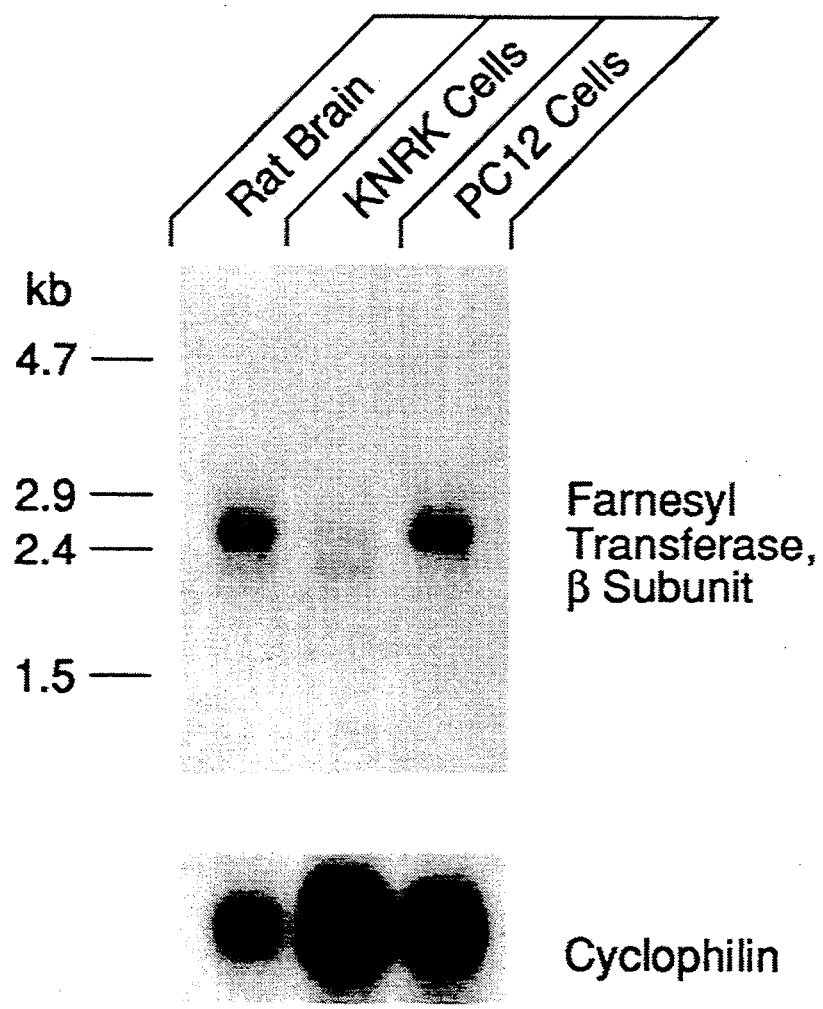

The mRNA for the farnesyl transferase β-subunit was also found in the two cultured rat cell lines from which cDNA sequences had been obtained (FIG. 19D). PC12 cells had the 2.5-kb transcript, whereas the KNRK cells had two transcripts, one of which was smaller than the 2.5-kb mRNA (FIG. 19D). It was not determined whether the smaller transcript represented another gene product that cross-hybridized with the β-subunit probe, or whether this mRNA represented alternative processing of an allelic transcript.

d. Co-Expression and Stability

The cDNA coding regions of both the α and β subunits were cloned into pCMV mammalian expression vectors in either the correct or the reverse orientation. The cDNAs were introduced into human kidney 293 cells by calcium phosphate-mediated transfection, and the proteins were detected by immunoblotting with specific antibodies against the α and β subunits. In both cases, the cDNA directed the expression of proteins with molecular weights that were indistinguishable on immunoblots from those of the purified rat brain farnesyl transferase α and β subunits (FIG. 20).

Figure 20A:
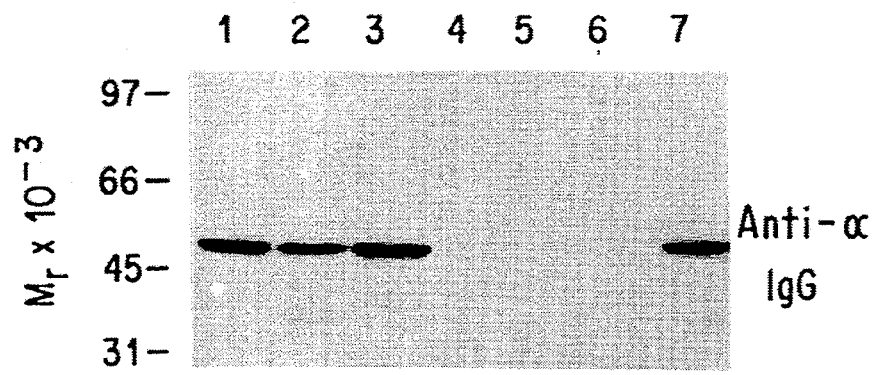
FIG. 20A,B. Immunoblot Analyses of α and β-subunits of Rat Protein Farnesyl Transferase Expressed in Transfected 293 cells. Samples were subjected to SDS/PAGE on 10% gels and transferred to nitrocellulose. The filters were incubated with either 1 μg/ml of rabbit anti α subunit IgG-Y533 (FIG. A) or 5 μg/ml of rabbit anti β-subunit IgG-X287 (FIG. B) followed by incubation with $^{125}I$-labeled goat anti-rabbit IgG ($1 \times 10^6$ cpm/ml). Lanes 1 and 3, 20 μg of partially purified Mono Q fraction of rat brain farnesyl transferase. Lanes 2 4,5,6,7, 20 μg of cytosol from 293 cells transfected with the following plasmids: pFT-α plus pFT-β1(lanes 2 and 7); pFT-α plus pFT-β1rev (lane 4); pFT-αrev plus pFT-β1 (lane 5); pFT-αrev plus pFT-β1rev (lane 6). The filters were exposed to Kodak XAR-5 film for 48 h (FIG.A) or 16 h (FIG. B) at -70° C. Molecular weight markers are indicated. Plasmids pFT-αrev and pFT-β1rev contain cDNAs inserted in the reverse (noncoding) orientation.
Figure 20B:
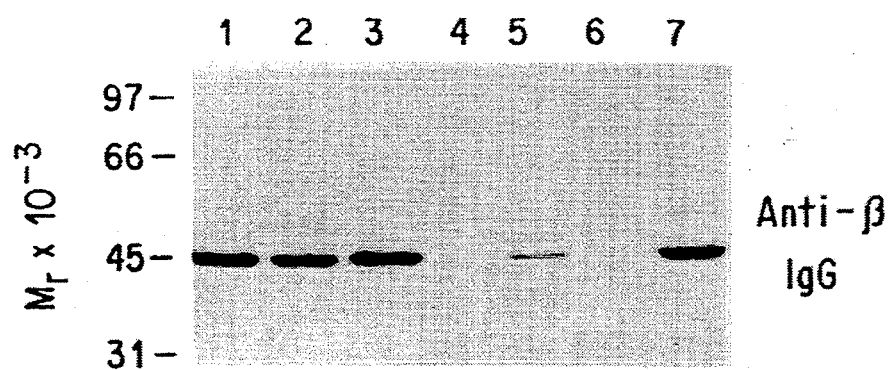
Figure 21:
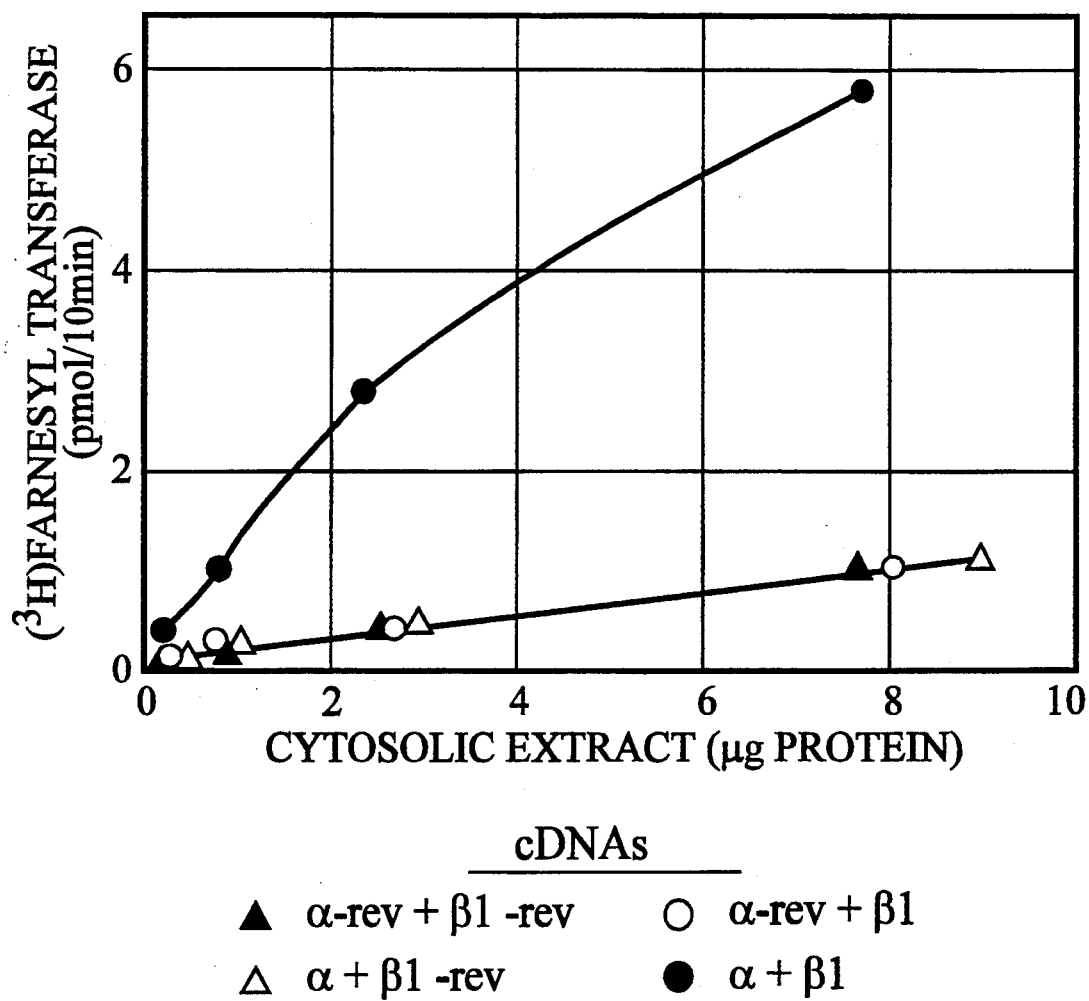
FIG.21. Farnesyl Transferase Activity of Cytosolic Extracts from 293 cells Transfected with cDNAs Encoding the α and β Subunits of Rat Protein Farnesyl Transferase in the Correct or Reverse (rev) Orientations. Cells were transfected with 3 μg of the indicated plasmid plus 1 μg pVA. Each assay contained in a final volume of 25 μl the indicated amount of cytosolic extract, 50 mM Tris-chloride (pH 7.5), 50 μM $ZnCl_2$, 20 mM KCl, 3 mM $MgCl_2$, 1 mM dithiothreitol, 0.4% (v/v) octyl-β-glucopyranoside, 40 μM $p21^{H-ras}$, and 15 pmol of all-trans [$^3H$]farnesyl pyrophosphate (15,335 dpm/pmol). Assay tubes were incubated at 37° C. for 10 min, after which the amount of [$^3H$]farnesyl attached to $p21^{H-ras}$ was measured. Each value is the average of duplicate incubations.

The accumulation of detectable amounts of α subunit required simultaneous transfection with a properly oriented cDNA encoding the β-subunit (FIG. 20A). Similarly, the amount of detectable β-subunit was increased by transfection with the α subunit cDNA in the correct orientation (FIG. 20B). Transfection with the two cDNAs in the correct orientation was also required in order to produce significant amounts of p21$^{ras}$ farnesyl transferase activity as measured in cytosolic extracts (FIG. 21).

3. Discussion

The delineation of the amino acid sequence of the α subunit has not yet allowed its catalytic role to be precisely identified. Homology searches of protein databases failed to reveal significant resemblance of the α subunit to other proteins except for proteins that contain long stretches of prolines. These include such apparently unrelated proteins as the catalytic subunits of rat and human protein phosphatase 2B, mouse retinoblastoma-associated protein pp105, and *Dictyostelium discoideum* protein tyrosine kinase-1. The α subunit does not bear significant structural resemblance to known prenyltransferases such as mammalian farnesyl pyrophosphate synthetase or yeast hexaprenyl pyrophosphate synthetase.

Present evidence suggests that the α subunit may be shared with another prenyltransferase with a different β subunit that exhibits geranylgeranyltransferase activity (35). If the shared α subunit is stable only as a complex with one of several β subunits, this mechanism would assure that cells maintain only enough α subunits to satisfy all of the β subunits, thereby avoiding accumulation of excess α subunits, which might be toxic (36a).

The above data reveal that the α and β subunits of the rat farnesyl transferase do not exhibit farnesyl transferase activity when expressed by themselves in transfected human 293 cells. However, co-expression of the two subunits results in the production of an active enzyme. Such expression data provides support for the previous conclusion that the farnesyltransferase is a heterodimer that requires both the α and β subunits for catalytic activity (35).

Furthermore, the transfection experiments indicate that mammalian cells will not accumulate high levels of either subunit of the farnesyltransferase unless the other subunit is present. This is particularly true for the α subunit, whose accumulation was nearly completely dependent on co-expression of the β subunit. It is likely that the α subunit is rapidly degraded unless the β subunit is present. However, until pulse-chase labeling experiments are performed, the possibility of control at the level of mRNA stability or translation cannot be ruled out.

The similarity between the rat β subunit and the previously reported sequence of the yeast DPR1-RAM1 gene product (42) indicates that the latter is the yeast equivalent of the peptide-binding subunit of the mammalian farnesyl transferase. These findings confirm the previous suspicion that the yeast gene encodes one of the subunits of the farnesyl transferase and explains the failure of this protein to exhibit farnesyl transferase activity when expressed alone in $E.\ coli$ (44,45).

Mutations at a second locus, designated RAM2, also disrupt farnesyl transferase activity in yeast (44). The defect in the RAM2 cells is complemented by mating with the DPR1-RAM1 mutant. This finding suggests that the RAM2 gene product is the α subunit of the yeast farnesyl transferase. A more recent report of He et al (51) indicates that coexpression of the RAM1 and RAM2 genes in $E.\ coli$ provided extracts that farnesylated synthetic a-factor substrate. However, when extracts from separate clones were mixed, only partial farnesyl transferase activity, on the order of about 3.5%, was recovered.

An inspection of the conserved sequences in the rat β subunit and the DPR1-RAM1 protein fails to reveal any obvious candidates for the peptide binding site. The rat protein does contain the sequence LXDDXXE (residues 35–41), which resembles a sequence in four polyprenyl synthetases (I,L,orV)XDDXXD that is believed to be a prenyl pyrophosphate binding site (46). This sequence is not found in the same position in the DPR1-RAM1 protein, and its significance in the β subunit is uncertain. Although the farnesyl transferase reaction requires two divalent cations ($Mg^{++}$ and $Zn^{++}$), the sequence of the β subunit does not reveal any obvious metal binding sites.

Recently, the inventors have explored the separate catalytic roles of $Zn^{2+}$ and $Mg^{2+}$ and the specificity of the prenyl pyrophosphate binding site of the rat brain protein farnesyltransferase, using a purified enzyme preparation. In summary, it was found that the binding of $p21^{H-ras}$ to the enzyme was abolished by dialysis against EDTA and restored by addition of $ZnCl_2$ as demonstrated by chemical crosslinking. The binding of the other substrate, all-trans farnesyl pyrophosphate, was independent of divalent cations, as demonstrated by gel filtration. Transfer of the enzyme-bound farnesyl group to the bound $p21^{H-ras}$ required $Mg^{2+}$. Geranylgeranyl pyrophosphate bound to the prenyl pyrophosphate binding site with an affinity equal to that of farnesyl pyrophosphate, but the geranylgeranyl group was not transferred efficiently to $P21^{H-ras}$. It also was not transferred to a modified $p21^{H-ras}$ containing COOH-terminal leucine a protein that was shown previously to be a good substrate for a rat brain geranylgeranyltransferase (35). The inventors conclude that the protein farnesyltransferase is a metalloenzyme that most likely contains $Zn^{2+}$ at the peptide-binding site. It thus resembles certain metallopeptidases, including carboxypeptidase A and the angiotensin-converting enzyme. Strategies previously developed to screen for inhibitors of those enzymes will likely aid in the search for inhibitors of the protein farnesyltransferase.

Thus, these data establish several new points about the enzymology of the protein farnesyltransferase from rat brain: 1) the enzyme contains a tightly bound divalent cation, most likely $Zn^{2+}$, that can be removed by dialysis against EDTA; 2) $Zn^{2+}$ is essential for binding of the peptide substrate, and therefore it is probably attached to the β-subunit; 3) the enzyme binds FPP and GGPP with comparable affinities, but transfers only the farnesyl group and only to an acceptor whose CaaX sequence ends in methionine, serine, glutamine, or cysteine, but not leucine; 4) binding of prenyl pyrophosphates does not require any cation; and 5) transfer of the bound farnesyl group to the bound peptide acceptor requires $Mg^{2+}$.

Figure 22:
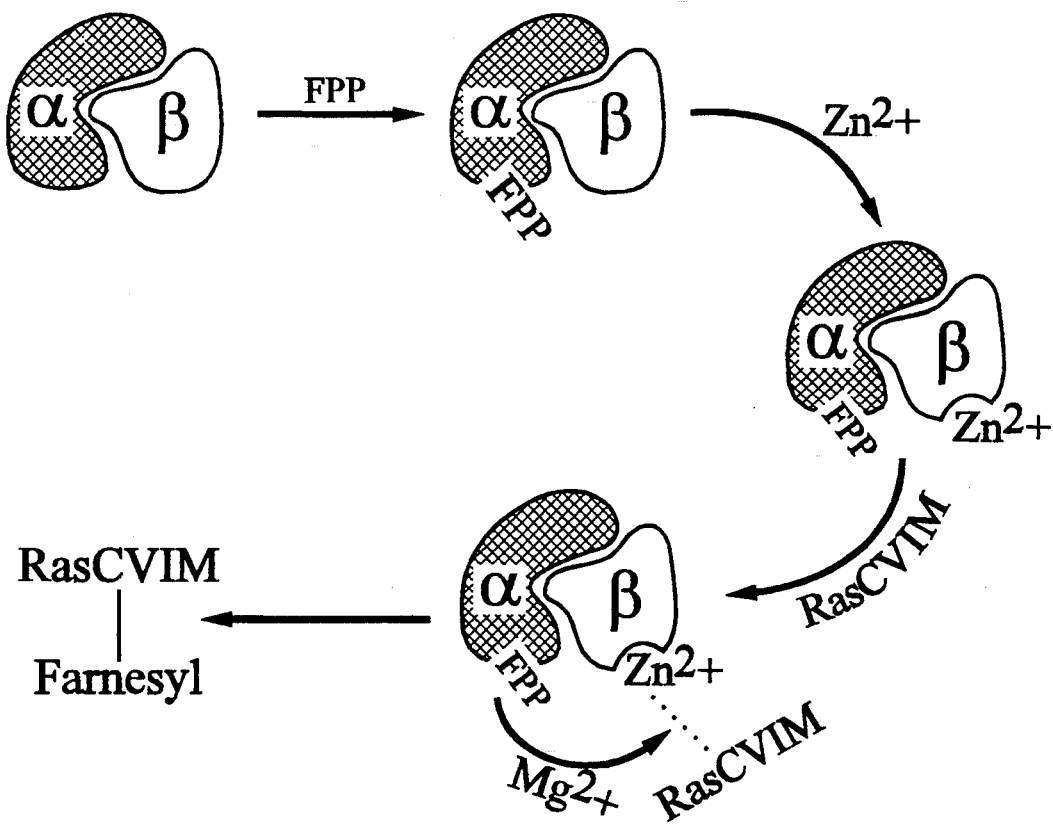
FIG. 22. Schematic diagram of the reaction sequence for EDTA-treated protein farnesyltransferase.

The reaction sequence for the EDTA-treated protein farnesyltransferase is summarized graphically in FIG. 22. The EDTA-treated enzyme binds FPP without a requirement for prior $Zn^{2+}$ binding. Peptide binding requires $Zn^{2+}$, but is independent of FPP binding. After both substrates are bound, the transfer reaction occurs in a $Mg^{2+}$-dependent fashion. In the cell the enzyme is expected to be consitutively complexed with $Zn^{2+}$. Under these conditions the mechanism is a simple random-ordered, two-substrate reaction in which the FPP and peptide acceptor can bind to the enzyme in any order.

The requirement for $Zn^{2+}$ in peptide binding is reminiscent of the requirement for $Zn^{2+}$ in certain metallopeptidases, such as carboxypeptidase A (54). In this case the $Zn^{2+}$ coordinates with the carbonyl and amino groups in the peptide bond that will be broken. In the farnesyltransferase the $Zn^{2+}$ is likely to coordinate with the cysteine sulfhydryl group on the acceptor peptide. If this postulated mechanism is correct, inhibitors that mimic peptides that coordinate with $Zn^{2+}$ might be effective inhibitors of the farnesyltransferase. This strategy would be very similar to the strategy followed in the design of inhibitors of the angiotensin-converting enzyme, a zinc metalloenzyme that is mechanistically similar to carboxypeptidase A (55).

The ability of GGPP to compete with FPP for the prenyl pyrophosphate binding site on the protein farnesyl-transferase creates potential regulatory problems for the cell. If the intracellular concentrations of FPP and GGPP are similar, then the farnesyltransferase might be competitively inhibited at all times. It seems likely that the concentration of GGPP in the cell is lower than that of FPP. FPP is an intermediate in the synthesis of cholesterol, which is the bulk product of the pathway (56). GGPP, on the other hand, is not known to be converted into any other metabolites in animal cells, and indeed its existence in animal cells was not appreciated prior to the discovery of geranylgeranyl-modified proteins (57,58). Thus, it seems likely that cells avoid GGPP competition by maintaining the FPP concentration at a higher level than the GGPP concentration.

If the α-subunit is involved in prenyl phrophosphate binding and if the α-subunit of the farnesyltransferase is identical to that of the leucine-recognizing geranylgeranyltransferase, then the α-subunit must behave differently when it is part of the geranylgeranlytransferase. It seems unlikely that the geranylgeranyltransferase would be inhibited by FPP because this would render the enzyme functionally inactive in the cell. Resolution of this issue will require the purification of the leucine-recognizing geranylgeranyltransferase and the determination as to whether its α-subunit is identical to, or merely similar to, the α-subunit of the farnesyltransferase.

The binding of prenyl pyrophosphates to the farnesyltransferase appears to be independent of divalent cations. In this regard the farnesyltransferase resembles the prenyltransferase that catalyzes the condensation of isopentenyl pyrophosphate with allylic pyrophosphates to form FPP (59). The two enzymes also resemble each other in the requirement for a divalent cation ($Mg^{2+}$ or $Mn^{2+}$) in the transfer reaction. In studies not shown, it was found that $Mn^{2+}$ will substitute for $Mg^{2+}$ in the protein farnesyltransferase reaction. The two enzymes differ in that the FPP synthetase is a homodimer and it shows no requirement for $Zn^{2+}$ (60).

Turning to the issue of the yeast counterpart prenyl transferases, very recently two additional putative β subunits of yeast prenyltransferases have been identified, BET2 (47) and CAL1 (48). Both sequences resemble the DPR1/RAM1 gene product and the β subunit of the rat brain farnesyl transferase. A mutation in the BET2 gene prevents the membrane attachment of two small GTP binding proteins (YPT1 and SEC4) that direct vesicular traffic in the yeast secretory pathway (47). These proteins terminate in the sequence CC, which has recently been shown to be geranylgeranylated in animal cells (49). The second putative β-subunit, encoded by the CAL1 gene, is necessary for yeast to control the cell cycle when deprived of calcium. Based on a genetic argument, it has been suggested that the targets for this prenyltransferase are two proteins that end in a Cys-X-X-Leu sequence and are believed to be geranylgeranylated (48).

Considered together, the yeast and animal experiments suggest the existence of a family of closely related β subunits that mediate peptide binding to a variety of prenyltransferases. Whether all of these enzymes have the same α subunit, or whether a family of such subunits also exists, remains to be determined.

EXAMPLE IV

RECOMBINANT CLONING OF THE HUMAN FARNESYL: PROTEIN TRANSFERASE α AND β SUBUNIT cDNAs

The inventors have now succeeded in cloning the cDNAs for the human counterpart of both the α and β subunits of the farnesyl:protein transferase gene. This was carried out using standard molecular cloning techniques with the aid of the information gained from the rat farnesyl:protein transferase gene disclosed above.

To clone the human α-subunit cDNA, an M13 probe of 200 to 300 nucleotides corresponding to the 5' end of the cDNA for the rat farnesyl:protein transferase was used to screen a human retinal λgt10 cDNA library. Approximately $1.0 \times 10^6$ plaques were screened, and 27 positives were identified. Positive clones were analyzed by polymerase chain reaction (PCR), and the clone with the largest insert was purified and subcloned for DNA sequencing. The resulting nucleotide sequence, and corresponding deduced amino acid sequence, obtained for the human α-subunit is set forth as seq id no:6 and no:5, respectively.

To clone the human β-subunit, a cDNA first strand synthesis of human prostate poly(A)+ RNA was first carried out using standard procedures. This cDNA was then employed as a template in a PCR reaction using a primer developed from the rat β-subunit sequence. The PCR-amplified product, which represented about 300 basepairs of the human farnesyl:protein transferase β-subunit was used as a probe to screen a human retinal λgt10 cDNA library. Approximately $1.5 \times 10^6$ plaques were screened, and 10 positive clones identified. Purified clones that hybridized to the probe were subcloned into M13 for DNA sequence analysis. The nucleotide sequence obtained for the human β-subunit cDNA, and deduced amino acid sequence is set forth below as seq id no:8 and no:7, respectively.

A comparison of the human nucleotide sequence to that of rat and yeast revealed the following: Percent Identical Nucleotides in Coding Region of cDNAs

|  | α Subunit | β Subunit |
|---|---|---|
| Rat v. yeast | 37.2 | 41.8 |
| Human v. yeast | 35.9 | 37.3 |
| Human v. rat | 88.2 | 90.1 |

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

1. Bos, J. (1989), *Cancer Res.*, 49:4682–4689.
2. Barbacid (1987), *Ann. Rev. Biochem.*, 56:779–827.
3. Hancock, J. F., et al. (1989), *Cell*, 57:1167–1177.
4. Scheler, W. R. et al. (1989), *Science*, 248:379–385.
5. Gibbs, J. B., et al. (1989), *Micro Rev.*, 53:171–185.
6. Casey, P. J., et al. (1989), *Proc. Natl. Acad. Sci., U.S.A.*, 86:8323–8327.
7. Kamiya, Y., et al. (1978), *Biochem. Biophys. Res. Comm.*, 83:1077–1083.
8. Kamiya, Y., et al. (1979), *N. Agric. Biol. Chem.*, 43:1049–1053.
9. Sakagami, Y., et al. (1981), *Science*, 212:1525–1527.
10. Gutierrez, L., et al. (1989), *Embo J.*, 8:1093–1098.
11. Lowry, D. R. et al. (1989), *Nature*, 341: 384–385.
12. Clarke, E., et al. (1988), *Natl. Acad. Sci. U.S.A.*, 85:4643–4647.
13. Davisson, V. J., et al. (1986), *J. Org. Chem.*, 51:4768–4779.
14. Feig, L. A., et al. (1986), *Proc. Natl. Acad. Sci. U.S.A.*, 83:4607–4611.
15. Farnsworth, D. C., et al. (1989), *J. Biol. Chem.*, 264:20422–20429.
16. Laemmli, U. K. (1970), *Nature*, 227:680–685.
17. Lowry, O. H., et al. (1951), *J. Biol. Chem.*, 193:265–275.
18. Stewart, J. M. et al. (1984), *Solid Phase Peptide Synthesis*, 2nd ed., Pierce Chemical Co., Rockford, Ill.
19. Akada, R., et al. (1989), *Mol. Cell. Biol.*, 9:3491–3498.
20. Gautam, N., et al. (1989), *Science*, 244:971–974
21. Robishaw, J. D., et al (1989), *J. Biol. Chem.*, 264:15758–15761.
22. Ysamane, H. K., et al.(1990),*Proc. Natl. Acad. Sci. USA*, 87:5868–5872.
23. Mumby, S. M., et al. (1990), *Proc. Natl. Acad. Sci. USA*, 87:5873–5877.
24. Sambrook, J., et al, (1989), *Molecular Cloning: A Laboratory Manual*, Cold Spring Harbor Laboratory, Cold Spring Harbor, N.Y.
25. Sanger, F. et al. (1977), *Proc. Natl. Acad. Sci. USA*, 74:5463–5476.
26. Tabor, S., et al. (1987), *Proc. Natl. Acad. Sci. USA*, 84:4767–4771.
27. Glisin, V., et al. (1974), *Biochemistry*, 13:2633–2640.
28. Chirgwin, J. M., et al. (1979), *Biochemistry*, 18:5294–5303.
29. Aviv, H., et al. (1972), *Proc. Natl. Acad. Sci. USA*, 69:1408–1412.
30. Lehrman, M. A., et al. (1987), *J. Biol. Chem.*, 262:3354–3361.
31. Saiki, R. K. et al. (1988), *Science*, 239:487–491.
32. Lee, C. C., et al. (1988), *Science*, 239:1288–1291.
33. Maxam, A. M., et al. (1980), *Methods Enzymol*, 65:499–560.
34. Frohman, M. A., et al. (1988), *Proc. Natl. Acad. Sci. USA*, 85:8998–9002.
35. Seabra, M. C., Reiss, Y., Casey, P. J., Brown, M. S., and Goldstein, J. L. (1991), *Cell*, 65:429–434.
36. Chen, W-J., Andres, D. A., Goldstein, J. L., Russell, D. W. and Brown, M. S. (1991), *Cell* 66, 327–334.
36a. Chen, W-J., Andres, D. A., Goldstein, J. L., and Brown, M. S. (1991), *Proc. Natl. Acac. Sci., USA*, 88, 11368–11372.
37. Sanger, F., Coulson, A. R., Barrell, B. G., Smith, A. J. H. & Roe, B. A. (1980), *J. Mol. Biol.* 143, 161–178.
38. Andersson, S., Davis, D. L., Dahlbäck, H., Jörnvall, H. & Russell, D. W. (1989), *J. Biol. Chem.* 264, 8222–8229.
39. Akusjärvi, G., Svensson, C., and Nygard, O. (1987), *Mol. Cell. Biol.* 7, 549–551.
40. Harlow, E. & Lane, D. (1988), In: *Antibodies: A Laboratory Manual*. Cold Spring Harbour Laboratory Press, New York, pp. 82–83.
41. Kozak, M. (1984). *Nucleic Acids Res.* 12, 857–872.
42. Goodman, L. E., Perou, C. M., Fujiyama, A., and Tamanoi, F. (1988), *Yeast* 4, 271–281.
43. Kyte, J., et al. (1982), *J. Mol. Biol.*, 157:105–132.
44. Goodman, L. E., Judd, S. R., Farnsworth, C. C., Powers, S., Gelb, M. H., Glomset, J. A., and Tamanoi, F. (1990), *Proc. Natl. Acad. Sci. USA*, 87, 9665–9669.
45. Schafer, W. R., Trueblood, C. E., Yang, C-C., Mayer, M. P., Rosenberg, S., Poulter, C. D., Kim, S-H., and Rine, J. (1990), *Science*, 249, 1133–1139.
46. Ashby, M. N., and Edwards, P. A. (1990), *J. Biol. Chem.* 265, 13157–13164.
47. Rossi, G., Jiang, Y., Newman, A. P., and Ferro-Novick, S. (1991), *Nature*, 351, 158–161.
48. Ohya, Y., Goebl, M., Goodman, L. E., Petersen-Bjφrn, S., Friesen, J. D., Tamanoi, F., and Anraku, Y. (1991), J. Biol. Chem., 266, 12356–12360.
49. Khosravi-Far, R., Lutz, R. J., Cox, A. D., Clark, R., Bourne, J. R., Sinensky, M., Balch, W. E., Buss, J. E., and Der, C. J. (1991), Proc. Natl. Acad. Sci. USA, 88, 6264–6268.
50. Reiss, Y., Seabra, M. C., Armstrong, S. A., Slaughter, C. A., Goldstein, J. L., and Brown, M. S. (1991), *J. Biol. Chem.*, 266, 10672–10677.
51. He, B., Chen, P., Chen, S. Y., Vancura, K. L., Michaelis, S., and Powers, S. (1991), *Proc. Natl. Acad. Sci. USA*, 88, 11373–11377.
52. Kohl, N. E., Diehl, R. E., Schaber, M. D., Rands, E., Soderman, D. D., He, B., Moores, S. L., Pompliano, D. L., Ferro-Novick, S., Powers, S., Thomas, K. A., Gibbs, J. B. (1991), *J. Biol., Chem.*, 266, 18884–18888.
53. Goldstein, J. L., Brown, M. S., Stradley, S. J., Reiss, Y., and Gierasch, L. M. (1991), *J. Biol Chem.*, 266, 15575–15578.
54. Lipscomb, W. N. (1974), *Tetrahedron*, 30, 1725–1732.
55. Petrillo, E. W. Jr., Ondetti, M. A. (1982), *Medicinal Res. Rev.*, 2, 1–41.
56. Goldstein, J. L. and Brown, M. S. (1990), *Nature*, 343, 425–430.
57. Farnsworth, C. C., Gelb, M. H., Glomset, J. A. (1990), *Science*, 247, 320–322.
58. Rilling, H. C., Breunger, E., Epstein, W. W., and Crain, P. F. (1990), *Science*, 247, 318–320.
King, H. L. and Rilling, H. C. (1977), *Biochemistry*, 16, 3815–3819.
60. Rilling, H. C. (1985), *Meth. Enzymol.*, 110, 145–152.

---

What is claimed is:

1. A farnesyl transferase inhibitor peptide having from 4 to 10 amino acids and having a carboxy terminal amino acid sequence of -CAAX, wherein:
  C=cysteine;
  A=any aliphatic, aromatic or hydroxy amino acid; and
  X=the amino acid M, S, Q, C, S, A, L, F, V, P, or I.

2. The peptide of claim 1, further defined as a peptide having one of the following amino acid sequences at its carboxy terminus: CVIM; KKSKTKCVIM; TKCVIM; RASNRSCAIM; TQSPQNCSIM; CIIM; CVVM; CVLS; CVLM; CAIM; CSIM; CCVQ; CIIC; CIIS; CVIS; CVLS; CVIA; CVIL; CLIL; CLLL; CTVA; CVAM; CKIM; CLIM; CVLM; CFIM; CVFM; CVIF; CEIM; CGIM; CPIM; CVYM; CVTM; CVPM; CVSM; CVIF; CVIV; CVIP; or CVII.

3. The peptide of claim 1, further defined as a tetrapetide.

4. The peptide of claim 3, further defined as one of the following tetrapeptides: CVIM; CIIM; CVVM; CVLS; CVLM; CAIM; CSIM; CCVQ; CIIC; CIIS; CVIS; CVLS; CVIA; CVIL; CLIL; CLLL; CTVA; CVAM; CKIM; CLIM; CVLM; CFIM; CVFM; CVIF; CEIM; CGIM; CPIM; CVYM; CVTM; CVPM; CVSM; CVIF; CVIV; CVIP; or CVII.

5. The peptide of claim 1, further defined as including a biotin, ester, acyl or alkyl moiety.

6. The peptide of claim 1, further defined as a peptide comprising the structure -C-A1-A2-X at its carboxy terminus, wherein C=cysteine, A1=any aliphatic, aromatic or hydroxy amino acid; A2=any aromatic amino acid or amino acid modified to incorporate one or more aromatic moieties; and X=M, S, Q, C, S, A, L, F, V, P, or I.

7. The peptide of claim 6, further defined as the tetrapeptide CVFM.

8. The peptide of claim 6, wherein the aromatic moiety of the A2 amino acid is comprises a fluoro, chloro, or nitro group.

9. The peptide of claim 8, wherein the A2 amino acid comprises parachlorophenylalanine.

10. The peptide of claim 6, wherein the A2 amino acid comprises a naphthyl ring.

* * * * *

UNITED STATES PATENT AND TRADEMARK OFFICE
CERTIFICATE OF CORRECTION

PATENT NO. : 5,420,245

DATED : May 30, 1995

INVENTOR(S) : Michael S. Brown; Joseph L. Goldstein; Yuval Reiss

It is certified that error appears in the above-identified patent and that said Letters Patent is hereby corrected as shown below:

In claim 2, column 61, line 62, delete "havinq" and insert --having-- therefor.

In claim 3, column 62, line 55, delete "tide" and insert --ptide-- therefor.

In claim 8, column 64, line 1, delete "is".

Signed and Sealed this

Twenty-second Day of August, 1995

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 377 amino acids
( B ) TYPE: amino acid
( C ) STRANDEDNESS: single
( D ) TOPOLOGY: linear ( x i ) SEQUENCE DESCRIPTION: SEQ ID NO:1:

```
Met Ala Ala Thr Glu Gly Val Gly Glu Ser Ala Pro Gly Gly Glu Pro
  1               5                  10                  15
Gly Gln Pro Glu Gln Pro Pro Pro Pro Pro Pro Pro Pro Pro Ala Gln
                 20                  25                  30
Gln Pro Gln Glu Glu Glu Met Ala Ala Glu Ala Gly Glu Ala Ala Ala
                 35                  40                  45
Ser Pro Met Asp Asp Gly Phe Leu Ser Leu Asp Ser Pro Thr Tyr Val
 50                  55                  60
Leu Tyr Arg Asp Arg Ala Glu Trp Ala Asp Ile Asp Pro Val Pro Gln
 65                  70                  75                  80
Asn Asp Gly Pro Ser Pro Val Val Gln Ile Ile Tyr Ser Glu Lys Phe
                 85                  90                  95
Arg Asp Val Tyr Asp Tyr Phe Arg Ala Val Leu Gln Arg Asp Glu Arg
                100                 105                 110
Ser Glu Arg Ala Phe Lys Leu Thr Arg Asp Ala Ile Glu Leu Asn Ala
            115                 120                 125
Ala Asn Tyr Thr Val Trp His Phe Arg Arg Val Leu Leu Arg Ser Leu
130                 135                 140
Gln Lys Asp Leu Gln Glu Glu Met Asn Tyr Ile Ile Ala Ile Ile Glu
145                 150                 155                 160
Glu Gln Pro Lys Asn Tyr Gln Val Trp His His Arg Arg Val Leu Val
                165                 170                 175
Glu Trp Leu Lys Asp Pro Ser Gln Glu Leu Glu Phe Ile Ala Asp Ile
                180                 185                 190
Leu Asn Gln Asp Ala Lys Asn Tyr His Ala Trp Gln His Arg Gln Trp
            195                 200                 205
Val Ile Gln Glu Phe Arg Leu Trp Asp Asn Glu Leu Gln Tyr Val Asp
210                 215                 220
Gln Leu Leu Lys Glu Asp Val Arg Asn Asn Ser Val Trp Asn Gln Arg
225                 230                 235                 240
His Phe Val Ile Ser Asn Thr Thr Gly Tyr Ser Asp Arg Ala Val Leu
                245                 250                 255
Glu Arg Glu Val Gln Tyr Thr Leu Glu Met Ile Lys Leu Val Pro His
                260                 265                 270
Asn Glu Ser Ala Trp Asn Tyr Leu Lys Gly Ile Leu Gln Asp Arg Gly
            275                 280                 285
Leu Ser Arg Tyr Pro Asn Leu Leu Asn Gln Leu Leu Asp Leu Gln Pro
290                 295                 300
Ser His Ser Ser Pro Tyr Leu Ile Ala Phe Leu Val Asp Ile Tyr Glu
305                 310                 315                 320
Asp Met Leu Glu Asn Gln Cys Asp Asn Lys Glu Asp Ile Leu Asn Lys
                325                 330                 335
Ala Leu Glu Leu Cys Glu Ile Leu Ala Lys Glu Lys Asp Thr Ile Arg
                340                 345                 350
Lys Glu Tyr Trp Arg Tyr Ile Gly Arg Ser Leu Gln Ser Lys His Ser
            355                 360                 365
```

Arg Glu Ser Asp Ile Pro Ala Ser Val
370                 375

( 2 ) INFORMATION FOR SEQ ID NO:2:

( i ) SEQUENCE CHARACTERISTICS:
        ( A ) LENGTH: 1701 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

| | | | | | |
|---|---|---|---|---|---|
| GCGGGCCGCG | GAGGGGGCGG | GGCTCCACCA | CCACCTCAGC | TGCGGACGGA | GGCGAGATGG | 60 |
| CGGCCACTGA | GGGGGTCGGG | GAATCTGCGC | CAGGCGGTGA | GCCGGGACAG | CCAGAGCAGC | 120 |
| CGCCGCCCCC | GCCTCCTCCG | CCGCCAGCAC | AGCAGCCGCA | GGAAGAAGAG | ATGGCGGCCG | 180 |
| AGGCCGGGGA | AGCAGCGGCG | TCCCTATGG | ACGACGGGTT | TCTGAGCCTG | GACTCGCCCA | 240 |
| CCTATGTCTT | GTACAGGGAC | AGGGCAGAGT | GGGCTGACAT | AGACCCAGTG | CCCCAGAATG | 300 |
| ATGGCCCCAG | TCCAGTGGTC | CAGATCATCT | ACAGTGAAAA | GTTTAGAGAC | GTCTATGATT | 360 |
| ACTTCCGAGC | TGTTCTGCAG | CGCGATGAAA | GAAGCGAACG | AGCCTTTAAG | CTCACTCGAG | 420 |
| ATGCTATTGA | GTTAAACGCA | GCCAACTATA | CGGTGTGGCA | TTTTCGGAGA | GTTCTCTTGA | 480 |
| GGTCGCTTCA | GAAGGATCTG | CAAGAAGAAA | TGAACTACAT | CATCGCAATA | ATTGAGGAAC | 540 |
| AGCCCAAAAA | CTATCAAGTT | TGGCACCATA | GGAGAGTATT | AGTGGAGTGG | CTGAAAGATC | 600 |
| CTTCTCAAGA | GCTCGAGTTC | ATCGCCGATA | TCCTTAATCA | GGATGCAAAG | AATTACCATG | 660 |
| CCTGGCAGCA | TCGACAGTGG | GTCATTCAGG | AGTTTCGACT | TTGGGATAAT | GAGCTGCAGT | 720 |
| ATGTGGACCA | GCTTCTCAAA | GAGGATGTGA | GAAATAACTC | TGTGTGGAAC | CAAAGACACT | 780 |
| TCGTCATTTC | TAATACCACT | GGCTACAGTG | ATCGCGCTGT | GTTGGAGAGA | AAGTCCAAT | 840 |
| ATACTCTGGA | AATGATCAAA | TTAGTGCCAC | ACAATGAGAG | TGCGTGGAAC | TACTTGAAAG | 900 |
| GGATTTTGCA | GGACCGTGGT | CTTTCCAGAT | ACCCTAATCT | ATTAAACCAG | TTGCTTGATT | 960 |
| TACAACCAAG | TCACAGCTCC | CCCTACCTAA | TTGCCTTTCT | TGTGGATATC | TATGAAGACA | 1020 |
| TGCTGGAAAA | CCAGTGTGAC | AACAAGGAGG | ACATTCTTAA | TAAAGCACTA | GAGTTATGTG | 1080 |
| AGATTCTAGC | TAAAGAAAAG | GACACTATAA | GAAAGGAATA | TTGGAGATAT | ATTGGACGGT | 1140 |
| CCCTCCAGAG | TAAACACAGC | AGAGAAAGTG | ACATACCGGC | GAGTGTATAG | CAGCAAGAGC | 1200 |
| GGCTGGAAGA | AGTGGACAAT | GCTTTCTAAG | GCCTCTTATT | CGGGAGTGTA | GAGCGGTTAG | 1260 |
| AGCGGTCATC | TCATGCCTGT | GAGCTAACGT | TGTCCAGGTG | CTGTTTCTAA | CAAGAACTAA | 1320 |
| GGATGACTCC | TGTGTCTGAC | GCTGTTCAGA | CTAGCTAAGA | GTCGATTTCC | TAAAGCAAGG | 1380 |
| TCATTGGAGG | GGAGGGTGAA | GAAAACTTTC | CCGTAAAGGA | ACTACTGCTT | TTGTAGTCTT | 1440 |
| CCCAACATTT | AATCCAATCC | TGTAGAATCA | GCATCTCCTG | AAAGACATGG | TGCACGGCTG | 1500 |
| TGTGCTGGGC | GTGGCTAAGG | GCAGCTGTGT | CATGGGTTTG | CAGTCATGGG | AACCTCGGAG | 1560 |
| CGCTGCCCGG | GACTGCATTG | ATGATTAGGG | CTGCTGGCCT | CACCCACAGG | ATCTTGCTAT | 1620 |
| CACTGTAACC | AACTAATGCC | AAAAGAAAGG | TTTTATAATA | AAATCACATT | ATCTACAAAC | 1680 |
| AAAAAAAAAA | AAAAAAAAAA | A | | | | 1701 |

( 2 ) INFORMATION FOR SEQ ID NO:3:

( i ) SEQUENCE CHARACTERISTICS:
        ( A ) LENGTH: 437 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Met Ala Ser Ser Ser Ser Phe Thr Tyr Tyr Cys Pro Pro Ser Ser Ser
 1               5                  10                  15

Pro Val Trp Ser Glu Pro Leu Tyr Ser Leu Arg Pro Glu His Ala Arg
            20                  25                  30

Glu Arg Leu Gln Asp Asp Ser Val Glu Thr Val Thr Ser Ile Glu Gln
        35                  40                  45

Ala Lys Val Glu Glu Lys Ile Gln Glu Val Phe Ser Ser Tyr Lys Phe
    50                  55                  60

Asn His Leu Val Pro Arg Leu Val Leu Gln Arg Glu Lys His Phe His
65                  70                  75                  80

Tyr Leu Lys Arg Gly Leu Arg Gln Leu Thr Asp Ala Tyr Glu Cys Leu
                85                  90                  95

Asp Ala Ser Arg Pro Trp Leu Cys Tyr Trp Ile Leu His Ser Leu Glu
            100                 105                 110

Leu Leu Asp Glu Pro Ile Pro Gln Ile Val Ala Thr Asp Val Cys Gln
        115                 120                 125

Phe Leu Glu Leu Cys Gln Ser Pro Asp Gly Gly Phe Gly Gly Gly Pro
    130                 135                 140

Gly Gln Tyr Pro His Leu Ala Pro Thr Tyr Ala Ala Val Asn Ala Leu
145                 150                 155                 160

Cys Ile Ile Gly Thr Glu Glu Ala Tyr Asn Val Ile Asn Arg Glu Lys
                165                 170                 175

Leu Leu Gln Tyr Leu Tyr Ser Leu Lys Gln Pro Asp Gly Ser Phe Leu
            180                 185                 190

Met His Val Gly Gly Glu Val Asp Val Arg Ser Ala Tyr Cys Ala Ala
        195                 200                 205

Ser Val Ala Ser Leu Thr Asn Ile Ile Thr Pro Asp Leu Phe Glu Gly
    210                 215                 220

Thr Ala Glu Trp Ile Ala Arg Cys Gln Asn Trp Glu Gly Gly Ile Gly
225                 230                 235                 240

Gly Val Pro Gly Met Glu Ala His Gly Gly Tyr Thr Phe Cys Gly Leu
                245                 250                 255

Ala Ala Leu Val Ile Leu Lys Lys Glu Arg Ser Leu Asn Leu Lys Ser
            260                 265                 270

Leu Leu Gln Trp Val Thr Ser Arg Gln Met Arg Phe Glu Gly Gly Phe
        275                 280                 285

Gln Gly Arg Cys Asn Lys Leu Val Asp Gly Cys Tyr Ser Phe Trp Gln
    290                 295                 300

Ala Gly Leu Leu Pro Leu Leu His Arg Ala Leu His Ala Gln Gly Asp
305                 310                 315                 320

Pro Ala Leu Ser Met Ser His Trp Met Phe His Gln Gln Ala Leu Gln
                325                 330                 335

Glu Tyr Ile Leu Met Cys Cys Gln Cys Pro Ala Gly Gly Leu Leu Asp
            340                 345                 350

Lys Pro Gly Lys Ser Arg Asp Phe Tyr His Thr Cys Tyr Cys Leu Ser
        355                 360                 365

Gly Leu Ser Ile Ala Gln His Phe Gly Ser Gly Ala Met Leu His Asp
    370                 375                 380

Val Val Met Gly Val Pro Glu Asn Val Leu Gln Pro Thr His Pro Val
385                 390                 395                 400

Tyr Asn Ile Gly Pro Asp Lys Val Ile Gln Ala Thr Thr His Phe Leu
                405                 410                 415

Gln Lys Pro Val Pro Gly Phe Glu Glu Cys Glu Asp Ala Val Thr Ser
            420                 425                 430
```

Asp Pro Ala Thr Asp
435

( 2 ) INFORMATION FOR SEQ ID NO:4:

( i ) SEQUENCE CHARACTERISTICS:
( A ) LENGTH: 2464 base pairs
( B ) TYPE: nucleic acid
( C ) STRANDEDNESS: single
( D ) TOPOLOGY: linear ( x i ) SEQUENCE DESCRIPTION: SEQ ID NO:4:

| | | | | | |
|---|---|---|---|---|---|
| CGGGCGCGTT | GTTGCTGGAC | GAAGCTGAGT | CCTATACAGC | GCTCGCAGCT | CTCCCGATCA | 60 |
| TGGCTTCTTC | GAGTTCCTTC | ACCTATTATT | GTCCTCCATC | TTCTTCCCCT | GTTTGGTCAG | 120 |
| AACCGCTGTA | TAGTCTGAGA | CCTGAGCACG | CGCGGGAGCG | GTTGCAAGAC | GACTCAGTGG | 180 |
| AAACAGTCAC | GTCCATAGAA | CAGGCCAAAG | TAGAAGAAAA | GATCCAGGAG | GTCTTCAGTT | 240 |
| CTTACAAGTT | TAACCACCTC | GTACCAAGGC | TCGTTCTGCA | GAGGGAGAAG | CACTTCCATT | 300 |
| ATCTGAAAAG | AGGCCTTCGA | CAACTGACAG | ATGCCTATGA | GTGTCTGGAT | GCCAGCCGCC | 360 |
| CCTGGCTCTG | CTACTGGATC | CTGCACAGCT | GGAGCTCCT | CGACGAACCC | ATCCCCCAAA | 420 |
| TAGTGGCTAC | AGATGTGTGT | CAGTTCTTGG | AGCTGTGTCA | GAGTCCAGAC | GGTGGCTTTG | 480 |
| GAGGGGGCCC | TGGTCAGTAC | CCACACCTCG | CTCCCACGTA | TGCAGCTGTC | AACGCGCTAT | 540 |
| GCATCATTGG | CACGGAGGAA | GCCTACAACG | TCATTAACAG | AGAGAAGCTC | CTTCAGTACT | 600 |
| TGTACTCCCT | AAAGCAACCG | GATGGCTCTT | TTCTCATGCA | CGTCGGAGGA | GAGGTGGATG | 660 |
| TAAGAAGTGC | GTACTGTGCT | GCCTCAGTAG | CCTCTCTCAC | CAACATCATC | ACTCCTGACC | 720 |
| TCTTCGAAGG | CACTGCTGAA | TGGATAGCAA | GGTGCCAGAA | CTGGGAAGGC | GGCATTGGCG | 780 |
| GGGTGCCAGG | GATGGAAGCC | CACGGTGGCT | ACACCTTCTG | TGGCTTGGCT | GCGCTGGTGA | 840 |
| TCCTCAAGAA | GGAACGTTCT | TTGAACCTGA | AGAGCTTGCT | ACAATGGGTG | ACAAGCCGGC | 900 |
| AGATGCGGTT | CGAAGGAGGA | TTTCAGGGCC | GCTGCAACAA | GCTGGTGGAC | GGCTGCTACT | 960 |
| CCTTCTGGCA | GGCAGGACTT | CTGCCCCTGT | TGCACCGGGC | ACTCCACGCT | CAAGGTGACC | 1020 |
| CTGCCCTCAG | CATGAGCCAC | TGGATGTTCC | ATCAGCAGGC | GCTGCAGGAG | TACATCCTCA | 1080 |
| TGTGCTGCCA | GTGTCCGGCT | GGGGGTCTCC | TGGACAAACC | TGGCAAGTCA | CGTGACTTCT | 1140 |
| ACCATACTTG | CTACTGCCTG | AGCGGCCTGT | CCATTGCCCA | GCATTTTGGA | AGTGGAGCCA | 1200 |
| TGCTGCACGA | TGTGGTCATG | GGTGTGCCTG | AAAATGTTCT | GCAGCCCACT | CACCCTGTGT | 1260 |
| ACAACATCGG | ACCTGATAAG | GTGATCCAGG | CCACCACACA | CTTTCTGCAG | AAGCCGGTCC | 1320 |
| CAGGCTTTGA | GGAATGCGAA | GATGCGGTGA | CCTCAGATCC | TGCCACTGAC | TAGAGGACCC | 1380 |
| CATGGCTCCC | CCAAATCCCC | CGTCAGACAA | GGTTTCTCCG | TTTGGGTACA | TAGCACAGTC | 1440 |
| CGTGCTACTT | GAGCCTTGGC | CACTGTGGAG | TTGTGGTTTC | TTTGTCCTTT | CCTGTCAAAC | 1500 |
| AAAACAAAGC | CATCAGCTCT | GGGTTGGAAT | ACACAATGGT | GTGATTTTTA | AAATTATTTT | 1560 |
| CATACCTGTC | AAACCAAAAC | TCTGGGAGCC | GATGTAGTAA | GCAGGGTTGG | AGAGCAATGC | 1620 |
| ATGCTGGGAA | GCAGCAGCCT | CCTCCAGCAG | CCAGGCCCAC | AATGCTGAAA | TGGAAGGTGT | 1680 |
| CTGTGAGTAT | CTCCACATCA | CAGCCACTGC | TGTGCCTCCC | ACCTACACAC | CATTCAGTCA | 1740 |
| GCAGATGGGC | TCCTCTCTGG | TATAAATGTC | AGCTCTGTGC | AAGGGCGGCG | CTGTGGGTCC | 1800 |
| AGCCAATACA | CGCTCTCTGG | AAAACAGCAC | TGGGCTCCAG | TGGGCATATT | CATACTTGTC | 1860 |
| TCTTTTACCC | CAGTCATTTG | CGAAGGACAG | GGGCCAGGAA | TGAAGAAGGG | TCTTAGATTG | 1920 |
| AGCCCTCCCC | ACAACCTGAG | GAGAACTGAT | CTCATATTTC | TCCAAGGCCA | TGTTTGTATG | 1980 |
| AGCAAGACTT | GTTTTGCCCT | AAGTATGACG | ACTAGACCCA | GGTAATCAAT | TATGAGTGGA | 2040 |

```
AAATCAACCT CTAGGTGAAC TCTGTGCCAG AGGAAGCAGC CTCCCCAGTG TCCAGCCCCC      2100

GCCTCTCCCC ATCATGTACC AGGAGAGGCC CTCCTCACGG CAGTGCTGCA GCCCAGGCTC      2160

CTTCTAGTCC TTTCTCCCCA CCCACCCTCC AAGACAGTGC TCTTTTCTCA TCCAGGGTGT      2220

TAACACTACT AAGGCTTCAC CGTAATCGAT CACTCAGGAT TTACTCCTGC CCTGCCCACT      2280

CCAGGCTCTC TGAAACACAG TCAAGTGCTA GGCAAGCTAG CTGCTGCTGG GACAGTGACC      2340

AGCAGGAAGG CAAGTGCTGT CCGTGTGCTG AATTCTGGAA CTGCCTCTGC ACCGGCTGAG      2400

TTTGCTCACC TATCCACTGC TACAGTCATA GCAAGCTCAT GCCGCTGTCC CAGCCTGTGC      2460

GAGC                                                                   2464
```

(2) INFORMATION FOR SEQ ID NO:5:

(i) SEQUENCE CHARACTERISTICS:
        (A) LENGTH: 379 amino acids
        (B) TYPE: amino acid
        (C) STRANDEDNESS: single
        (D) TOPOLOGY: linear (xi) SEQUENCE DESCRIPTION: SEQ ID NO:5:

```
Met Ala Ala Thr Glu Gly Val Gly Glu Ala Ala Gln Gly Gly Glu Pro
1               5                   10                  15

Gly Gln Pro Ala Gln Pro Pro Gln Pro His Pro Pro Pro Pro Gln
            20              25                  30

Gln Gln His Lys Glu Glu Met Ala Ala Glu Ala Gly Glu Ala Val Ala
        35                  40                  45

Ser Pro Met Asp Asp Gly Phe Val Ser Leu Asp Ser Pro Ser Tyr Val
    50                  55                  60

Leu Tyr Arg Asp Arg Ala Glu Trp Ala Asp Ile Asp Pro Val Pro Gln
65                  70                  75                  80

Asn Asp Gly Pro Asn Pro Val Val Gln Ile Ile Tyr Ser Asp Lys Phe
                85                  90                  95

Arg Asp Val Tyr Asp Tyr Phe Arg Ala Val Leu Gln Arg Asp Glu Arg
            100                 105                 110

Ser Glu Arg Ala Phe Lys Leu Thr Arg Asp Ala Ile Glu Leu Asn Ala
        115                 120                 125

Ala Asn Tyr Thr Val Trp His Phe Arg Arg Val Leu Leu Lys Ser Leu
    130                 135                 140

Gln Lys Asp Leu His Glu Glu Met Asn Tyr Ile Thr Ala Ile Ile Glu
145                 150                 155                 160

Glu Gln Pro Lys Asn Tyr Gln Val Trp His His Arg Arg Val Leu Val
                165                 170                 175

Glu Trp Leu Arg Asp Pro Ser Gln Glu Leu Glu Phe Ile Ala Asp Ile
            180                 185                 190

Leu Asn Gln Asp Ala Lys Asn Tyr His Ala Trp Gln His Arg Gln Trp
        195                 200                 205

Val Ile Gln Glu Phe Lys Leu Trp Asp Asn Glu Leu Gln Tyr Val Asp
    210                 215                 220

Gln Leu Leu Lys Glu Asp Val Arg Asn Asn Ser Val Trp Asn Gln Arg
225                 230                 235                 240

Tyr Phe Val Ile Ser Asn Thr Thr Gly Tyr Asn Asp Arg Ala Val Leu
                245                 250                 255

Glu Arg Glu Val Gln Tyr Thr Leu Glu Met Ile Lys Leu Val Pro His
            260                 265                 270

Asn Glu Ser Ala Trp Asn Tyr Leu Lys Gly Ile Leu Gln Asp Arg Gly
        275                 280                 285
```

|   |   |   |   |   |   |   |   |   |   |   |   |   |   |   |
|---|---|---|---|---|---|---|---|---|---|---|---|---|---|---|
| Leu | Ser | Lys | Tyr | Pro | Asn | Leu | Leu | Asn | Gln | Leu | Leu | Asp | Leu | Gln | Pro |
|     | 290 |     |     |     | 295 |     |     |     |     | 300 |     |     |     |     |     |
| Ser | His | Ser | Ser | Pro | Tyr | Leu | Ile | Ala | Phe | Leu | Val | Asp | Ile | Tyr | Glu |
| 305 |     |     |     |     | 310 |     |     |     |     | 315 |     |     |     |     | 320 |
| Asp | Met | Leu | Glu | Asn | Gln | Cys | Asp | Asn | Lys | Glu | Asp | Ile | Leu | Asn | Lys |
|     |     |     |     | 325 |     |     |     |     | 330 |     |     |     |     | 335 |     |
| Ala | Leu | Glu | Leu | Cys | Glu | Ile | Leu | Ala | Lys | Glu | Lys | Asp | Thr | Ile | Arg |
|     |     |     | 340 |     |     |     |     | 345 |     |     |     |     | 350 |     |     |
| Lys | Glu | Tyr | Trp | Arg | Tyr | Ile | Gly | Arg | Ser | Leu | Gln | Ser | Lys | His | Ser |
|     |     | 355 |     |     |     |     | 360 |     |     |     |     | 365 |     |     |     |
| Thr | Glu | Asn | Asp | Ser | Pro | Thr | Asn | Val | Gln | Gln |     |     |     |     |     |
|     | 370 |     |     |     |     | 375 |     |     |     |     |     |     |     |     |     |

( 2 ) INFORMATION FOR SEQ ID NO:6:

( i ) SEQUENCE CHARACTERISTICS:
( A ) LENGTH: 1664 base pairs
( B ) TYPE: nucleic acid
( C ) STRANDEDNESS: single
( D ) TOPOLOGY: linear ( x i ) SEQUENCE DESCRIPTION: SEQ ID NO:6:

| ATGGCGGCCA | CCGAGGGGGT | CGGGGAGGCT | GCGCAAGGGG | GCGAGCCCGG | GCAGCCGGCG | 60 |
| CAACCCCCGC | CCCAGCCGCA | CCCACCGCCG | CCCCAGCAGC | AGCACAAGGA | AGAGATGGCG | 120 |
| GCCGAGGCTG | GGGAAGCCGT | GGCGTCCCCC | ATGGACGACG | GGTTTGTGAG | CCTGGACTCG | 180 |
| CCCTCCTATG | TCCTGTACAG | GGACAGAGCA | GAATGGGCTG | ATATAGATCC | GGTGCCGCAG | 240 |
| AATGATGGCC | CCAATCCCGT | GGTCCAGATC | ATTTATAGTG | ACAAATTTAG | AGATGTTTAT | 300 |
| GATTACTTCC | GAGCTGTCCT | GCAGCGTGAT | GAAAGAAGTG | AACGAGCTTT | TAAGCTAACC | 360 |
| CGGGATGCTA | TTGAGTTAAA | TGCAGCCAAT | TATACAGTGT | GGCATTTCCG | GAGAGTTCTT | 420 |
| TTGAAGTCAC | TTCAGAAGGA | TCTACATGAG | GAAATGAACT | ACATCACTGC | AATAATTGAG | 480 |
| GAGCAGCCCA | AAAACTATCA | AGTTTGGCAT | CATAGGCGAG | TATTAGTGGA | ATGGCTAAGA | 540 |
| GATCCATCTC | AGGAGCTTGA | ATTTATTGCT | GATATTCTTA | ATCAGGATGC | AAAGAATTAT | 600 |
| CATGCCTGGC | AGCATCGACA | ATGGGTTATT | CAGGAATTTA | ACTTTGGGA  | TAATGAGCTG | 660 |
| CAGTATGTGG | ACCAACTTCT | GAAAGAGGAT | GTGAGAAATA | ACTCTGTCTG | GAACCAAAGA | 720 |
| TACTTCGTTA | TTTCTAACAC | CACTGGCTAC | AATGATCGTG | CTGTATTGGA | GAGAGAAGTC | 780 |
| CAATACACTC | TGGAAATGAT | TAAACTAGTA | CCACATAATG | AAAGTGCATG | GAACTATTTG | 840 |
| AAAGGGATTT | TGCAGGATCG | TGGTCTTTCC | AAATATCCTA | ATCTGTTAAA | TCAATTACTT | 900 |
| GATTTACAAC | CAAGTCATAG | TTCCCCCTAC | CTAATTGCCT | TTCTTGTGGA | TATCTATGAA | 960 |
| GACATGCTAG | AAAATCAGTG | TGACAATAAG | GAAGACATTC | TTAATAAAGC | ATTAGAGTTA | 1020 |
| TGTGAAATCC | TAGCTAAAGA | AAAGGACACT | ATAAGAAAGG | AATATTGGAG | ATACATTGGA | 1080 |
| AGATCCCTTC | AAAGCAAACA | CAGCACAGAA | AATGACTCAC | CAACAAATGT | ACAGCAATAA | 1140 |
| CACCATCCAG | AAGAACTTGA | TGGAATGCTT | TTATTTTTTA | TTAAGGGACC | CTGCAGGAGT | 1200 |
| TTCACACGAG | AGTGGTCCTT | CCCTTTGCCT | GTGGTGTAAA | AGTGCATCAC | ACAGGTATTG | 1260 |
| CTTTTTAACA | AGAACTGATG | CTCCTTGGGT | GCTGCTGCTA | CTCAGACTAG | CTCTAAGTAA | 1320 |
| TGTGATTCTT | CTAAAGCAAA | GTCATTGGAT | GGGAGGAGGA | AGAAAAAGTC | CATAAAGGA  | 1380 |
| ACTTTTGTAG | TCTTATCAAC | ATATAATCTA | ATCCCTTAGC | ATCAGCTCCT | CCCTCAGTGG | 1440 |
| TACATGCGTC | AAGATTTGTA | GCAGTAATAA | CTGCAGGTCA | CTTGTATGTA | ATGGATGTGA | 1500 |
| GGTAGCCGAA | GTTTGGTTCA | GTAAGCAGGG | AATACAGTCG | TTCCATCAGA | GCTGGTCTGC | 1560 |
| ACACTCACAT | TATCTTGCTA | TCACTGTAAC | CAACTAATGC | CAAAAGAACG | GTTTTGTAAT | 1620 |

AAAATTATAG CTGTATCTAA AAAAAAAAAA AAAAAAAAAA AAAA   1664

( 2 ) INFORMATION FOR SEQ ID NO:7:

( i ) SEQUENCE CHARACTERISTICS:
( A ) LENGTH: 387 amino acids
( B ) TYPE: amino acid
( C ) STRANDEDNESS: single
( D ) TOPOLOGY: linear ( x i ) SEQUENCE DESCRIPTION: SEQ ID NO:7:

```
Val Glu Glu Lys Ile Gln Glu Val Phe Ser Ser Tyr Lys Phe Asn His
  1               5                  10                  15

Leu Val Pro Arg Leu Val Leu Gln Arg Glu Lys His Phe His Tyr Leu
             20                  25                  30

Lys Arg Gly Leu Arg Gln Leu Thr Asp Ala Tyr Glu Cys Leu Asp Ala
         35                  40                  45

Ser Arg Pro Trp Leu Cys Tyr Trp Ile Leu His Ser Leu Glu Leu Leu
     50                  55                  60

Asp Glu Pro Ile Pro Gln Ile Val Ala Thr Asp Val Cys Gln Phe Leu
 65                  70                  75                  80

Glu Leu Cys Gln Ser Pro Glu Gly Gly Phe Gly Gly Gly Pro Gly Gln
                 85                  90                  95

Tyr Pro His Leu Ala Pro Thr Tyr Ala Ala Val Asn Ala Leu Cys Ile
             100                 105                 110

Ile Gly Thr Glu Glu Ala Tyr Asp Ile Ile Asn Arg Glu Lys Leu Leu
         115                 120                 125

Gln Tyr Leu Tyr Ser Leu Lys Gln Pro Asp Gly Ser Phe Leu Met His
    130                 135                 140

Val Gly Gly Glu Val Asp Val Arg Ser Ala Tyr Cys Ala Ala Ser Val
145                 150                 155                 160

Ala Ser Leu Thr Asn Ile Ile Thr Pro Asp Leu Phe Glu Gly Thr Ala
                165                 170                 175

Glu Trp Ile Ala Arg Cys Gln Asn Trp Glu Gly Gly Ile Gly Gly Val
            180                 185                 190

Pro Gly Met Glu Ala His Gly Gly Tyr Thr Phe Cys Gly Leu Ala Ala
        195                 200                 205

Leu Val Ile Leu Lys Arg Glu Arg Ser Leu Asn Leu Lys Ser Leu Leu
210                 215                 220

Gln Trp Val Thr Ser Arg Gln Met Leu Phe Glu Gly Gly Phe Gln Gly
225                 230                 235                 240

Arg Cys Asn Lys Leu Val Asp Gly Cys Tyr Ser Phe Trp Gln Ala Gly
                245                 250                 255

Leu Leu Pro Leu Leu His Arg Ala Leu His Ala Gln Gly Asp Pro Ala
            260                 265                 270

Leu Ser Met Ser His Trp Met Phe His Gln Gln Ala Leu Gln Glu Tyr
        275                 280                 285

Ile Leu Met Cys Cys Gln Cys Pro Ala Gly Gly Leu Leu Asp Lys Pro
    290                 295                 300

Gly Lys Ser Arg Asp Phe Tyr His Thr Cys Tyr Cys Leu Ser Gly Leu
305                 310                 315                 320

Ser Ile Ala Gln His Phe Gly Ser Gly Ala Met Leu His Asp Val Val
                325                 330                 335

Leu Gly Val Pro Glu Asn Ala Leu Gln Pro Thr His Pro Val Tyr Asn
            340                 345                 350

Ile Gly Pro Asp Lys Val Ile Gln Ala Thr Thr Tyr Phe Leu Gln Lys
        355                 360                 365
```

```
              Pro  Val  Pro  Gly  Phe  Glu  Glu  Leu  Lys  Asp  Glu  Thr  Ser  Ala  Glu  Pro
                   370                 375                           380

Ala  Thr  Asp
                   385
```

( 2 ) INFORMATION FOR SEQ ID NO:8:

( i ) SEQUENCE CHARACTERISTICS:
    ( A ) LENGTH: 1248 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

```
GTAGAAGAAA  AGATCCAAGA  GGTCTTCAGT  TCTTACAAGT  TCAACCACCT  TGTACCAAGG    60

CTTGTTTTGC  AGAGGGAGAA  GCACTTCCAT  TATCTGAAAA  GAGGCCTTCG  ACAACTGACA   120

GATGCCTATG  AGTGTCTGGA  TGCCAGCCGC  CCATGGCTCT  GCTATTGGAT  CCTGCACAGC   180

TTGGAACTGC  TAGATGAACC  CATCCCCCAG  ATAGTGGCTA  CAGATGTGTG  TCAGTTCCTG   240

GAGCTGTGTC  AGAGCCCAGA  AGGTGGCTTT  GGAGGAGGAC  CCGGTCAGTA  TCCACACCTT   300

GCACCCACAT  ATGCAGCAGT  CAATGCATTG  TGCATCATTG  GCACCGAGGA  GGCCTATGAC   360

ATCATTAACA  GAGAGAAGCT  TCTTCAGTAT  TTGTACTCCC  TGAAGCAACC  TGACGGCTCC   420

TTTCTCATGC  ATGTCGGAGG  TGAGGTGGAT  GTGAGAAGCG  CATACTGTGC  TGCCTCCGTA   480

GCCTCGCTGA  CCAACATCAT  CACTCCAGAC  CTCTTTGAGG  GCACTGCTGA  ATGGATAGCA   540

AGGTGTCAGA  ACTGGGAAGG  TGGCATTGGC  GGGGTACCAG  GGATGGAAGC  CCATGGTGGC   600

TATACCTTCT  GTGGCCTGGC  CGCGCTGGTA  ATCCTCAAGA  GGGAACGTTC  CTTGAACTTG   660

AAGAGCTTAT  TACAATGGGT  GACAAGCCGG  CAGATGCTAT  TTGAAGGAGG  ATTTCAGGGC   720

CGCTGCAACA  AGCTGGTGGA  TGGCTGCTAC  TCCTTCTGGC  AGGCGGGGCT  CCTGCCCCTG   780

CTCCACCGCG  CACTGCACGC  CCAAGGTGAC  CCTGCCCTTA  GCATGAGCCA  CTGGATGTTC   840

CATCAGCAGG  CCCTGCAGGA  GTACATCCTG  ATGTGCTGCC  AGTGCCCTGC  GGGGGGGCTT   900

CTGGATAAAC  CTGGCAAGTC  GCGTGATTTC  TACCACACCT  GCTACTGCCT  GAGCGGCCTG   960

TCCATAGCCC  AGCACTTCGG  CAGCGGAGCC  ATGTTGCATG  ATGTGGTCCT  GGGTGTGCCC  1020

GAAAACGCTC  TGCAGCCCAC  TCACCCAGTG  TACAACATTG  GACCAGACAA  GGTGATCCAG  1080

GCCACTACAT  ACTTTCTACA  GAAGCCAGTC  CCAGGTTTTG  AGGAGCTTAA  GGATGAGACA  1140

TCGGCAGAGC  CTGCAACCGA  CTAGAGGACC  TGGGTCCCGG  CAGCTCTTTG  CTCACCCATC  1200

TCCCCAGTCA  GACAAGGTTT  ATACGTTTCA  ATACATACTG  CATTCTGT                1248
```